(12) United States Patent
Brown

(10) Patent No.: US 7,901,625 B2
(45) Date of Patent: Mar. 8, 2011

(54) SYSTEM FOR PERFORMING DIABETES SELF-CARE

(75) Inventor: Stephen J. Brown, Woodside, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 506 days.

(21) Appl. No.: 11/923,228

(22) Filed: Oct. 24, 2007

(65) Prior Publication Data

US 2008/0103377 A1    May 1, 2008

Related U.S. Application Data

(60) Continuation of application No. 11/748,113, filed on May 14, 2007, which is a continuation of application No. 10/826,107, filed on Apr. 16, 2004, which is a division of application No. 09/422,046, filed on Oct. 20, 1999, now Pat. No. 7,624,028, which is a continuation of application No. 09/271,217, filed on Mar. 17, 1999, now Pat. No. 6,168,563, which is a continuation-in-part of application No. 08/481,925, filed on Jun. 7, 1995, now Pat. No. 5,899,855, which is a continuation of application No. 08/233,397, filed on Apr. 26, 1994, now abandoned.

(51) Int. Cl.
*G01N 33/00* (2006.01)

(52) U.S. Cl. ............. 422/68.1; 422/58; 422/99; 422/104

(58) Field of Classification Search .................... 422/58, 422/68.1, 99, 104
See application file for complete search history.

(56) References Cited

U.S. PATENT DOCUMENTS

| | | | |
|---|---|---|---|
| 3,426,150 | A | 2/1969 | Tygart |
| 3,566,365 | A | 2/1971 | Rawson et al. |
| 3,566,370 | A | 2/1971 | Worthington, Jr. et al. |

(Continued)

FOREIGN PATENT DOCUMENTS

EP    0286456    10/1988

(Continued)

OTHER PUBLICATIONS

90008234_Request_for_Re-examination_5899855_Aug. 17, 2006.

(Continued)

*Primary Examiner* — Sam P Siefke
(74) *Attorney, Agent, or Firm* — Christopher P. Maiorana, PC

(57) ABSTRACT

A system for performing diabetes self-care using at least two devices in communication with one another, comprising (a) a blood glucose monitoring device, including (i) a receptacle for receiving an amount of blood sufficient for the monitoring device to run a blood glucose test sequence, (ii) processing circuitry for controlling a blood glucose test sequence and computing a blood glucose level, (iii) a power source for powering the blood glucose monitoring device, and (b) a portable microprocessor-based device directly coupled with the blood glucose monitoring device for receiving blood glucose test results directly from the blood glucose monitoring device, including (i) a microprocessor that runs according to program instructions stored in a memory for performing analysis of the blood glucose test results, and detecting a need for a change in insulin dosage, (ii) a memory for (A) recording the recorded blood glucose test results, (B) containing programming for establishing a data protocol that allows digital data signal processing, (C) performing analysis of blood glucose, and (D) storing time and date tagged glucose test results and calibration information.

73 Claims, 25 Drawing Sheets

U.S. PATENT DOCUMENTS

| | | |
|---|---|---|
| 3,768,014 A | 10/1973 | Smith |
| 3,910,257 A | 10/1975 | Fletcher et al. |
| 3,920,005 A | 11/1975 | Gombrich et al. |
| 3,996,928 A | 12/1976 | Marx |
| 4,004,577 A | 1/1977 | Sarnoff |
| 4,130,881 A | 12/1978 | Haessler et al. |
| 4,150,284 A | 4/1979 | Trenkler et al. |
| 4,151,407 A | 4/1979 | McBride et al. |
| 4,151,831 A | 5/1979 | Lester |
| 4,173,971 A | 11/1979 | Karz |
| 4,216,462 A | 8/1980 | McGrath et al. |
| 4,227,526 A | 10/1980 | Goss |
| 4,253,521 A | 3/1981 | Savage |
| 4,259,548 A | 3/1981 | Fahey et al. |
| 4,270,547 A | 6/1981 | Steffen et al. |
| 4,296,756 A | 10/1981 | Dunning et al. |
| 4,347,568 A | 8/1982 | Giguere et al. |
| 4,347,851 A | 9/1982 | Jundanian |
| 4,360,345 A | 11/1982 | Hon |
| 4,417,306 A | 11/1983 | Citron et al. |
| 4,422,081 A | 12/1983 | Woods |
| 4,449,536 A | 5/1984 | Weaver |
| 4,465,077 A | 8/1984 | Schneider |
| 4,473,884 A | 9/1984 | Behl |
| 4,519,398 A | 5/1985 | Lisiecki et al. |
| 4,531,527 A | 7/1985 | Reinhold, Jr. |
| 4,546,436 A | 10/1985 | Schneider et al. |
| 4,566,461 A | 1/1986 | Lubell et al. |
| 4,576,578 A | 3/1986 | Parker et al. |
| 4,592,546 A | 6/1986 | Fascenda et al. |
| 4,627,445 A | 12/1986 | Garcia |
| 4,674,652 A | 6/1987 | Aten et al. |
| 4,686,624 A | 8/1987 | Blum et al. |
| 4,694,490 A | 9/1987 | Harvey et al. |
| 4,695,954 A | 9/1987 | Rose et al. |
| 4,706,207 A | 11/1987 | Hennessy et al. |
| 4,712,562 A | 12/1987 | Ohayon et al. |
| 4,722,349 A | 2/1988 | Baumberg |
| 4,729,381 A | 3/1988 | Harada et al. |
| 4,731,726 A | 3/1988 | Allen, III |
| 4,757,022 A | 7/1988 | Shults et al. |
| 4,768,229 A | 8/1988 | Benjamin et al. |
| 4,779,199 A | 10/1988 | Yoneda et al. |
| 4,782,511 A | 11/1988 | Nemec et al. |
| 4,796,639 A | 1/1989 | Snow et al. |
| 4,799,199 A | 1/1989 | Scales, III et al. |
| 4,803,625 A | 2/1989 | Fu et al. |
| 4,835,372 A | 5/1989 | Gombrich et al. |
| 4,838,275 A | 6/1989 | Lee |
| 4,858,354 A | 8/1989 | Gettler |
| 4,858,617 A | 8/1989 | Sanders |
| 4,890,621 A | 1/1990 | Hakky |
| 4,897,869 A | 1/1990 | Takahashi |
| 4,907,973 A | 3/1990 | Hon |
| 4,916,441 A | 4/1990 | Gombrich et al. |
| 4,933,873 A | 6/1990 | Kaufman et al. |
| 4,950,246 A | 8/1990 | Muller |
| 4,953,552 A | 9/1990 | DeMarzo |
| 4,958,632 A | 9/1990 | Duggan |
| 4,958,641 A | 9/1990 | Digby et al. |
| 4,967,756 A | 11/1990 | Hewitt |
| 4,977,899 A | 12/1990 | Digby et al. |
| 4,979,509 A | 12/1990 | Hakky |
| 4,995,402 A | 2/1991 | Smith et al. |
| 5,007,429 A | 4/1991 | Treatch et al. |
| 5,016,172 A | 5/1991 | Dessertine |
| 5,019,974 A | 5/1991 | Beckers |
| 5,024,225 A | 6/1991 | Fang |
| 5,025,374 A | 6/1991 | Roizen et al. |
| 5,034,807 A | 7/1991 | Von Kohorn |
| 5,036,462 A | 7/1991 | Kaufman et al. |
| 5,036,852 A | 8/1991 | Leishman |
| 5,049,487 A | 9/1991 | Phillips et al. |
| 5,050,612 A | 9/1991 | Matsumura |
| 5,056,059 A | 10/1991 | Tivig et al. |
| 5,059,394 A | 10/1991 | Phillips et al. |
| 5,065,315 A | 11/1991 | Garcia |
| 5,068,536 A | 11/1991 | Rosenthal |
| 5,074,317 A | 12/1991 | Bondell et al. |
| 5,077,476 A | 12/1991 | Rosenthal |
| 5,095,798 A | 3/1992 | Okada et al. |
| 5,109,414 A | 4/1992 | Harvey et al. |
| 5,109,974 A | 5/1992 | Beer et al. |
| 5,111,396 A | 5/1992 | Mills et al. |
| 5,111,817 A | 5/1992 | Clark et al. |
| 5,111,818 A | 5/1992 | Suzuki et al. |
| 5,120,230 A | 6/1992 | Clark et al. |
| 5,120,421 A | 6/1992 | Glass et al. |
| 5,128,752 A | 7/1992 | Von Kohorn |
| 5,134,391 A | 7/1992 | Okada |
| 5,142,358 A | 8/1992 | Jason |
| 5,142,484 A | 8/1992 | Kaufman et al. |
| 5,176,502 A | 1/1993 | Sanderson et al. |
| 5,182,707 A | 1/1993 | Cooper et al. |
| 5,204,670 A | 4/1993 | Stinton |
| 5,216,597 A | 6/1993 | Beckers |
| 5,222,020 A | 6/1993 | Takeda |
| 5,227,874 A | 7/1993 | Von Kohorn |
| 5,228,450 A | 7/1993 | Sellers |
| 5,231,990 A | 8/1993 | Gauglitz |
| 5,249,044 A | 9/1993 | Von Kohorn |
| 5,251,126 A | 10/1993 | Kahn et al. |
| 5,261,401 A | 11/1993 | Baker et al. |
| 5,262,943 A | 11/1993 | Thibado et al. |
| 5,265,888 A | 11/1993 | Yamamoto et al. |
| 5,266,179 A | 11/1993 | Nankai et al. |
| 5,275,159 A | 1/1994 | Griebel |
| 5,282,950 A | 2/1994 | Dietze et al. |
| 5,299,121 A | 3/1994 | Brill et al. |
| 5,301,105 A | 4/1994 | Cummings, Jr. |
| 5,304,468 A | 4/1994 | Phillips et al. |
| 5,307,263 A | 4/1994 | Brown |
| 5,309,919 A | 5/1994 | Snell et al. |
| 5,329,459 A | 7/1994 | Kaufman et al. |
| 5,329,608 A | 7/1994 | Bocchieri et al. |
| 5,331,549 A | 7/1994 | Crawford, Jr. |
| 5,336,245 A | 8/1994 | Theodore et al. |
| 5,339,821 A | 8/1994 | Fujimoto |
| 5,341,291 A | 8/1994 | Roizen et al. |
| 5,343,239 A | 8/1994 | Lappington et al. |
| 5,344,324 A | 9/1994 | O'Donnell et al. |
| 5,357,427 A | 10/1994 | Langen et al. |
| 5,366,896 A | 11/1994 | Margrey et al. |
| 5,371,687 A | 12/1994 | Holmes, II et al. |
| 5,375,604 A | 12/1994 | Kelly et al. |
| 5,377,100 A | 12/1994 | Pope et al. |
| 5,390,238 A | 2/1995 | Kirk et al. |
| 5,399,821 A | 3/1995 | Inagaki et al. |
| 5,410,471 A | 4/1995 | Alyfuku et al. |
| 5,410,474 A | 4/1995 | Fox |
| 5,429,140 A | 7/1995 | Burdea et al. |
| 5,431,691 A | 7/1995 | Snell et al. |
| 5,434,611 A | 7/1995 | Tamura |
| 5,438,607 A | 8/1995 | Przygoda, Jr. et al. |
| 5,441,047 A | 8/1995 | David et al. |
| 5,454,721 A | 10/1995 | Kuch |
| 5,454,722 A | 10/1995 | Holland et al. |
| 5,456,606 A | 10/1995 | McIntyre |
| 5,456,692 A | 10/1995 | Smith, Jr. et al. |
| 5,458,123 A | 10/1995 | Unger |
| 5,465,082 A | 11/1995 | Chaco |
| 5,467,269 A | 11/1995 | Flaten |
| 5,471,039 A | 11/1995 | Irwin, Jr. et al. |
| 5,483,276 A | 1/1996 | Brooks et al. |
| 5,488,412 A | 1/1996 | Majeti et al. |
| 5,488,423 A | 1/1996 | Walkingshaw et al. |
| 5,501,231 A | 3/1996 | Kaish |
| 5,502,636 A | 3/1996 | Clarke |
| 5,502,726 A | 3/1996 | Fischer |
| 5,504,519 A | 4/1996 | Remillard |
| 5,507,288 A | 4/1996 | Bocker et al. |
| 5,517,405 A | 5/1996 | McAndrew et al. |
| 5,518,001 A | 5/1996 | Snell |
| 5,519,433 A | 5/1996 | Lappington et al. |
| 5,544,649 A | 8/1996 | David et al. |
| 5,546,943 A | 8/1996 | Gould |
| 5,549,117 A | 8/1996 | Tacklind et al. |

| | | | | | | |
|---|---|---|---|---|---|---|
| 5,550,575 A | 8/1996 | West et al. | | 5,995,969 A | 11/1999 | Lee et al. |
| 5,553,609 A | 9/1996 | Chen et al. | | 5,997,476 A | 12/1999 | Brown |
| 5,558,638 A | 9/1996 | Evers et al. | | 6,001,065 A | 12/1999 | DeVito |
| 5,564,429 A | 10/1996 | Bornn et al. | | 6,022,315 A | 2/2000 | Iliff |
| 5,569,212 A | 10/1996 | Brown | | 6,022,615 A | 2/2000 | Rettenbacher |
| 5,572,421 A | 11/1996 | Altman et al. | | 6,029,138 A | 2/2000 | Khorasani et al. |
| 5,574,828 A | 11/1996 | Hayward et al. | | 6,035,328 A | 3/2000 | Soukal |
| 5,576,952 A | 11/1996 | Stutman et al. | | 6,046,761 A | 4/2000 | Echerer |
| 5,590,648 A | 1/1997 | Mitchell et al. | | 6,049,794 A | 4/2000 | Jacobs et al. |
| 5,596,994 A | 1/1997 | Bro | | 6,050,940 A | 4/2000 | Braun et al. |
| 5,597,307 A | 1/1997 | Redford et al. | | 6,055,314 A | 4/2000 | Spies et al. |
| 5,601,435 A | 2/1997 | Quy | | 6,055,487 A | 4/2000 | Margery et al. |
| 5,613,495 A | 3/1997 | Mills et al. | | 6,055,506 A | 4/2000 | Frasca, Jr. |
| 5,619,991 A | 4/1997 | Sloane | | 6,057,758 A | 5/2000 | Dempsey et al. |
| 5,624,265 A | 4/1997 | Redford et al. | | 6,110,148 A | 8/2000 | Brown et al. |
| 5,628,309 A | 5/1997 | Brown | | 6,138,145 A | 10/2000 | Kawanaka |
| 5,629,981 A | 5/1997 | Nerlikar | | 6,144,837 A | 11/2000 | Quy |
| 5,631,844 A | 5/1997 | Margrey et al. | | 6,151,586 A | 11/2000 | Brown |
| 5,633,910 A | 5/1997 | Cohen | | 6,168,563 B1 | 1/2001 | Brown |
| 5,640,953 A | 6/1997 | Bishop et al. | | 6,177,940 B1 | 1/2001 | Bond et al. |
| 5,642,731 A | 7/1997 | Kehr | | 6,189,029 B1 | 2/2001 | Fuerst |
| 5,642,936 A | 7/1997 | Evans | | 6,221,012 B1 | 4/2001 | Maschke et al. |
| 5,666,487 A | 9/1997 | Goodman et al. | | 6,248,065 B1 | 6/2001 | Brown |
| 5,670,711 A | 9/1997 | Detournay et al. | | 6,334,778 B1 | 1/2002 | Brown |
| 5,675,635 A | 10/1997 | Vos et al. | | 6,368,273 B1 | 4/2002 | Brown |
| 5,678,562 A | 10/1997 | Sellers | | 2003/0126593 A1 | 7/2003 | Mault et al. |
| 5,678,571 A | 10/1997 | Brown | | 2004/0106855 A1 | 6/2004 | Brown et al. |
| 5,687,322 A | 11/1997 | Deaton et al. | | | | |
| 5,687,717 A | 11/1997 | Halpern et al. | | FOREIGN PATENT DOCUMENTS | | |
| 5,687,734 A | 11/1997 | Dempsey et al. | | EP | 0320749 | 6/1989 |
| 5,704,364 A | 1/1998 | Saltzstein et al. | | EP | 370599 | 5/1990 |
| 5,704,366 A | 1/1998 | Tacklind et al. | | EP | 0461910 | 12/1991 |
| 5,704,902 A | 1/1998 | Vandenbelt et al. | | EP | 508912 | 10/1992 |
| 5,711,297 A | 1/1998 | Iliff | | EP | 526166 | 2/1993 |
| 5,715,451 A | 2/1998 | Marlin | | EP | 0653718 | 5/1995 |
| 5,715,823 A | 2/1998 | Wood et al. | | EP | 676709 | 10/1995 |
| 5,717,913 A | 2/1998 | Driscoll | | EP | 680727 | 11/1995 |
| 5,720,733 A | 2/1998 | Brown | | EP | 761160 | 3/1997 |
| 5,722,418 A | 3/1998 | Bro | | EP | 0251520 | 1/1998 |
| 5,727,153 A | 3/1998 | Powell | | GB | 2218831 | 11/1989 |
| 5,730,124 A | 3/1998 | Yamauchi | | GB | 2225637 | 6/1990 |
| 5,732,696 A | 3/1998 | Rapoport et al. | | WO | WO-8501667 | 4/1985 |
| 5,732,709 A | 3/1998 | Tacklind et al. | | WO | WO-90/00367 | 1/1990 |
| 5,734,413 A | 3/1998 | Lappington et al. | | WO | WO-9109374 | 6/1991 |
| 5,752,234 A | 5/1998 | Withers | | WO | WO-93/01489 | 1/1993 |
| 5,760,771 A | 6/1998 | Blonder et al. | | WO | WO-9302622 | 2/1993 |
| 5,772,585 A | 6/1998 | Lavin et al. | | WO | WO-9416774 | 8/1994 |
| 5,778,882 A | 7/1998 | Raymond et al. | | WO | WO-95/09386 | 4/1995 |
| 5,782,814 A | 7/1998 | Brown et al. | | WO | WO-95/20199 | 7/1995 |
| 5,785,650 A | 7/1998 | Akasaka et al. | | WO | WO-9529447 | 11/1995 |
| 5,791,342 A | 8/1998 | Woodard | | WO | WO-97/08605 | 3/1997 |
| 5,792,117 A | 8/1998 | Brown | | WO | WO-97/12544 | 4/1997 |
| 5,793,969 A | 8/1998 | Kamentsky et al. | | WO | WO-98/16895 | 4/1998 |
| 5,796,393 A | 8/1998 | MacNaughton | | | | |
| 5,802,494 A | 9/1998 | Kuno | | OTHER PUBLICATIONS | | |
| 5,810,747 A | 9/1998 | Brudny et al. | | | | |
| 5,822,544 A | 10/1998 | Chaco et al. | | 90008909_Request_for_Re-examination_5899855_Oct. 29, 2007. | | |
| 5,822,715 A * | 10/1998 | Worthington et al. .......... 702/19 | | | | |
| 5,825,283 A | 10/1998 | Camhi | | 90010053_Request_for_Re-examination_7223236_Nov. 9, 2007. | | |
| 5,827,180 A | 10/1998 | Goodman | | | | |
| 5,828,943 A | 10/1998 | Brown | | 95000386_Request_for_Re-examination_7223236_Aug. 26, 2008. | | |
| 5,835,896 A | 11/1998 | Fisher et al. | | | | |
| 5,868,669 A | 2/1999 | Iliff | | 0000_00_00_American_Heritage_Dictionary_pa. | | |
| 5,875,432 A | 2/1999 | Sehr | | 0000_00_00_American_Heritage_Dictionary_pe. | | |
| 5,879,163 A | 3/1999 | Brown et al. | | 0000_00_00_Websters_Dictionary_II_com. | | |
| 5,893,077 A | 4/1999 | Griffin | | 0000_00_00_Websters_Dictionary_II_con. | | |
| 5,893,098 A | 4/1999 | Peters et al. | | 0000_00_00_Websters_Dictionary_II_i. | | |
| 5,897,493 A | 4/1999 | Brown | | 0000_00_00_Websters_Dictionary_II_m. | | |
| 5,899,855 A | 5/1999 | Brown | | 1978_11_00_Licklider_Applications_of_Information_Network. | | |
| 5,911,687 A | 6/1999 | Sato et al. | | | | |
| 5,913,310 A | 6/1999 | Brown | | Oct. 19, 1986_Thompson_In_Vivo_Probes. | | |
| 5,918,603 A | 7/1999 | Brown | | Jun. 2, 1987_U.S. Appl. No. 07/096,998_Amendment. | | |
| 5,920,477 A | 7/1999 | Hofbert et al. | | Aug. 10, 1988_U.S. Appl. No. 06/879,900_Amendment. | | |
| 5,933,136 A | 8/1999 | Brown | | 1989_05_00_Paperny_Adolescent_Pregnancy_Prevention. | | |
| 5,941,829 A | 8/1999 | Saltzstein et al. | | Jul. 23, 1991_The_Physicians_Guide_From_The_K864318_510K. | | |
| 5,961,446 A | 10/1999 | Beller et al. | | | | |
| 5,983,217 A | 11/1999 | Khosravi-Sichani et al. | | Aug. 17, 2006_Abbott_Amended_Complaint. | | |
| 5,987,471 A | 11/1999 | Bodine et al. | | | | |
| 5,988,855 A | 11/1999 | Morobin | | | | |

May 9, 2007_Leapfrog_v_Fisher_Price.
Jan. 25, 2008_The_Physicians_Guide_Become_Publicly_Available.
Excerpts_From_the_Prosecution_History_for_US_Patent_5899855.
Hughes_Bedside_Terminals_Clinicom_MD_1988.
Velho et al., Biomed. Biochim. Acta (1989) 48(11/12):957:964.
+5V Powered Isolated RS-232 Drivers/Receivers Maxim Integrated Products.
Albisser, A.M. "Intelligent Instrumentation in Diabetic Management", CRC Critical Reviews in Biomedical Engineering, vol. 17, No. 1, pp. 1-24.
Anonymous, "Health Hero Network, Inc. Receives First-Ever FDA Clearance for Connecting Medical Devices to Internet", PR Newswire, (Dec. 2, 1993), 3 pages.
Billiard, A., et al. "Telematic Transmission of Computerized Blood Glucose Profiles for IDDm Patients", Diabetes Care, (Feb. 1991), vol. 14, No. 2, pp. 130-134.
Blood Glucose Monitors, Portable Health Device, (1998), vol. 17(9), pp. 253-271.
Bower, "Brain Clues to Energy-efficient Learning", Science News, (Apr. 1992), v. 141; p. 215(1); Dialog: File 647, Acct# 12123949.
Bruce, "Health Hero Network CEO, CNNfn", Digital Jam, (Dec. 1, 1999), 3.
Bruce, et al., "The Effects of Sympathetic Nervous System Activation and Psychological Stress . . . "; Diabetologia; 35(9); 1992; 835-843; Dialog: File 5, Acc#9629427. (9 pages).
Brunetti, P., et al., "A Simulation Study on a Self-Turning Portable Controller of Blood Glucose", The International Journal of Artificial Organs, (1993), vol. 16, No. 16, pp. 51-57.
Caprihan, A., et al., "A Simple Microcomputer for Biomedical Signal Processing", IECI '78 Annual Conference Proceedings on Industrial Applications of Microprocessors, (Mar. 20, 1978), 18-23.
CD-ROM Mavericks: Proprietary TV-Based Players, Byte Guide to CD-ROM, pp. 100-105.
Central Fetal Monitoring Systems with Optical Disk Storage, New Technology Brief, (Nov./Dec. 1998), vol. 2, No. 6, pp. 249-251.
Cheng, Joe H., "PCT Search Report", (Jan. 11, 1996).
Douglas, A.S., et al., "Hand-Held Glucose Monitor and Recorder", Proceedings of the Annual International Conference of the IEEE Engineering in Medicine and Biology Society, New Orleans, LA, (Nov. 1988), pp. 747-748.
EP European Search Report, From 6858P005EP, (Mar. 27, 1998).
Fabietti, P.G., et al., "Wearable System for Acquisition, Processing and Storage of the Signal from Amperometric Glucose Sensors", The International Journal of Artificial Organs, (1991), vol. 14, No. 3, pp. 175-178.
Finston, "Parent + Teacher = Healthy Child", Diabetes Forecast, (Apr. 1994), v47 n9; p. 26(5); Dialog: file 149, Acc# 15804228.
Fox, "Not My Type: Type B Behavior, Type I Diabetes Plus Stress Equals Blood Sugar Blues", Health, (Mar. 1998), v20 n3; pp. 22(1); Dialog: File 149, Acc# 06397959.
Frieberger, Paul, "Video Game Takes on Diabetes Superhero 'Captain Novolin' Offers Treatment Tips", San Francisco Examiner, (Jun. 26, 1992), Fourth Edition, Business Section B1.
Guiffrida, et al., Should We Pay the Patient? Review of Financial Incentives to enhance Patient Compliance:, Biomedical Journal, (1997), vol. 315, pp. 703-707.
Hauben, Jay R., "A Brief History of the Cleveland Free-Net", available at http://www.ais.org/~irh/acn7-1.a09.html, (1995) pp. 1-4.
Hauser, et al., "Will Computers Replace or Complement the Diabetes Educator?", The Medical Journal of Australia, (Oct. 5, 1992), vol. 157, 489-491.
Horio, Hiroyuki, et al., "Clinical Telecommunication Network System for Home Monitoring", Medical & Biological Engineering & Computing, (Mar. 1994), vol. 32, 227-230.
How Flash Memory Works, Internet printout of URL address: http://www.howstuffworks.com/flash-memory4.htm, (Sep. 28, 2002), 2 pages.
Hunter, "Technological Advances in Bedside Monitoring: Biosensors", Archives and Laboratory Medicine, (Jul. 1987), pp. 633-636.

Introducing the Next Generation of About Your Diabetes, U.S. Pharmacopical Convention and American Diabetes Association, (1993).
Kauffmann, et al., "Epidemiological Study of the Genetics and Environment of Asthma, Bronchial Hyperresponsiveness and Atrophy", Am. J. Respir. Crit. Care Med., (1997), vol. 156, pp. S123-S129.
Kaufman, Steven, B., "The Learning Game", Nation's Business, (Nov. 1993).
Kuykendall, V.G., et al., "Assessment of Self-Monitored Blood Glucose results Using a Reflectance Meter with Memory and Microcomputer", Symposium on Computer Applications in Medical Care, (Jan. 1981), vol. 70, pp. 98-102.
Lacyk, John, "PCT Search Report", (Jun. 12, 1997).
Latman, N.S., "Evaluation of Electronic, Digital Blood Glucose Monitors", Biomedical Instrumentation and Technology, (1991), vol. 25, No. 1, 43-49.
Leyerle, Beverly J., et al., "The PDMS as a Focal Point for Distributed Patient Data", International Journal of Clinical Monitoring and Computing, (1988), vol. 5, pp. 155-161.
Makikawa, M., et al., "Microprocessor-Based Memory Device for Ambulatory Heart Rate and Physical Activity Recording", Methods of Information in Medicine, (1994), vol. 33, No. 1, pp. 94-96.
Marsh, David G. "Approaches Toward the Genetic Analysis of Complex Traits Asthma and Atrophy", Am. J. Respir.Crit.Care Med., (1997), vol. 156, pp. S-133-S138.
Martinez, Fernando D., "Complexities of the Genetics of Asthma", Am.J. Respir. Crit. Care Med., (1997), vol. 156, pp. S117-S122.
Mazzola, et al., "Video Diabetes: A Teaching Tool for Children with Insulin-Dependent Diabetes", Proceedings—7th Annual Symposium on Computer Applications in Medical Care; Washington, DC; Dialog:, (Oct. 1983), File 8, Acc# 01624462.
Meissner, et al., "Building an Integrated Clinical and Research Network", Proceedings of the SPIE, (Oct. 24, 1995), vol. 2618, p. 92-99.
Miles, Laughton E., "A Portable Microcomputer for Long-Term Physiological Monitoring in the Home and Work Environment", Medical Monitoring in the Home and Work Environment, (1990), pp. 47-57.
Moore, "New Applications Break Through Storage Boundaries", Computer Technology Review, (Oct. 1999), vol. 19, No. 10 p. 1.
Pfeiffer, E. F., "The Glucose Sensor: The Missing Link in Diabetes Therapy", Hormone and Metabolic Research, (1990), vol. 24m Suppl. pp. 154-164.
Poitout, V., et al. "A Glucose Monitoring System for On Line Estimation in Man of Blood Glucose Concentration Using a Miniaturized Glucose Sensor Implanted in the Subcutaneous Tissue and a Wearable Control Unit", Diabetologia, (1993), vol. 36, pp. 658-663.
Potter, David, "Fundamentals of PC-Based Data Acquisition", Sensors, (Feb. 1994), pp. 12-20.
Reis, H, "Telemedicine: Transmitting Expertise to the Point of Care Toward an Electronic Patient Record"; '97, Nashville, TN, Apr. 27-May 3, 1997, pp. 248-256, v. 3.
Roberts; "Diabetes and Stress: A Type A Connection?", Psychology Today, (Jul. 1987), v. 21; pp. 22(1); Dialog: File 149, Acc# 05038381.
Rose, V. L., et al., "Decentralized Testing for Prothrombin Time and Activated Partial Thromboplastin Time Using a Dry Chemistry Portable Analyser", Archives of Pathology and Laboratory Medicine, (Jun. 1993), vol. 117, pp. 611-617.
Schenkels, P., "Supplementary European Search Report", Application No. EP 97 92 2716, (Mar. 11, 2002).
Schork, Nicholas J., "Genetics of Complex Disease", Am.J.Respir. Crit. Care Me., (1997), vol. 156, pp. S103-S109.
Schrezenmeir, J. et al., "Computer Assisted Insulin Dosage Adjustment—Perspective for Diabetes Control", Hormone and Metabolic Research, Supplement Series, (1990), vol. 24, pp. 116-123.
Shandle, Jack, "Who Will Dominate The Desktop in the 90's?", , Electronics, Feb. 1990, pp. 48-50. (3 pages) Cited by 2 patents.
Shults, Marc C., et al., "A Telemetry-Instrumentation System for Monitoring Multiple Subcutaneously Implanted Glucose Sensors", IEEE Transactions on Biomedical Engineering, (Oct. 1994), vol. 41, No. 10, pp. 937-942.
Soeldner, J. S., "Treatment of Diabetes Mellitus by Devices", The American Journal of Medicine, (Jan. 1981), vol. 70, 183-194.

Tandy Radio Shack, "The description of the Tandy Radio Shack TRS-80 Model 100/102 device available at http://www.old-computuers.com/musuem/computer.asp?c=233", World Wide Web, (Feb. 13, 2004), 1-3.

Updike, Stuart J., et al., "Laboratory Evaluation of New Reusable Blood Glucose Sensor", Diabetes Care, (Nov./Dec. 1998), vol. 11, No. 10, pp. 801-807.

Vallera, D. A., et al., "Accuracy of Portable Blood Glucose Monitoring", American Journal of Clinical Pathology, (1991), vol. 95, No. 2, pp. 247-252.

Voelker, Rebecca, "Shoe Leather Therapy is Gaining on TB", Jama, (Mar. 13, 1996), vol. 275, 743.

Wyatt, J. C., "Clinical Data Systems, Part 2: Components and Techniques", Lancet, (Dec. 1994), vol. 344, No. 8937, pp. 1609-1614.

Yoshizawa, Daisuke, et al., "The Development of a Data Processing System with Personal Computer MSX Standard System for Flow Injection Analysis", Journal of Flow Injection Analysis, (1988), V.5, No. 2, pp. 101-110.

* cited by examiner

```
Glucose
Ave: 123 mg/dl
SD:   56
Num: 15
No. under 50:  13
No. hypo sym: 23
```

```
June 12 9:30pm
BG      113   mg/dl
Regin   12.5 U
NPHin   13.2 U
Food    1    BE
Pre-meal     HYPO
```

SCRIPT ENTRY SCREEN

SCRIPT NAME: DIABETES SCRIPT 1

| QUERIES | CHOICE 1 | CHOICE 2 | CHOICE 3 | CHOICE 4 |
|---|---|---|---|---|
| HOW DO YOU FEEL? | VERY BAD | BAD | GOOD | VERY GOOD |
| HOW WELL ARE YOU MANAGING YOUR DISEASE? | VERY BADLY | BADLY | WELL | VERY WELL |
| HOW HARD IS IT FOR YOU TO FOLLOW YOUR TREATMENT PLAN? | VERY HARD | HARD | EASY | VERY EASY |
| HOW HARD IS IT FOR YOU TO CONTROL YOUR BLOOD SUGAR? | VERY HARD | HARD | EASY | VERY EASY |

SELECT DEVICE TYPE(S)
☒ GLUCOSE METER  ☐ RESPIRATORY FLOW METER  ☐ BP CUFF

CONNECTION TIME: 03:00 ▽   [CREATE SCRIPT]   [CANCEL]

Fig. 16

NUMBER: 9001 {LF}

LED: 1 {LF}

ZAP: {LF}

CLS: {LF}

DISPLAY: ANSWER QUERIES NOW?
                        PRESS ANY BUTTON TO START {LF}

WAIT: {LF}

CLS: {LF}

DISPLAY: HOW DO YOU FEEL?
                    VERY                    VERY
                    BAD     BAD     GOOD     GOOD {LF}

INPUT: 0000 {LF}

CLS: {LF}

DISPLAY: HOW WELL ARE YOU
                    MANAGING YOUR DISEASE?
                    VERY                    VERY
                    WELL    BADLY   WELL    WELL {LF}

INPUT: 0000 {LF}

CLS: {LF}

DISPLAY: HOW HARD IS IT FOR YOU TO
                    FOLLOW YOUR TREATMENT PLAN?
                    VERY                    VERY
                    HARD    HARD    EASY    EASY {LF}

INPUT: 0000 {LF}

CLS: {LF}

DISPLAY: HOW HARD IS IT FOR YOU TO
                    CONTROL YOUR BLOOD SUGAR?
                    VERY                    VERY
                    HARD    HARD    EASY    EASY {LF}

*Fig. 17A*

INPUT: 0000 {LF}

CLS: {LF}

DISPLAY: CONNECT GLUCOSE METER
                AND PRESS ANY BUTTON
                WHEN FINISHED {LF}

WAIT: {LF}

CLS: {LF}

DISPLAY: COLLECTING MEASUREMENTS {LF}

COLLECT: GLUCOSE_METER {LF}

CLS: {LF}

DISPLAY: CONNECT APPARATUS TO
                TELEPHONE JACK AND
                PRESS ANY BUTTON
                WHEN FINISHED {LF}

WAIT: {LF}

LED: 0 {LF}

CLS: {LF}

DELAY: 03:00 {LF}

DISPLAY: CONNECTING TO SERVER {LF}

CONNECT: {LF}

{EOF}

PATIENT REPORT 2058

PATIENT: LINDSEY, DAN 2042

QUERY RESPONSES

HOW DO YOU FEEL? BAD

HOW WELL ARE YOU MANAGING YOUR DISEASE? BADLY

HOW HARD IS IT FOR YOU TO FOLLOW YOUR TREATMENT PLAN? HARD

HOW HARD IS IT FOR YOU TO CONTROL YOUR BLOOD SUGAR? VERY HARD

DATE OF MEASUREMENT: 2116 MARCH 15, 1997

MG/DL vs HOURS (6–24)

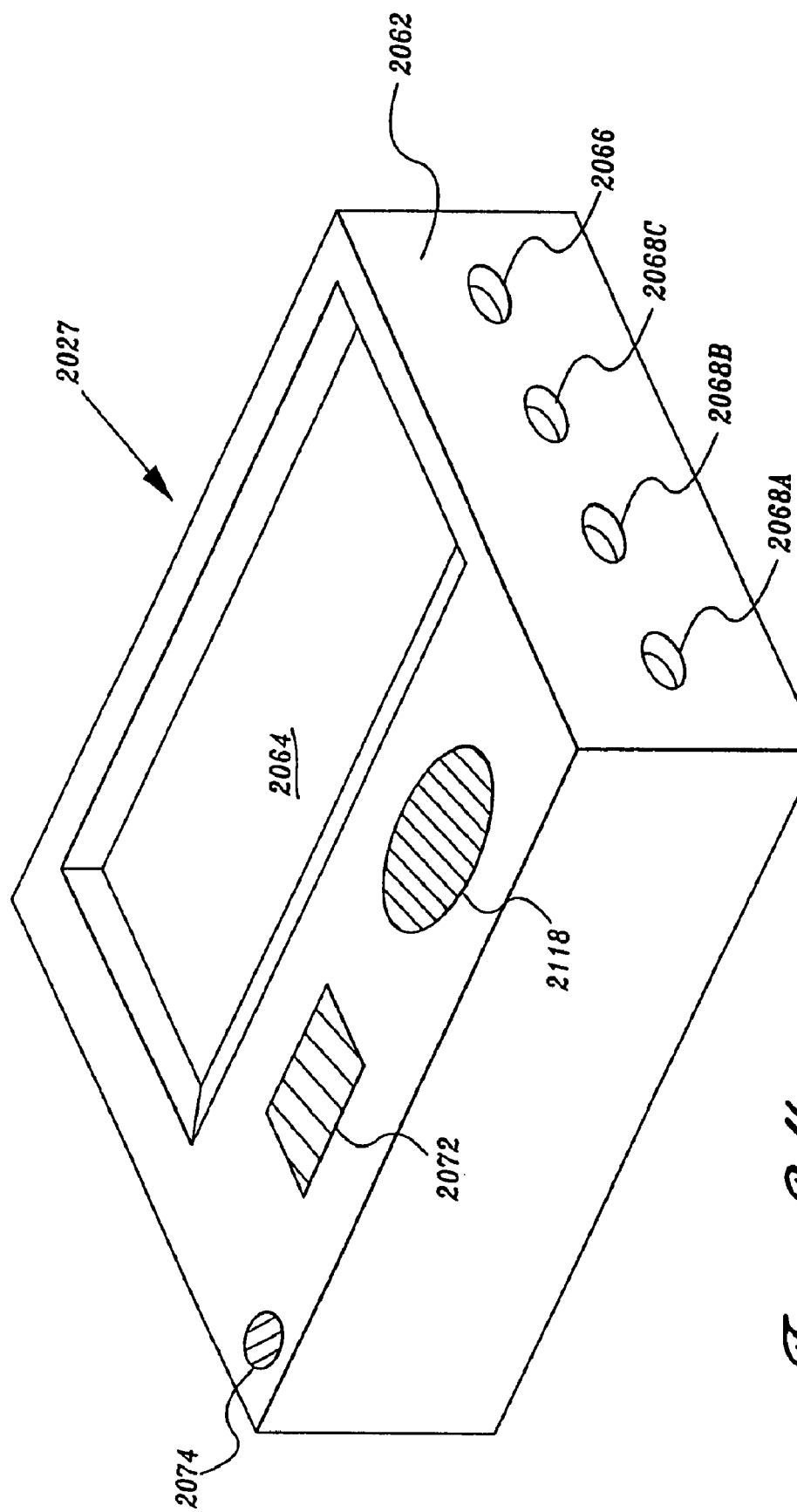

SYSTEM FOR PERFORMING DIABETES SELF-CARE

RELATED APPLICATIONS

This is a continuation of Ser. No. 11/748,113, filed May 14, 2007, which is continuation of Ser. No. 10/826,107, filed Apr. 16, 2004, which is a divisional application of Ser. No. 09/422,046, filed Oct. 20, 1999 now U.S. Pat. No. 7,624,028, which is a continuation of Ser. No. 09/271,217, filed Mar. 17, 1999, now U.S. Pat. No. 6,168,563, which is a continuation in part of Ser. No. 08/481,925, filed Jun. 7, 1995, now U.S. Pat. No. 5,899,855, which is a continuation of U.S. Ser. No. 08/233,397, filed Apr. 26, 1994, now abandoned, each of which is incorporated herein by reference.

FIELD OF THE INVENTION

The present invention relates to remote health monitoring and maintenance system that enables a bi-directional interaction between a patient and a health care provider regarding a health care condition associated with the patient, the bi-directional interaction employing a health care provider apparatus and a remotely programmable patient apparatus.

BACKGROUND OF THE INVENTION

Controlling or curing conditions of ill health generally involves both establishing a therapeutic program and monitoring the progress of the afflicted person. Based on that progress, decisions can be made as to altering therapy to achieve a cure or maintain the affliction or condition at a controlled level. Successfully treating certain health conditions calls for rather frequent monitoring and a relatively high degree of patient participation. For example, in order to establish and maintain a regimen for successful diabetes care, a diabetic should monitor his or her blood glucose level and record that information along with the date and time at which the monitoring took place. Since diet, exercise, and medication all affect blood glucose levels, a diabetic often must record data relating to those items of information along with blood glucose level so that the diabetic may more closely monitor his or her condition and, in addition, can provide information of value to the healthcare provider in determining both progress of the patient and detecting any need to change the patient's therapy program.

Advances in the field of electronics over the past several years have brought about significant changes in medical diagnostic and monitoring equipment, including arrangements for self-care monitoring of various chronic conditions. With respect to the control and monitoring of diabetes, relatively inexpensive and relatively easy-to-use blood glucose monitoring systems have become available that provide reliable information that allows a diabetic and his or her healthcare professional to establish, monitor and adjust a treatment plan (diet, exercise, and medication). More specifically, microprocessor-based blood glucose monitoring systems are being marketed which sense the glucose level of a blood sample that is applied to a reagent-impregnated region of a test strip that is inserted in the glucose monitor. When the monitoring sequence is complete, the blood glucose level is displayed by, for example, a liquid crystal display (LCD) unit.

Typically, currently available self-care blood glucose monitoring units include a calendar/clock circuit and a memory circuit that allows a number of blood glucose test results to be stored along with the date and time at which the monitoring occurred. The stored test results (blood glucose level and associated time and date) can be sequentially recalled for review by the blood glucose monitor user or a health professional by sequentially actuating a push button or other control provided on the monitor. In some commercially available devices, the average of the blood glucose results that are stored in the monitor (or the average of the results for a predetermined period of time, e.g., fourteen days) also is displayed during the recall sequence. Further, some self-care blood glucose monitors allow the user to tag the test result with an "event code" that can be used to organize the test results into categories. For example, a user might use a specific event code to identify test results obtained at particular times of the day, a different event code to identify a blood glucose reading obtained after a period of exercise, two additional event codes to identify blood glucose readings taken during hypoglycemia symptoms and hyperglycemia symptoms, etc. When event codes are provided and used, the event code typically is displayed with each recalled blood glucose test result.

Microprocessor-based blood glucose monitoring systems have advantages other than the capability of obtaining reliable blood glucose test results and storing a number of the results for later recall and review. By using low power microprocessor and memory circuits and powering the units with small, high capacity batteries (e.g., a single alkaline battery), extremely compact and light designs have been achieved that allow taking the blood glucose monitoring system to work, school, or anywhere else the user might go with people encountered by the user not becoming aware of the monitoring system. In addition, most microprocessor-based self-care blood glucose monitoring systems have a memory capacity that allows the system to be programmed by the manufacturer so that the monitor displays a sequence of instructions during any necessary calibration or system tests and during the blood glucose test sequence itself. In addition, the system monitors various system conditions during a blood glucose test (e.g., whether a test strip is properly inserted in the monitor and whether a sufficient amount of blood has been applied to the reagent impregnated portion of the strip) and if an error is detected generates an appropriate display (e.g., "retest"). A data port may be provided that allows test results stored in the memory of the microprocessor-based blood glucose monitoring system to be transferred to a data port (e.g., RS-232 connection) of a personal computer or other such device for subsequent analysis.

Microprocessor-based blood glucose monitoring systems are a significant advance over previously available self-care systems such as those requiring a diabetic to apply a blood sample to reagent activated portions of a test strip; wipe the blood sample from the test strip after a predetermined period of time; and, after a second predetermined period of time, determine blood glucose level by comparing the color of the reagent activated regions of the test strip with a color chart supplied by the test strip manufacturer. Despite what has been achieved, numerous drawbacks and disadvantages still exist. For example, establishing and maintaining diabetic healthcare often requires the diabetic to record additional data pertaining to medication, food intake, and exercise. However, the event codes of currently available microprocessor blood glucose monitoring systems provide only limited capability for tagging and tracking blood glucose test results according to food intake and other relevant factors. For example, the event codes of currently available monitoring systems only allow the user to classify stored blood glucose readings in a manner that indicates blood glucose tests taken immediately after a heavy, light or normal meal. This method of recording information not only requires subjective judgment by the system user, but will not suffice in a situation in which successfully controlling the user's diabetes requires the recording and tracking of relatively accurate information relating to food intake, exercise, or medication (e.g., insulin dosage). An otherwise significant advantage of currently available blood glucose monitoring systems is lost when blood glucose test results must be recorded and tracked with quantitative information relating to medication, food intake, or exercise. Specifically, the system user must record the required information along with a time and date tagged blood glucose test result by, for example, writing the information in a log book.

The use of event codes to establish subcategories of blood glucose test results has an additional disadvantage or drawback. In particular, although alphanumeric display devices are typically used in currently available microprocessor-based blood glucose monitoring systems, the display units are limited to a single line of information having on the order of six characters. Moreover, since the systems include no provision for the user to enter alphanumeric information, any event codes that are used must be indicated on the display in a generic manner, e.g., displayed as "EVENT 1", "EVENT 2", etc. This limitation makes the system more difficult to use because the diabetic must either memorize his or her assignment of event codes or maintain a list that defines the event codes. The limited amount of data that can be displayed at any one time presents additional drawbacks and disadvantages. First, instructions and diagnostics that are displayed to the user when calibrating the system and using the system to obtain a blood glucose reading must be displayed a line at a time and in many cases, the information must be displayed in a cryptic manner.

The above-discussed display limitations and other aspects of currently available blood glucose monitoring systems is disadvantageous in yet another way. Little statistical information can be made available to the user. For example, in diabetic healthcare maintenance, changes or fluctuations that occur in blood glucose levels during a day, a week, or longer period can provide valuable information to a diabetic and/or his or her healthcare professional. As previously mentioned, currently available systems do not allow associating blood glucose test results with attendant quantitative information relating to medication, food intake, or other factors such as exercise that affect a person's blood glucose level at any particular point in time. Thus, currently available blood glucose monitoring systems have little or no capability for the generating and display of trend information that may be of significant value to a diabetic or the diabetic's healthcare professional.

Some currently available blood glucose monitoring systems provide a data port that can be interconnected with and transfer data to a personal computer (e.g., via an RS-232 connection). With such a system and a suitable programmed computer, the user can generate and display trend information or other data that may be useful in administering his or her treatment plan. Moreover, in such systems, data also can be transferred from the blood glucose monitoring system to a healthcare professional's computer either directly or remotely by telephone if both the blood glucose monitoring system (or computer) to which the data has been downloaded and the healthcare professional's computer are equipped with modems. Although such a data transfer provision allows a healthcare professional to analyze blood glucose data collected by a diabetic, this aspect of currently available blood glucose monitoring systems has not found widespread application. First, the downloading and subsequent analysis feature can only be used by system users that have ready access to a computer that is programmed with appropriate software and, in addition, have both the knowledge required to use the software (and the inclination to do so). This same problem exists with respect to data transfer to (and subsequent analysis by) a healthcare professional. Moreover, various manufacturers of systems that currently provide a data transfer feature do not use the same data format. Therefore, if a healthcare professional wishes to analyze data supplied by a number of different blood glucose monitoring systems, he or she must possess software for each of the systems and must learn to conduct the desired analyses with each software system.

The above-discussed disadvantages and drawbacks of microprocessor-based self-care health monitoring systems take on even greater significance with respect to children afflicted with diabetes, asthma and other chronic illnesses. In particular, a child's need for medication and other therapy changes as the child grows. Current microprocessor-based self-care health monitoring systems generally do not provide information that is timely and complete enough for a healthcare professional to recognize and avert problems before relatively severe symptoms develop. Too often, a need for a change in medication and/or other changes in therapeutic regimen is not detected until the child's condition worsens to the point that emergency room care is required.

Further, currently available microprocessor-based health monitoring systems have not been designed with children in mind. As previously mentioned, such devices are not configured for sufficient ease of use in situations in which it is desirable or necessary to record and track quantitative information that affects the physical condition of the system user (e.g., medication dosage administered by a diabetic and food intake). Children above the age at which they are generally capable of obtaining blood samples and administering insulin or other medication generally can learn to use at least the basic blood glucose monitoring features of currently available microprocessor-based blood glucose monitoring systems. However, the currently available monitoring systems provide nothing in the way of motivation for a child to use the device and, in addition, include little or nothing that educates the child about his or her condition or treatment progress.

The lack of provision for the entering of alphanumeric data also can be a disadvantage. For example, currently available blood glucose monitoring systems do not allow the user or the healthcare professional to enter information into the system such as medication dosage and other instructions or data that is relevant to the user's self-care health program.

The above-discussed disadvantages and drawbacks of currently available microprocessor-based blood glucose monitoring systems also have been impediments to adopting the basic technology of the system for other healthcare situations in which establishing and maintaining an effective regimen for cure or control is dependent upon (or at least facilitated by) periodically monitoring a condition and recording that condition along with time and date tags and other information necessary or helpful in establishing and maintaining a healthcare program.

In the United States alone, over 100 million people have chronic health conditions, accounting for an estimated $700 billion in annual medical costs. In an effort to control these medical costs, many healthcare providers have initiated outpatient or home healthcare programs for their patients. The potential benefits of these programs are particularly great for chronically ill patients who must treat their diseases on a daily basis. However, the success of these programs is dependent upon the ability of the healthcare providers to monitor the patients remotely to avert medical problems before they become complicated and costly. Unfortunately, no convenient and cost effective monitoring system exists for the patients who have the greatest need for monitoring, the poor and the elderly.

Prior attempts to monitor patients remotely have included the use of personal computers and modems to establish communication between patients and healthcare providers. However, computers are too expensive to give away and the patients who already own computers are only a small fraction of the total population. Further, the patients who own computers are typically young, well educated, and have good healthcare coverage. Thus, these patients do not have the greatest unmet medical needs. The patients who have the greatest unmet medical needs are the poor and elderly who do not own computers or who are unfamiliar with their use.

Similar attempts to establish communication between patients and healthcare providers have included the use of the Internet and internet terminals. Although internet terminals are somewhat less costly than personal computers, they are still too expensive to give away to patients. Moreover, monthly on-line access charges are prohibitive for poor patients.

Other attempts to monitor patients remotely have included the use of medical monitoring devices with built-in modems. Examples of such monitoring devices include blood glucose meters, respiratory flow meters, and heart rate monitors. Unfortunately, these monitoring devices are only designed to collect physiological data from the patients. They do not allow flexible and dynamic querying of the patients for other information, such as quality of life measures or psycho-social variables of illness.

Prior attempts to monitor patients remotely have also included the use of interactive telephone or video response systems. Such interactive systems are disclosed in U.S. Pat. No. 5,390,238 issued to Kirk et al. on Feb. 14, 1995, U.S. Pat. No. 5,434,611 issued to Tamura on Jul. 18, 1995, and U.S. Pat. No. 5,441,047 issued to David et al. on Aug. 15, 1995. One disadvantage of these systems is that they either require a patient to call in to a central facility to be monitored or require the central facility to call the patient according to a rigid monitoring schedule.

If the patients are required to call the central facility, only the compliant patients will actually call regularly to be monitored. Non-compliant patients will typically wait until an emergency situation develops before contacting their healthcare provider, thus defeating the purpose of the monitoring system. If the central facility calls each patient according to a monitoring schedule, it is intrusive to the patient's life and resistance to the monitoring grows over time.

Another disadvantage of these conventional interactive response systems is that they are prohibitively expensive for poor patients. Further, it is difficult to identify each patient uniquely using these systems. Moreover, these systems are generally incapable of collecting medical data from monitoring devices, such as blood glucose meters, respiratory flow meters, or heart rate monitors.

OBJECTS AND ADVANTAGES OF THE INVENTION

In view of the above, it is an object of the present invention to provide a simple and inexpensive system for remotely monitoring patients and for communicating information to the patients. It is another object of the invention to provide a system which allows flexible and dynamic querying of the patients. It is a further object of the invention to provide a system which combines querying of patients with medical device monitoring in the same monitoring session. Another object of the invention is to provide a monitoring system which incurs lower communications charges than those incurred by conventional monitoring systems. A further object of the invention is to provide a monitoring system which may be used at any time convenient for a patient.

These and other objects and advantages will become more apparent after consideration of the ensuing description and the accompanying drawings.

SUMMARY OF THE INVENTION

This invention provides a new and useful system for healthcare maintenance in which the invention either serves as a peripheral device to (or incorporates) a small handheld microprocessor-based unit of the type that includes a display screen, buttons or keys that allow a user to control the operation of the device and a program cartridge or other arrangement that can be inserted in the device to adapt the device to a particular application or function. The invention in effect converts the handheld microprocessor device into a healthcare monitoring system that has significant advantages over systems such as the currently available blood glucose monitoring systems. To perform this conversion, the invention includes a microprocessor-based healthcare data management unit, a program cartridge and a monitoring unit. When inserted in the handheld microprocessor unit, the program cartridge provides the software necessary (program instructions) to program the handheld microprocessor unit for operation with the microprocessor-based data management unit. Signal communication between the data management unit and the handheld microprocessor unit is established by an interface cable. A second interface cable can be used to establish signal communication between the data management unit and the monitoring unit or, alternatively, the monitoring unit can be constructed as a plug-in unit having an electrical connector that mates with a connector mounted within a region that is configured for receiving the monitoring unit.

In operation, the control buttons or keys of the handheld microprocessor-based unit are used to select the operating mode for both the data management unit and the handheld microprocessor-based unit. In response to signals generated by the control buttons or keys, the data management unit generates signals that are coupled to the handheld microprocessor unit and, under control of the program instructions contained in the program cartridge, establish an appropriate screen display on the handheld microprocessor-based unit display. In selecting system operating mode and other operations, the control buttons are used to position a cursor or other indicator in a manner that allows the system user to easily select a desired operating mode or function and provide any other required operator input. In the disclosed detailed embodiment of the invention several modes of operation are made available.

In the currently preferred embodiments of the invention, the handheld microprocessor unit is a compact video game system such as the system manufactured by Nintendo of America Inc. under the trademark "GAME BOY." Use of a compact video game system has several general advantages, including the widespread availability and low cost of such systems. Further, such systems include switch arrangements that are easily adapted for use in the invention and the display units of such systems are of a size and resolution that can advantageously be employed in the practice of the invention. In addition, such systems allow educational or motivational material to be displayed to the system user, with the material being included in the program cartridge that provides the monitor system software or, alternatively, in a separate program cartridge.

The use of a compact video game system for the handheld microprocessor-based unit of the invention is especially advantageous with respect to children. Specifically, the compact video game systems of the type that can be employed in the practice of the invention are well known and well accepted by children. Such devices are easily operated by a child and most children are well accustomed to using the devices in the context of playing video games. Motivational and educational material relating to the use of the invention can be presented in game-like or animated format to further enhance acceptance and use of the invention by children that require self-care health monitoring.

A microprocessor-based health monitoring system that is configured in accordance with the invention provides additional advantages for both the user and a healthcare professional. In accordance with one aspect of the invention, standardized reports are provided to a physician or other healthcare provider by means of facsimile transmission. To accomplish this, the data management unit of the currently preferred embodiments of the invention include a modem which allows test results and other data stored in system memory to be transmitted to a remote clearinghouse via a telephone collection. Data processing arrangements included in the clearinghouse perform any required additional data processing; format the standardized reports; and, transmit the reports to the facsimile machine of the appropriate healthcare professional.

The clearinghouse also can fill an additional communication need, allowing information such as changes in medication dosage or other information such as modification in the user's monitoring schedule to be electronically sent to a system user. In arrangements that incorporate this particular aspect of the invention, information can be sent to the user via a telephone connection and the data management unit modem when a specific inquiry is initiated by the user, or when the user establishes a telephone connection with the clearinghouse for other purposes such as providing data for standardized reports.

The clearinghouse-facsimile aspect of the invention is important because it allows a healthcare professional to receive timely information about patient condition and progress without requiring a visit by the patient (system user) and without requiring analysis or processing of test data by the healthcare professional. In this regard, the healthcare professional need not possess or even know how to use a computer and/or the software conventionally employed for analysis of blood glucose and other health monitoring data and information.

The invention also includes provision for data analysis and memory storage of information provided by the user and/or the healthcare professional. In particular, the data management units of the currently preferred embodiments of the invention include a data port such as an RS-232 connection that allows the system user or healthcare professional to establish signal communication between the data management unit and a personal computer or other data processing arrangement. Blood glucose test data or other information can then be downloaded for analysis and record keeping purposes. Alternatively, information such as changes in the user's treatment and monitoring regimen can be entered into system memory. Moreover, if desired, remote communication between the data management unit and the healthcare professional's computer can be established using the clearinghouse as an element of the communications link. That is, in the currently preferred arrangements of the invention a healthcare professional has the option of using a personal computer that communicates with the clearinghouse via a modem and telephone line for purposes of transmitting instructions and information to a selected user of the system and/or obtaining user test data and information for subsequent analysis.

The invention can be embodied in forms other than those described above. For example, although small handheld microprocessor-based units such as a handheld video game system or handheld microprocessor-based units of the type often referred to as "palm-top" computers provide many advantages, there are situations in which other compact microprocessor-based units can advantageously be used. Among the various types of units that can be employed are using compact video game systems of the type that employ a program cartridge, but uses a television set or video monitor instead of a display unit that is integrated into the previously described handheld microprocessor-based units.

Those skilled in the art also will recognize that the above-described microprocessor-implemented functions and operations can be apportioned between one or more microprocessors in a manner that differs from the above-described arrangement. For example, in some situations, the programmable microprocessor-based unit and the program cartridge used in practicing the invention may provide memory and signal processing capability that is sufficient for practicing the invention. In such situations, the microprocessor of the microprocessor-based data management unit of the above-described embodiments in effect is moved into the video game system, palm-top, computer or programmable microprocessor device. In such an arrangement, the data management unit can be realized as a relatively simple interface unit that includes little or no signal processing capability. Depending upon the situation at hand, the interface unit may or may not include a telephone modem and/or an RS-232 connection (or other data port) for interconnecting the healthcare system with a computer or other equipment. In other situations, the functions and operations associated with processing of the monitored health care data may be performed by a microprocessor that is added to or already present in the monitoring device that is used to monitor blood glucose or other condition.

Because the invention can be embodied to establish systems having different levels of complexity, the invention satisfies a wide range of self-care health monitoring applications. The arrangements that include a modem (or other signal transmission facility) and sufficient signal processing capability can be employed in situations in which reports are electronically transmitted to a healthcare professional either in hard copy (facsimile) form or in a signal format that can be received by and stored in the healthcare professional's computer. On the other hand, less complex (and, hence, less costly) embodiments of the invention are available for use in which transfer of system information need not be made by means of telephonic data transfer or other remote transmission methods. In these less complex embodiments, transfer of data to a healthcare professional can still be accomplished. Specifically, if the program cartridge includes a battery and suitable program instructions, monitored healthcare data can be stored in the program cartridge during use of the system as a healthcare monitor. The data cartridge can then be provided to the healthcare professional and inserted in a programmable microprocessor-based unit that is the same as or similar to that which was used in the healthcare monitoring system. The healthcare professional can then review the data, and record it for later use, and/or can use the data in performing various analyses. If desired, the microprocessor-based unit used by the healthcare professional can be programmed and arranged to allow information to be stored in the cartridge for return to and retrieval by the user of the healthcare monitoring system. The stored information can include messages (e.g., instructions for changes in medication dosage) and/or program instructions for reconfiguring the program included in the cartridge so as to effect changes in the treatment regimen, the analyses or reports to be generated by the healthcare monitoring system, or less important aspects such as graphical presentation presented during the operation of the healthcare system.

The invention presents a networked system for remotely monitoring an individual and for communicating information to the individual. The system includes a server and a remote interface for entering in the server a set of queries to be answered by the individual. The server is preferably a world wide web server and the remote interface is preferably a personal computer or network terminal connected to the web server via the Internet. The system also includes a remotely programmable apparatus for interacting with the individual. The apparatus is connected to the server via a communication network, preferably the Internet. The apparatus interacts with the individual in accordance with a script program received from the server.

The server includes a script generator for generating the script program from the queries entered through the remote interface. The script program is executable by the apparatus to communicate the queries to the individual, to receive responses to the queries, and to transmit the responses from the apparatus to the server. The server also includes a database connected to the script generator for storing the script program and the responses to the queries.

The apparatus has a communication device, such as a modem, for receiving the script program from the server and for transmitting the responses to the server. The apparatus also has a user interface for communicating the queries to the individual and for receiving the responses to the queries. In the preferred embodiment, the user interface includes a display for displaying the queries and user input buttons for entering the responses to the queries. In an alternative embodiment, the user interface includes a speech synthesizer for audibly communicating the queries and a speech recognizer for receiving spoken responses to the queries.

The apparatus also includes a memory for storing the script program and the responses to the queries. The apparatus further includes a microprocessor connected to the communication device, the user interface, and the memory. The microprocessor executes the script program to communicate the queries to the individual, to receive the responses to the queries, and to transmit the responses to the server through the communication network.

In the preferred embodiment, the system also includes at least one monitoring device for producing measurements of a physiological condition of the individual and for transmitting the measurements to the apparatus. The apparatus further includes a device interface connected to the microprocessor for receiving the measurements from the monitoring device. The measurements are stored in the memory and transmitted to the server with the responses to the queries. The server also preferably includes a report generator connected to the database for generating a report of the measurements and responses. The report is displayed on the remote interface.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 16 is a script entry screen according to the preferred embodiment of the invention;

FIG. 17A is a listing of a sample script program according to the preferred embodiment of the invention;

FIG. 17B is a continuation of the listing of FIG. 17A;

FIG. 21 is a sample report displayed on a workstation of the system of FIG. 12;

FIG. 24 is a perspective view of a remotely programmable apparatus according to a second embodiment of the invention;

DETAILED DESCRIPTION

Figure 1:
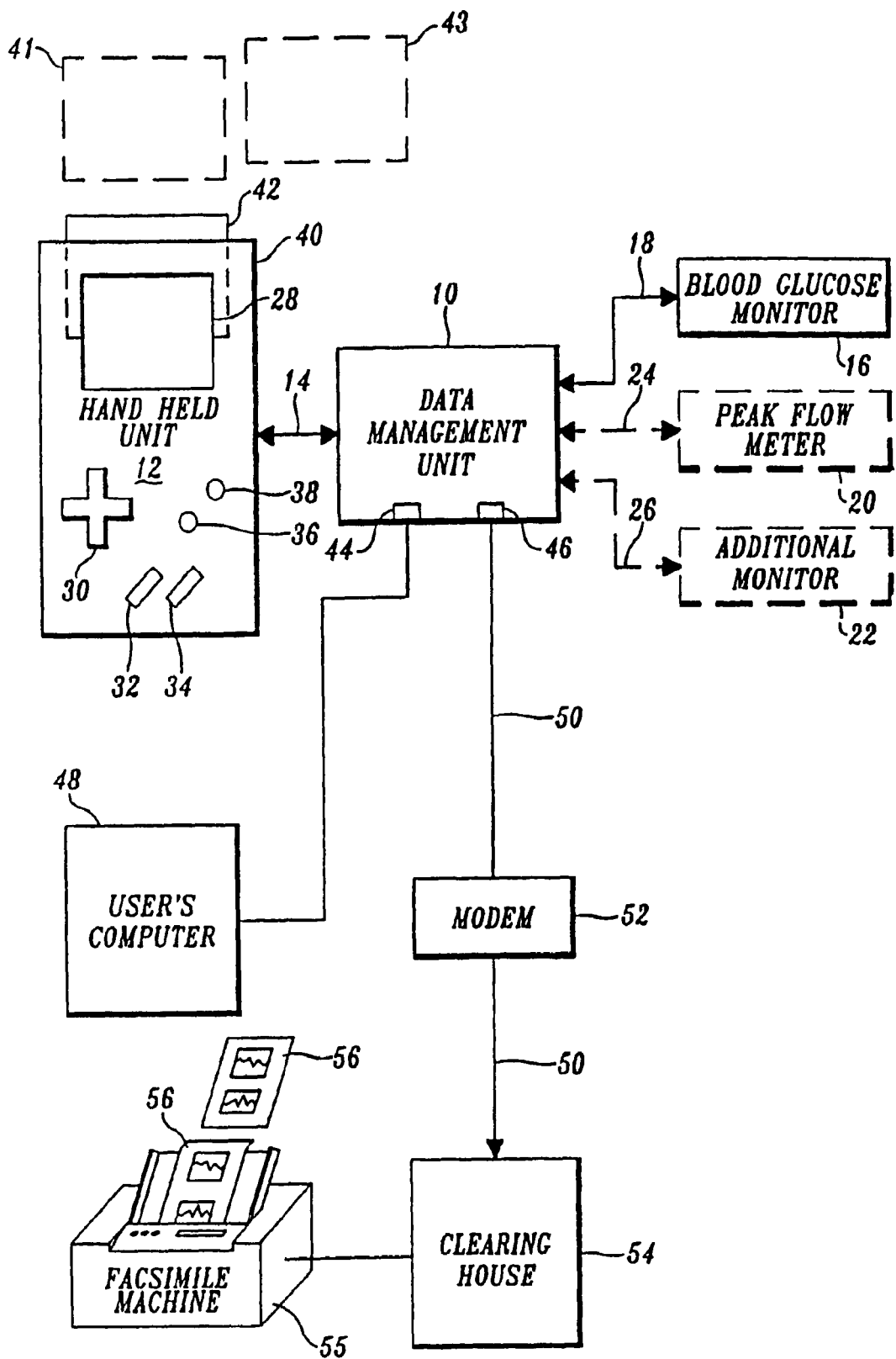
FIG. 1 is a block diagram that illustrates a healthcare monitoring system arranged in accordance with the invention.

FIG. 1 depicts a self-care health monitoring system arranged in accordance with the invention. In the arrangement shown in FIG. 1, a data management unit 10 is electrically interconnected with a handheld microprocessor-based unit 12 via a cable 14. In the depicted arrangement, data management unit 10 also is electrically interconnected with a blood glucose monitor 16 of the type capable of sensing blood glucose level and producing an electrical signal representative thereof. Although FIG. 1 illustrates blood glucose monitor 16 as being connected to data management unit 10 by a cable 18, it may be preferable to construct blood glucose monitor 16 as a plug-in unit that is placed in a recess or other suitable opening or slot in data management unit 10. Regardless of the manner in which blood glucose monitor 16 is interconnected with data management unit 10, both that interconnection and cable 14 are configured for serial data communication between the interconnected devices.

Also shown in FIG. 1 are two additional monitoring devices 20 and 22, which are electrically connected for serial data communication with data management unit 10 via cables 24 and 26, respectively. Monitoring units 20 and 22 of FIG. 1 represent devices other than blood glucose monitor 16 that can be used to configure the invention for self-care health monitoring applications other than (or in addition to) diabetes care. For example, as is indicated in FIG. 1, the monitoring device 20 can be a peak-flow meter that provides a digital signal representative of the airflow that results when a person suffering from asthma or another chronic respiratory affliction expels a breath of air through the meter. As is indicated by monitor 22 of FIG. 1, various other devices can be provided for monitoring conditions such as blood pressure, pulse, and body temperature to thereby realize systems for self-care monitoring and control of conditions such as hypertension, certain heart conditions and various other afflictions and physical conditions. Upon understanding the hereinafter discussed aspects and features of the invention it will be recognized that the invention is easily implemented for these and other types of healthcare monitoring. In particular, monitors used in the practice of the invention can be arranged in a variety of ways as long as the data to be recorded or otherwise employed by handheld microprocessor unit 12 and/or data management unit 10 is provided in serial format in synchronization with clock signals provided by data management unit 10. As is the case with blood glucose monitor 16, the additional monitors can be configured as plug-in units that are directly received by data management unit 10, or can be connected to data management unit 10 with cables (as shown in FIG. 1).

As is shown in FIG. 1, handheld microprocessor unit 12 includes a display screen 28 and a plurality of switches or keys (30, 32, 34, 36, and 38 in FIG. 1), which are mounted on a housing 40. Located in the interior of housing 40, but not shown in FIG. 1, are a microprocessor, memory circuits, and circuitry that interfaces switches 30, 32, 34, 36 and 38 with the microprocessor. Stored in the memory of program handheld microprocessor unit 12 is a set of program instructions that establishes a data protocol that allows handheld microprocessor unit 12 to perform digital data signal processing and generate desired data or graphics for display on display unit 28 when a program cartridge 42 is inserted in a slot or other receptacle in housing 40. That is, program cartridge 42 of FIG. 1 includes read-only memory units (or other memory means such as battery-powered random access memory) which store program instructions and data that adapt handheld microprocessor 12 for operation in a blood glucose monitoring system. More specifically, when the instructions and data of program cartridge 42 are combined with program instructions and data included in the internal memory circuits of handheld microprocessor unit 12, handheld microprocessor unit 12 is programmed for processing and displaying blood glucose information in the manner described below and additional monitors 22 to provide health monitoring for asthma and various other previously mentioned chronic conditions. In each case, the plurality of switches or keys (30, 32, 34, 36, and 38 in FIG. 1) are selectively operated to provide signals that result in pictorial and/or alphanumeric information being displayed by display unit 42.

Various devices are known that meet the above-set forth description of handheld microprocessor unit 12. For example, compact devices are available in which the plurality of keys allows alphanumeric entry and internal memory is provided for storing information such as names, addresses, phone numbers, and an appointment calendar. Small program cartridges or cards can be inserted in these devices to program the device for various purposes such as the playing of games, spreadsheet application, and foreign language translation sufficient for use in travel. More recently, less compact products that have more extensive computational capability and are generally called "palm top computers" have been introduced into the marketplace. These devices also can include provision for programming the device by means of an insertable program card or cartridge.

The currently preferred embodiments of the invention are configured and arranged to operate in conjunction with yet another type of handheld microprocessor unit. Specifically, in the currently preferred embodiments of the invention, program cartridge 42 is electrically and physically compatible with commercially available compact video game systems, such as the system manufactured by Nintendo of America Inc. under the trademark "GAME BOY." Configuring data management unit 10 and program cartridge 42 for operation with a handheld video game system has several advantages. For example, the display unit of such a device provides display resolution that allows the invention to display both multi-line alphanumeric information and graphical data. In this regard, the 160×144 pixel dot matrix-type liquid crystal display screen currently used in the above-referenced compact video game systems provides sufficient resolution for at least six lines of alphanumeric text, as well as allowing graphical representation of statistical data such as graphical representation of blood glucose test results for a day, a week, or longer.

Another advantage of realizing handheld microprocessor unit 12 in the form of a compact video game system is the relatively simple, yet versatile arrangement of switches that is provided by such a device. For example, as is indicated in FIG. 1, a compact video game system includes a control pad 30 that allows an object displayed on display unit 42 to be moved in a selected direction (i.e., up-down or left-right). As also is indicated in FIG. 1, compact video game systems typically provide two pair of distinctly-shaped push button switches. In the arrangement shown in FIG. 1, a pair of spaced-apart circular push button switches (36 and 38) and a pair of elongate switches (32 and 34) are provided. The functions performed by the two pairs of switches is dependent upon the program instructions contained in each program cartridge 42.

Yet another advantage of utilizing a compact video game system for handheld microprocessor-based unit 12 of FIG. 1 is the widespread popularity and low cost of such units. In this regard, manufacture and sale of a data management unit 10, blood glucose monitor 16 and program cartridge 42 that operate in conjunction with a compact microprocessor-based video allows the self-care health monitoring system of FIG. 1 to be manufactured and sold at a lower cost than could be realized in an arrangement in which handheld unit 12 is designed and manufactured solely for use in the system of FIG. 1.

An even further advantage of using a compact video game system for handheld microprocessor 12 is that such video game systems include means for easily establishing the electrical interconnection provided by cable 14 in FIG. 1. In particular, such compact video game systems include a connector mounted to the game unit housing (40 in FIG. 1) and a cable that can be connected between the connectors of two video game units to allow interactive operation of the two interconnected units (i.e., to allow contemporaneous game play by two players or competition between players as they individually play identical but separate games). In the preferred embodiments of the invention, the "two-player" cable supplied with the compact video game unit being used as handheld microprocessor unit 12 is used as cable 14 to establish serial data communication between the handheld microprocessor unit 12 (compact video game system) and data management unit 10. In these preferred embodiments, the program instructions stored on the memory of data management unit 10 and program cartridge 42 respectively program data management unit 10 and the compact video game system (i.e., handheld microprocessor unit 12) for interactive operation in which switches 30, 32, 34, 36 and 38 are used to control the operation of data management unit 10 (e.g., to select a particular operational mode such as performance of a blood glucose test or the display of statistical test data and, in addition, to control operation such as selection of an option during operation of the system in a particular operational mode). In each operational mode, data management unit 10 processes data in accordance with program instructions stored in the memory circuits of data management unit 10. Depending upon the operational mode selected by the user, data is supplied to data management unit 10 by blood glucose monitor 16, by additional monitors (20 and 22 in FIG. 1) or any interconnected computers or data processing facility (such as the hereinafter described user's computer 48 and clearinghouse 54 of FIG. 1). During such operation, mode switches 30, 32, 34, 36 and 38 are selectively activated so that signals are selectively coupled to the video game system (handheld microprocessor unit 12) and processed in accordance with program instructions stored in program cartridge 42. The signal processing performed by handheld microprocessor unit 12 results in the display of alphanumeric, symbolic, or graphic information on the video game display screen (i.e., display unit 28 in FIG. 1), which allow the user to control system operation and obtain desired test results and other information.

Although the above-discussed advantages apply to use of the invention by all age groups, employing a compact video game system in the practice of the invention is of special significance in monitoring a child's blood glucose or other health parameters. Children and young adults are familiar with compact video game systems. Thus, children will accept a health monitoring system incorporating a compact video game system more readily than a traditional system, even an embodiment of the invention that uses a different type of handheld microprocessor unit. Moreover, an embodiment of the invention that functions in conjunction with a compact video game system can be arranged to motivate children to monitor themselves more closely than they might otherwise by incorporating game-like features and/or animation in system instruction and test result displays. Similarly, the program instructions can be included in program cartridges 41, 42 and 43 (or additional cartridges) that allow children to select game-like displays that help educate the child about his or her condition and the need for monitoring.

With continued reference to FIG. 1, data management unit 10 of the currently preferred embodiments of the invention includes a data port 44 that allows communication between data management unit 10 and a personal computer 48 (or other programmable data processor). In the currently preferred embodiments of the invention, data port 44 is an RS-232 connection that allows serial data communication between data management unit 10 and personal computer 48. In the practice of the invention, personal computer 48 can be used to supplement data management unit 10 by, for example, performing more complex analyses of blood glucose and other data that has been supplied to and stored in the memory circuits of data management unit 10. With respect to embodiments of the invention configured for use by a child, personal computer 48 can be used by a parent or guardian to review and analyze the child's progress and to produce printed records for subsequent review by a healthcare professional. Alternatively, personal computer 48 can be used to supply data to data management unit 10 that is not conveniently supplied by using handheld microprocessor switches 30, 32, 34, 36 and 38 as an operator interface to the system shown in FIG. 1. For example, some embodiments of the invention may employ a substantial amount of alphanumeric information that must be entered by the system user. Although it is possible to enter such data by using switches 30, 32, 34, 36 and 38 in conjunction with menus and selection screens displayed on display screen 28 of FIG. 1, it may be more advantageous to use a device such as personal computer 48 for entry of such data. However, if personal computer 48 is used in this manner, some trade-off of system features may be required because data management unit 10 must be temporarily interconnected with personal computer 48 during these operations. That is, some loss of system mobility might result because a suitably programmed personal computer would be needed at each location at which data entry or analysis is to occur.

As is indicated in FIG. 1, data management unit 10 of the currently preferred embodiments of the invention also includes a modem that allows data communication between data management unit 10 and a remote computing facility identified in FIG. 1 as clearinghouse 54 via a conventional telephone line (indicated by reference numeral 50 in FIG. 1) and a modem 52 that interconnects clearinghouse 54 and telephone line 50. As shall be described in more detail, clearinghouse computing facility 54 facilitates communication between a user of the system shown in FIG. 1 and his or her healthcare professional and can provide additional services such as updating system software. As is indicated by facsimile machine 55 of FIG. 1, a primary function of clearinghouse 54 is providing the healthcare professional with standardized reports 56, which indicate both the current condition and condition trends of the system user. Although a single facsimile machine 55 is shown in FIG. 1, it will be recognized that numerous healthcare professionals (and hence facsimile machine 55) can be connected in signal communication with a clearinghouse 54.

Regardless of whether a compact video game system, another type of commercially available handheld microprocessor-based unit, or a specially designed unit is used, the preferred embodiments of FIG. 1 provide a self-care blood glucose monitoring system in which program cartridge 42: (a) adapts handheld microprocessor unit 12 for displaying instructions for performing the blood glucose test sequence and associated calibration and test procedures (b) adapts handheld microprocessor unit 12 for displaying (graphically or alphanumerically) statistical data such as blood glucose test results taken during a specific period of time (e.g., a day, week, etc.), (c) adapts handheld microprocessor unit 12 for supplying control signals and signals representative of food intake or other useful information to data management unit 10: (d) adapts handheld microprocessor unit 12 for simultaneous graphical display of blood glucose levels with information such as food intake; and, (e) adapts handheld microprocessor unit 12 for displaying information or instructions from a healthcare professional that are coupled to data management unit 10 from a clearinghouse 54. The manner in which the arrangement of FIG. 1 implements the above-mentioned functions and others can be better understood with reference to FIGS. 2 and 3.

Figure 2:
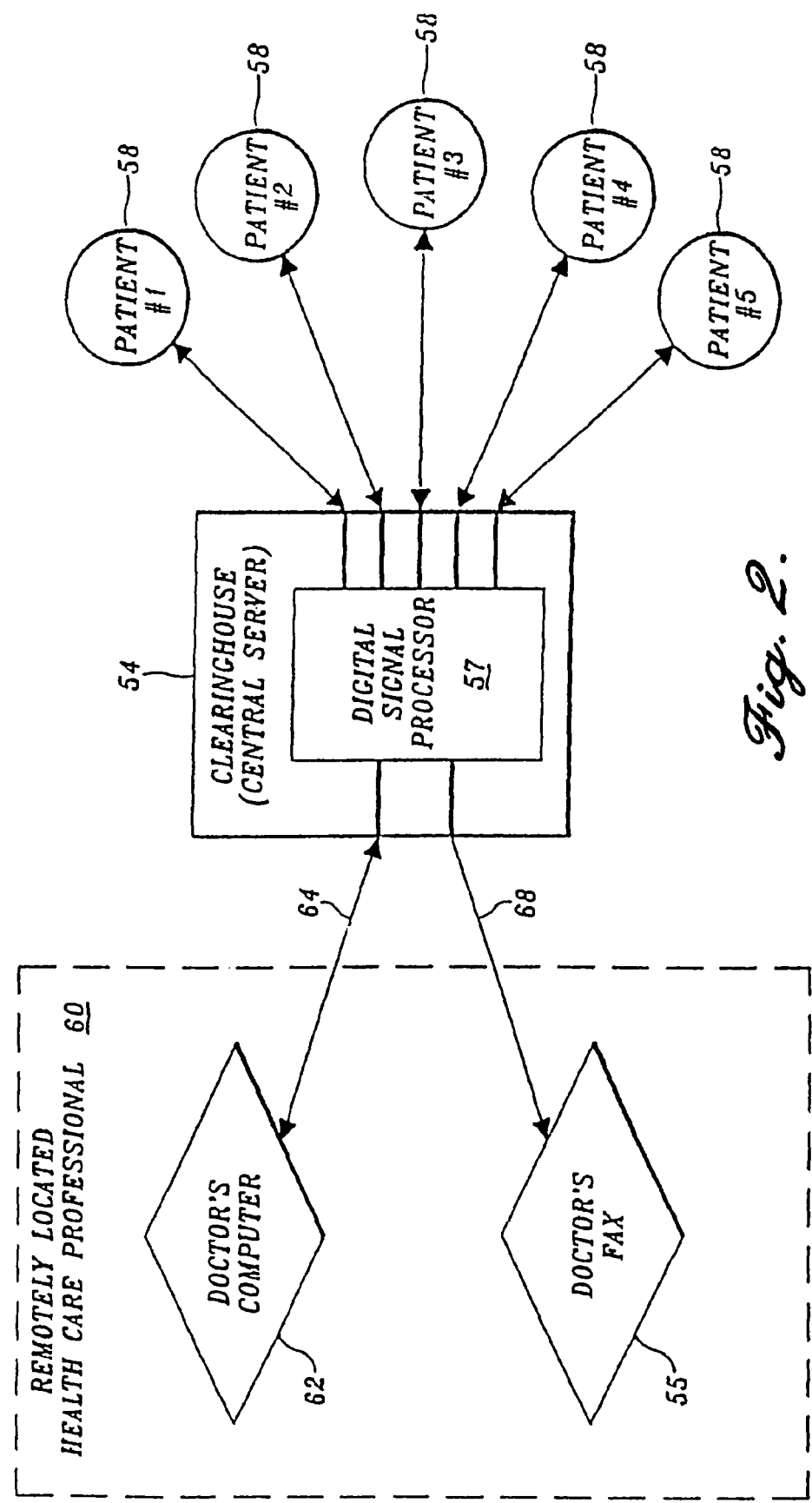
FIG. 2 diagrammatically illustrates monitoring systems constructed in accordance with the invention connected in signal communication with a remotely located computing facility which includes provision for making the data supplied by the monitoring system of the invention available to a designated healthcare professional and/or for providing data and instructions to the system user.

Referring first to FIG. 2, clearinghouse 54 receives data from a plurality of self-care microprocessor-based healthcare systems of the type shown in FIG. 1, with the individual self-care health monitoring systems being indicated in FIG. 2 by reference numeral 58. Preferably, the data supplied to clearinghouse 54 by each individual self-care health monitoring system 58 consists of "raw data," i.e., test results and related data that was stored in memory circuits of data management unit 10, without further processing by data management unit 10. For example, with respect to the arrangement shown in FIG. 1, blood glucose test results and associated data such as food intake information, medication dosage and other such conditions are transmitted to clearinghouse 54 and stored with a digitally encoded signal that identifies both the source of the information (i.e., the system user or patient) and those having access to the stored information (i.e., the system user's doctor or other healthcare professional).

As shall be recognized upon understanding the manner in which it operates, clearinghouse 54 can be considered to be a central server for the various system users (58 in FIG. 2) and each healthcare professional 60. In that regard, clearinghouse 54 includes conventionally arranged and interconnected digital processing equipment (represented in FIG. 2 by digital signal processor 57) which receives digitally encoded information from a user 58 or healthcare professional 60; processes the information as required; stores the information (processed or unprocessed) in memory if necessary; and, transmits the information to an intended recipient (i.e., user 58 or healthcare professional 60).

In FIG. 2, rectangular outline 60 represents one of numerous remotely located healthcare professionals who can utilize clearinghouse 54 and the arrangement described relative to FIG. 1 in monitoring and controlling patient healthcare programs. Shown within outline 60 is a computer 62 (e.g., personal computer), which is coupled to clearinghouse 54 by means of a modem (not shown in FIG. 2) and a telephone line 64. Also shown in FIG. 2 is the previously mentioned facsimile machine 55, which is coupled to clearinghouse 54 by means of a second telephone line 68. Using the interface unit of computer 62 (e.g., a keyboard or pointing device such as a mouse), the healthcare professional can establish data communication between computer 62 and clearinghouse 54 via telephone line 64. Once data communication is established between computer 62 and clearinghouse 54, patient information can be obtained from clearinghouse 54 in a manner similar to the manner in which subscribers to various database services access and obtain information. In particular, the healthcare professional can transmit an authorization code to clearinghouse 54 that identifies the healthcare professional as an authorized user of the clearinghouse and, in addition, can transmit a signal representing the patient for which healthcare information is being sought. As is the case with conventional database services and other arrangements, the identifying data is keyed into computer 62 by means of a conventional keyboard (not shown in FIG. 2) in response to prompts that are generated at clearinghouse 54 for display by the display unit of computer 62 (not shown in FIG. 2).

Depending upon the hardware and software arrangement of clearinghouse 54 and selections made by the healthcare professional via computer 62, patient information can be provided to the healthcare professional in different ways. For example, computer 62 can be operated to access data in the form that it is stored in the memory circuits of clearinghouse 54 (i.e., raw data that has not been processed or altered by the computational or data processing arrangements of clearinghouse 54). Such data can be processed, analyzed, printed and/or displayed by computer 62 using commercially available or custom software. On the other hand, various types of analyses may be performed by clearinghouse 54 with the results of the analyses being transmitted to the remotely located healthcare professional 60. For example, clearinghouse 54 can process and analyze data in a manner identical to the processing and analysis provided by the self-care monitoring system of FIG. 1. With respect to such processing and any other analysis and processing provided by clearinghouse 54, results expressed in alphanumeric format can be sent to computer 62 via telephone line 64 and the modem associated with computer 62, with conventional techniques being used for displaying and/or printing the alphanumeric material for subsequent reference.

The arrangement of FIG. 2 also allows the healthcare professional to send messages and/or instructions to each patient via computer 62, telephone line 64, and clearinghouse 54. In particular, clearinghouse 54 can be programmed to generate a menu that is displayed by computer 62 and allows the healthcare professional to select a mode of operation in which information is to be sent to clearinghouse 54 for subsequent transmission to a user of the system described relative to FIG. 1. This same menu (or related submenus) can be used by the healthcare professional to select one or more modes of operation of the above-described type in which either unmodified patient data or the results of data that has been analyzed by clearinghouse 54 is provided to the healthcare provider via computer 62 and/or facsimile machine 55.

In the currently contemplated arrangements, operation of the arrangement of FIG. 2 to provide the user of the invention with messages or instructions such as changes in medication or other aspects of the healthcare program is similar to the operation that allows the healthcare professional to access data sent by a patient, i.e., transmitted to clearinghouse 54 by a data management unit 10 of FIG. 1. The process differs in that the healthcare professional enters the desired message or instruction via the keyboard or other interface unit of computer 62. Once the data is entered and transmitted to clearinghouse 54, it is stored for subsequent transmission to the user for whom the information or instruction is intended. With respect to transmitting stored messages or instructions to a user of the invention, at least two techniques are available. The first technique is based upon the manner in which operational modes are selected in the practice of the invention. Specifically, in the currently preferred embodiments of the invention, program instructions that are stored in data management unit 10 and program cartridge 42 cause the system of FIG. 1 to generate menu screens which are displayed by display unit 28 of handheld microprocessor unit 12. The menu screens allow the system user to select the basic mode in which the system of FIG. 1 is to operate and, in addition, allow the user to select operational subcategories within the selected mode of operation. Various techniques are known to those skilled in the art for displaying and selecting menu items. For example, in the practice of this invention, one or more main menus can be generated and displayed which allow the system user to select operational modes that may include: (a) a monitor mode (e.g., monitoring of blood glucose level); (b) a display mode (e.g., displaying previously obtained blood glucose test results or other relevant information); (c) an input mode (e.g., a mode for entering data such as providing information that relates to the healthcare regimen, medication dosage, food intake, etc.); and, (d) a communications mode (for establishing a communication link between data management unit 10 and personal computer 48 of FIG. 1; or between data management unit 10 and a remote computing facility such as clearinghouse 54 of FIG. 2).

In embodiments of the invention that employ a compact video game system for handheld microprocessor unit 12, the selection of menu screens and the selection of menu screen items preferably is accomplished in substantially the same manner as menu screens and menu items are selected during the playing of a video game. For example, the program instructions stored in data management unit 10 and program cartridge 42 of the arrangement of FIG. 1 can be established so that a predetermined one of the compact video game switches (e.g., switch 32 in FIG. 1) allows the system user to select a desired main menu in the event that multiple main menus are employed. When the desired main menu is displayed, operation by the user of control pad 30 allows a cursor or other indicator that is displayed on the menu to be positioned adjacent to or over the menu item to be selected. Activation of a switch (e.g., switch 36 of the depicted handheld microprocessor unit 12) causes the handheld microprocessor unit 12 and/or data management unit 10 to initiate the selected operational mode or, if selection of operational submodes is required, causes handheld microprocessor unit 12 to display a submenu.

In view of the above-described manner in which menus and submenus are selected and displayed, it can be recognized that the arrangement of FIG. 1 can be configured and arranged to display a menu or submenu item that allows the user to obtain and display messages or instructions that have been provided by a healthcare professional and stored in clearinghouse 54. For example, a submenu that is generated upon selection of the previously mentioned communications mode can include submenu items that allow the user to select various communication modes, including a mode in which serial data communication is established between data management unit 10 and clearinghouse 54 and data management unit 10 transmits a message status request to clearinghouse 54. When this technique is used, the data processing system of clearinghouse 54 is programmed to search the clearinghouse memory to determine whether a message exists for the user making the request. Any messages stored in memory for that user are then transmitted to the user and processed for display on display unit 28 of handheld microprocessor unit 12. If no messages exist, clearinghouse 54 transmits a signal that causes display unit 28 to indicate "no messages." In this arrangement, clearinghouse 54 preferably is programmed to store a signal indicating that a stored message has been transmitted to the intended recipient (user). Storing such a signal allows the healthcare professional to determine that messages sent to clearinghouse 54 for forwarding to a patient have been transmitted to that patient. In addition, the program instructions stored in data management unit 10 of FIG. 1 preferably allow the system user to designate whether received messages and instructions are to be stored in the memory of data management unit 10 for subsequent retrieval or review. In addition, in some instances it may be desirable to program clearinghouse 54 and data management unit 10 so that the healthcare professional can designate (i.e., flag) information such as changes in medication that will be prominently displayed to the user (e.g., accompanied by a blinking indicator) and stored in the memory of data management unit 10 regardless of whether the system user designates the information for storage.

A second technique that can be used for forwarding messages or instructions to a user does not require the system user to select a menu item requesting transmission by clearinghouse 54 of messages that have been stored for forwarding to that user. In particular, clearinghouse 54 can be programmed to operate in a manner that either automatically transmits stored messages for that user when the user operates the system of FIG. 1 to send information to the clearinghouse or programmed to operate in a manner that informs the user that messages are available and allows the user to access the messages when lie or she chooses to do so.

Practicing the invention in an environment in which the healthcare professional uses a personal computer in some or all of the above-discussed ways can be very advantageous. On the other hand, the invention also provides healthcare professionals timely information about system users without the need for a computer (62 in FIG. 2) or any equipment other than a conventional facsimile machine (55 in FIGS. 1 and 2). Specifically, information provided to clearinghouse 54 by a system user 58 can be sent to a healthcare professional 60 via telephone line 68 and facsimile machine 55, with the information being formatted as a standardized graphic or textual report (56 in FIG. 1). Formatting a standardized report 56 (i.e., analyzing and processing data supplied by blood glucose monitor 16 or other system monitor or sensor) can be effected either by data management unit 10 or within the clearinghouse facility 54. Moreover, various standardized reports can be provided (e.g., the textual and graphic displays discussed below relating to FIGS. 6-10). Preferably, the signal processing arrangement included in clearinghouse 54 allows each healthcare professional 60 to select which of several standardized reports will be routinely transmitted to the healthcare professionals' facsimile machine 55, and, to do so on a patient-by-patient (user-by-user) basis.

Figure 3:
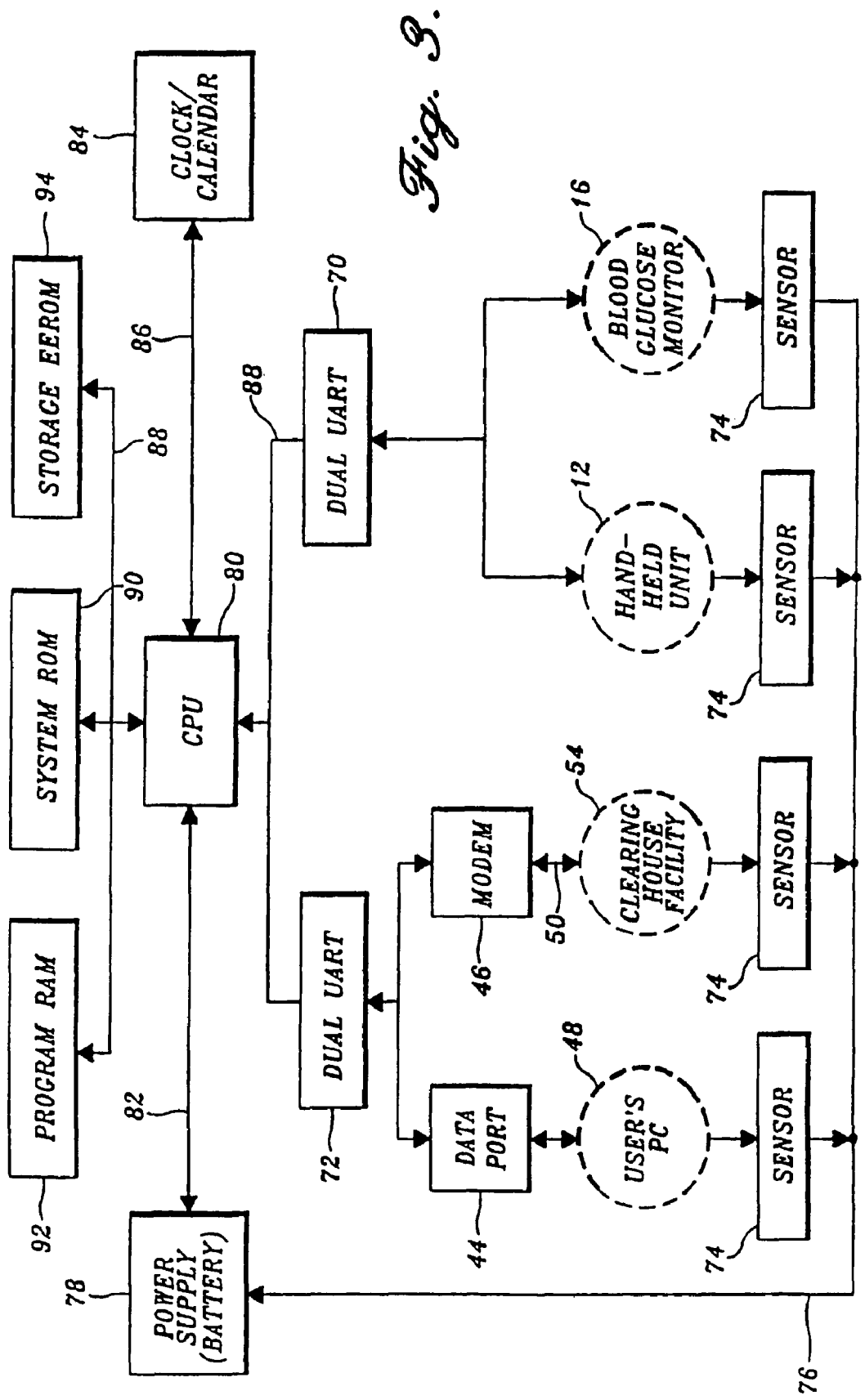
FIG. 3 is a block diagram diagrammatically depicting the structural arrangement of the system data management unit and its interconnection with other components of the system shown in FIG. 1.

FIG. 3 illustrates the manner in which data management unit 10 is arranged and interconnected with other system components for effecting the above-described operational aspects of the invention and additional aspects that are described relative to FIGS. 4-10. As is symbolically indicated in FIG. 3, handheld microprocessor unit 12 and blood glucose monitor 16 are connected to a dual universal asynchronous receiver transmitter 70 (e.g., by cables 14 and 18 of FIG. 1, respectively). As also is indicated in FIG. 3 when a system user connects a personal computer 48 (or other programmable digital signal processor) to data port 44, signal communication is established between personal computer 48 and a second dual universal asynchronous receiver transmitter 72 of data management unit 10. Additionally, dual universal asynchronous receiver transmitter 72 is coupled to modem 46 so that data communication can be established between data management unit 10 and a remote clearinghouse 54 of FIGS. 1 and 2.

Currently preferred embodiments of data management unit 10 include a plurality of signal sensors 74, with an individual signal sensor being associated with each device that is (or may be) interconnected with data management unit 10. As previously discussed and as is indicated in FIG. 3, these devices include handheld microprocessor unit 12, blood glucose monitor 16, personal computer 48, remote computing facility 54 and, in addition, peak-flow meter 20 or other additional monitoring devices 22. Each signal sensor 74 that is included in data management unit 10 is electrically connected for receiving a signal that will be present when the device with which that particular signal sensor is associated is connected to data management unit 10 and, in addition, is energized (e.g., turned on). For example, in previously mentioned embodiments of the invention in which data port 44 is an RS-232 connection, the signal sensor 74 that is associated with personal computer 48 can be connected to an RS-232 terminal that is supplied power when a personal computer is connected to data port 44 and the personal computer is turned on. In a similar manner, the signal sensor 74 that is associated with clearinghouse 54 can be connected to modem 46 so that the signal sensor 74 receives an electrical signal when modem 46 is interconnected to a remote computing facility (e.g., clearinghouse 54 of FIG. 2) via a telephone line 50.

In the arrangement of FIG. 3, each signal sensor 74 is a low power switch circuit (e.g., a metal-oxide semiconductor field-effect transistor circuit), which automatically energizes data management unit 10 whenever any one (or more) of the devices associated with signal sensors 74 is connected to data management unit 10 and is energized. Thus, as is indicated in FIG. 3 by signal path 76, each signal sensor 74 is interconnected with power supply 78, which supplies operating current to the circuitry of data management unit 10 and typically consists of one or more small batteries (e.g., three AAA alkaline cells).

The microprocessor and other conventional circuitry that enables data management unit 10 to process system signals in accordance with stored program instructions is indicated in FIG. 3 by central processing unit (CPU) 80. As is indicated in FIG. 3 by interconnection 82 between CPU 80 and battery 78, CPU 80 receives operating current from power supply 78, with power being provided only when one or more of the signal sensors 74 are activated in the previously described manner. A clock/calendar circuit 84 is connected to CPU 80 (via signal path 86 in FIG. 3) to allow time and date tagging of blood glucose tests and other information. Although not specifically shown in FIG. 3, operating power is supplied to clock/calendar 84 at all times.

In operation, CPU 80 receives and sends signals via a data bus (indicated by signal path 88 in FIG. 3) which interconnects CPU 80 with dual universal asynchronous receiver transmitters 70 and 72. The data bus 88 also interconnects CPU 80 with memory circuits which, in the depicted embodiment, include a system read-only memory (ROM) 90, a program random access memory (RAM) 92, and an electronically erasable read-only memory (EEROM) 94. System ROM 90 stores program instructions and any data required in order to program data management unit 10 so that data management unit 10 and a handheld microprocessor unit 12 that is programmed with a suitable program cartridge 72 provide the previously discussed system operation and, in addition, system operation of the type described relative to FIGS. 4-10. During operation of the system, program RAM 92 provides memory space that allows CPU 80 to carry out various operations that are required for sequencing and controlling the operation of the system of FIG. 1. In addition, RAM 92 can provide memory space that allows external programs (e.g., programs provided by clearinghouse 54) to be stored and executed. EEROM 94 allows blood glucose test results and other data information to be stored and preserved until the information is no longer needed (i.e., until purposely erased by operating the system to provide an appropriate erase signal to EEROM 94).

Figure 4:
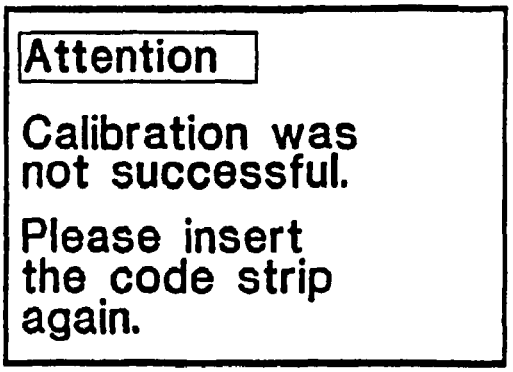
FIGS. 4-10 depict typical system screen displays of data and information that can be provided by the arrangements shown in FIGS. 1-3.
Figure 5:
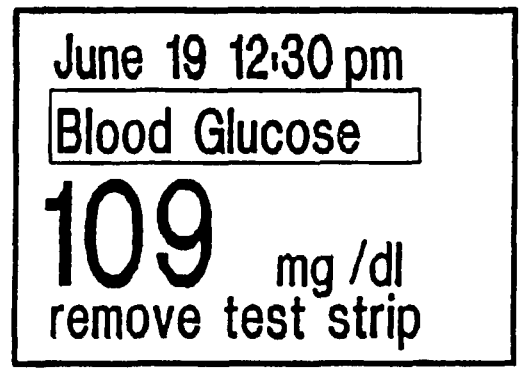

FIGS. 4-10 illustrate typical screen displays that are generated by the arrangement of the invention described relative to FIGS. 1-3. Reference will first be made to FIGS. 4 and 5, which exemplify screen displays that are associated with operation of the invention in the blood glucose monitoring mode. Specifically, in the currently preferred embodiments of the invention, blood glucose monitor 16 operates in conjunction with data management unit 10 and handheld microprocessor unit 12 to: (a) perform a test or calibration sequence in which tests are performed to confirm that the system is operating properly; and, (b) perform the blood glucose test sequence in which blood glucose meter 16 senses the user's blood glucose level. Suitable calibration procedures for blood glucose monitors are known in the art. For example, blood glucose monitors often are supplied with a "code strip," that is inserted in the monitor and results in a predetermined value being displayed and stored in memory at the conclusion of the code strip calibration procedure. When such a code strip calibration procedure is used in the practice of the invention, the procedure is selected from one of the system menus. For example, if the system main menu includes a "monitor" menu item, a submenu displaying system calibration options and an option for initiating the blood glucose test may be displayed when the monitor menu item is selected. When a code strip option is available and selected, a sequence of instructions is generated and displayed by display screen 28 of handheld microprocessor unit 12 to prompt the user to insert the code strip and perform all other required operations. At the conclusion of the code strip calibration sequence, display unit 28 of handheld microprocessor unit 12 displays a message indicating whether or not the calibration procedure has been successfully completed. For example, FIG. 4 illustrates a screen display that informs the system user that the calibration procedure was not successful and that the code strip should be inserted again (i.e., the calibration procedure is to be repeated). As is indicated in FIG. 4, display screens that indicate a potential malfunction of the system include a prominent message such as the "Attention" notation included in the screen display of FIG. 4.

As previously indicated, the blood glucose test sequence that is employed in the currently preferred embodiment of the invention is of the type in which a test strip is inserted in a receptacle that is formed in the blood glucose monitor. A drop of the user's blood is then applied to the test strip and a blood glucose sensing sequence is initiated. When the blood glucose sensing sequence is complete, the user's blood glucose level is displayed.

In the practice of the invention, program instructions stored in data management unit 10 (e.g., system ROM 90 of FIG. 3) and program instructions stored in program cartridge 42 of handheld microprocessor unit 12 cause the system to display step-by-step monitoring instructions to the system user and, in addition, preferably result in display of diagnostic messages if the test sequence does not proceed in a normal fashion. Although currently available self-contained microprocessor-based blood glucose monitors also display test instruction and diagnostic messages, the invention provides greater message capacity and allows multi-line instructions and diagnostic messages that are displayed in easily understood language rather than cryptic error codes and abbreviated phraseology that is displayed one line or less at a time. For example, as is shown in FIG. 5, the complete results of a blood glucose test (date, time of day, and blood glucose level in milligrams per deciliter) can be concurrently displayed by display screen 28 of handheld microprocessor unit 12 along with an instruction to remove the test strip from blood glucose monitor 16. As previously mentioned, when the blood glucose test is complete, the time and date tagged blood glucose test result is stored in the memory circuits of data management unit 10 (e.g., stored in EEPROM 94 of FIG. 3).

The arrangement shown and described relative to FIGS. 1-3 also is advantageous in that data relating to food intake, concurrent medication dosage and other conditions easily can be entered into the system and stored with the time and date tagged blood glucose test result for later review and analysis by the user and/or his or her healthcare professional. Specifically, a menu generated by the system at the beginning or end of the blood glucose monitoring sequence can include items such as "hypoglycemic" and "hyperglycemic," which can be selected using the switches of handheld microprocessor unit 12 (e.g., operation of control pad 30 and switch 36 in FIG. 1) to indicate the user was experiencing hypoglycemic or hyperglycemic symptoms at the time of monitoring blood glucose level. Food intake can be quantitatively entered in terms of "Bread Exchange" units or other suitable terms by, for example, selecting a food intake menu item and using a submenu display and the switches of handheld microprocessor 12 to select and enter the appropriate information. A similar menu item—submenu selection process also can be used to enter medication data such as the type of insulin used at the time of the glucose monitoring sequence and the dosage.

Figure 6:
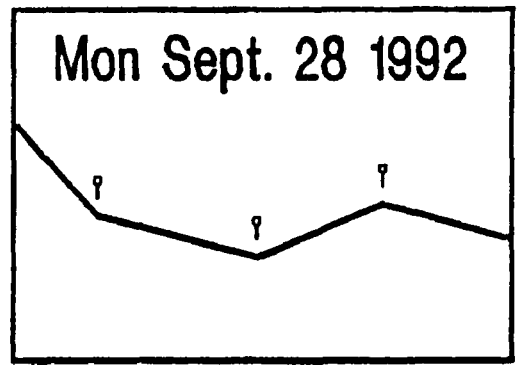
Figure 7:
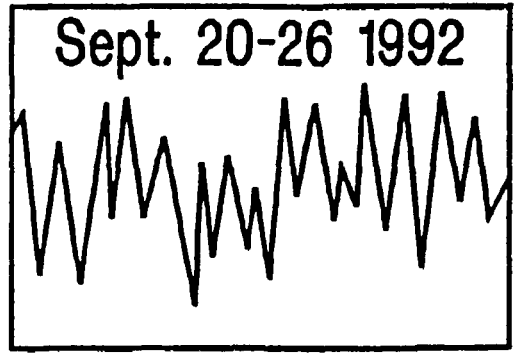

As was previously mentioned, program instructions stored in data management unit 10 and program instructions stored in program cartridge 42 of handheld microprocessor unit 12 enable the system to display statistical and trend information either in a graphic or alphanumeric format. As is the case relative to controlling other operational aspects of the system, menu screens are provided that allow the system user to select the information that is to be displayed. For example, in the previously discussed embodiments in which a system menu includes a "display" menu item, selection of the menu item results in the display of one or more submenus that list available display options. For example, in the currently preferred embodiments, the user can select graphic display of blood glucose test results over a specific period of time, such as one day, or a particular week. Such selection results in displays of the type shown in FIGS. 6 and 7, respectively. When blood glucose test results for a single day are displayed (FIG. 6), the day of the week and date can be displayed along with a graphic representation of changes in blood glucose level between the times at which test results were obtained. In the display of FIG. 6, small icons identify points on the graphic representation that correspond to the blood glucose test results (actual samples). Although not shown in FIG. 6, coordinate values for blood glucose level and time of day can be displayed if desired. When the user chooses to display a weekly trend graph (FIG. 7), the display generated by the system is similar to the display of a daily graph, having the time period displayed in conjunction with a graph that consists of lines interconnecting points that correspond to the blood glucose test results.

Figures 8, 9, 10:
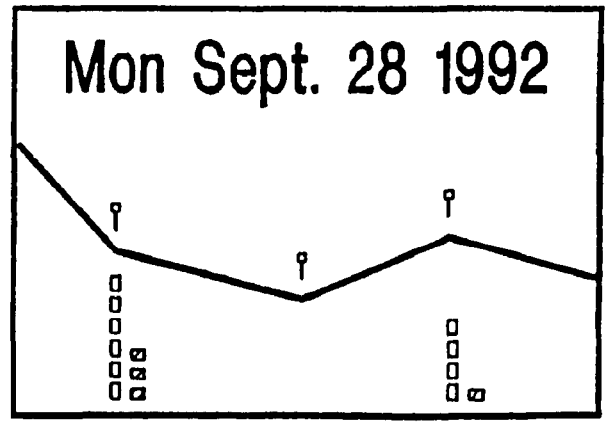

The screen display shown in FIG. 8 is representative of statistical data that can be determined by the system of FIG. 1 (using conventional computation techniques) and displayed in alphanumeric format. As previously mentioned, such statistical data and information in various other textual and graphic formats can be provided to a healthcare professional (60 in FIG. 2) in the form of a standardized report 56 (FIG. 1) that is sent by clearinghouse 54 to facsimile machine 55. In the exemplary screen display of FIG. 8, statistical data for blood glucose levels over a period of time (e.g., one week) or, alternatively, for a specified number of monitoring tests is provided. In the exemplary display of FIG. 8, the system (data management unit 10 or clearinghouse 54) also calculates and displays (or prints) the average blood glucose level and the standard deviation. Displayed also is the number of blood glucose test results that were analyzed to obtain the average and the standard deviation: the number of test results under a predetermined level (50 milligrams per deciliter in FIG. 8); and the number of blood glucose tests that were conducted while the user was experiencing hypoglycemic symptoms. As previously noted, in the preferred embodiments of the invention, a screen display that is generated during the blood glucose monitoring sequence allows the user to identify the blood sample being tested as one taken while experiencing hyperglycemic or hypoglycemic symptoms and, in addition, allows the user to specify other relevant information such as food intake and medication information.

The currently preferred embodiments of the invention also allow the user to select a display menu item that enables the user to sequentially address, in chronological order, the record of each blood glucose test. As is indicated in FIG. 9, each record presented to the system user includes the date and time at which the test was conducted, the blood glucose level, and any other information that the user provided. For example, the screen display of FIG. 9 indicates that the user employed handheld microprocessor unit 12 as an interface to enter data indicating use of 12.5 units of regular insulin; 13.2 units of "NPH" insulin; food intake of one bread exchange unit; and pre-meal hypoglycemic symptoms.

Use of data management unit 10 in conjunction with handheld microprocessor unit 12 also allows display (or subsequent generation of a standardized report 56) showing blood glucose test results along with food intake and/or medication information. For example, shown in FIG. 10 is a daily graph in which blood glucose level is displayed in the manner described relative to FIG. 6. Related food intake and medication dosage is indicated directly below contemporaneous blood glucose levels by vertical bar graphs.

It will be recognized by those skilled in the art that the above-described screen displays and system operation can readily be attained with conventional programming techniques of the type typically used in programming microprocessor arrangements. It also will be recognized by those skilled in the art that various other types of screen displays can be generated and, in addition, that numerous other changes can be made in the embodiments described herein without departing from the scope and the spirit of the invention.

Figure 11:
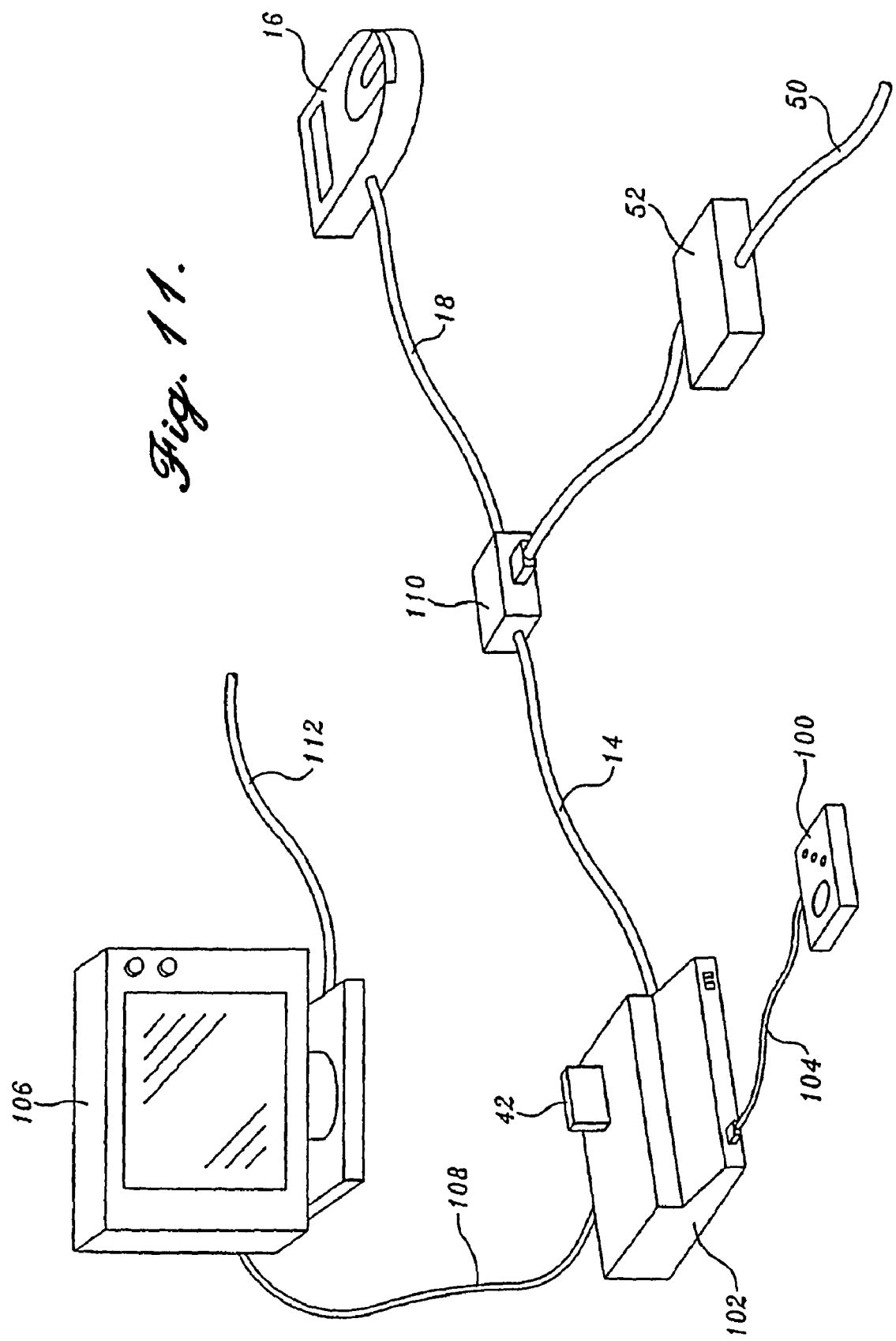
FIG. 11 diagrammatically illustrates an alternative healthcare monitoring system that is arranged in accordance with the invention.

It will also be recognized by those skilled in the art that the invention can be embodied in forms other than the embodiments described relative to FIGS. 1-10. For example, the invention can employ compact video game systems that are configured differently than the previously discussed handheld video game systems and palm-top computers. More specifically, as is shown in FIG. 11, a self-care health monitoring system arranged in accordance with the invention can employ a compact video game system of the type that includes one or more controllers 100 that are interconnected to a game console 102 via cable 104. As is indicated in FIG. 11, game console 102 is connected to a video monitor or television 106 by means of a cable 108. Although differing in physical configuration, controller 100, game console 102 and the television or video monitor 106 collectively function in the same manner as the handheld microprocessor 12 of FIG. 1. In that regard, a program cartridge 42 is inserted into a receptacle contained in game console 102, with program cartridge 42 including stored program instructions for controlling microprocessor circuitry that is located inside game console 102. Controller 100 includes a control pad or other device functionally equivalent to control pad 30 of FIG. 1 and switches that functionally correspond to switches 32-38 of FIG. 1.

Regardless of whether the invention is embodied with a handheld microprocessor unit (FIG. 1) or an arrangement such as the compact video game system (FIG. 1), in some cases it is both possible and advantageous to apportion the signal processing functions and operations differently than was described relative to FIGS. 1-10. For example, in some situations, the microprocessor-based unit that is programmed by a card or cartridge (e.g., handheld unit 12 of FIG. 1 or compact video game console 102 of FIG. 11) includes memory and signal processing capability that allows the microprocessor to perform all or most of the functions and operations attributed to data management unit 10 of the embodiments discussed relative to FIGS. 1-10. That is, the digitally encoded signal supplied by blood glucose monitor 16 (or one of the other monitors 20 and 22 of FIG. 1) can be directly coupled to the microprocessor included in game console 102 of FIG. 11 or handheld microprocessor 12 of FIG. 1. In such an arrangement, the data management unit is a relatively simple signal interface (e.g., interface unit 110 of FIG. 11), the primary purpose of Which is carrying signals between the blood glucose monitor 16 (or other monitor) and the microprocessor of game console 102 (FIG. 11) or handheld unit 12 (FIG. 1). In some situations, the interface unit may consist primarily or entirely of a conventional cable arrangement such as a cable for interconnection between RS232 data ports or other conventional connection arrangements. On the other hand, as is shown in FIG. 11, signal interface 110 can either internally include or be connected to a modem 52, which receives and transmits signals via a telephone line 50 in the manner described relative to FIGS. 1 and 2.

It also should be noted that all or a portion of the functions and operations attributed to data management unit 10 of FIG. 1 can be performed by microprocessor circuitry located in blood glucose monitor 16 (or other monitor that is used with the system). For example, a number of commercially available blood glucose monitors include a clock/calendar circuit of the type described relative to FIG. 3 and, in addition, include microprocessor circuitry for generating visual display signals and signals representative of both current and past values of monitored blood glucose level. Conventional programming and design techniques can be employed to adapt such commercially available units for the performance of the various functions and operations attributed in the above discussion of FIGS. 1-11 to data management unit 10 and/or the microprocessors of handheld unit 12 and compact video console 102. In arrangements in which the blood glucose monitor (or other system monitor) includes a microprocessor that is programmed to provide signal processing in the above-described manner, the invention can use a signal interface unit 110 of the above-described type. That is, depending upon the amount of signal processing effected by the monitoring unit (e.g., blood glucose monitor 16) and the amount of signal processing performed by the microprocessor of video game console 102 (or handheld unit 12), the signal interface required ranges from a conventional cable (e.g., interconnection of RS232 ports) to an arrangement in which signal interface 110 is arranged for signal communication with an internal or external modem (e.g., modem 52 of FIG. 11) or an arrangement in which signal interface 110 provides only a portion of the signal processing described relative to FIGS. 1-10.

The invention also is capable of transmitting information to a remote location (e.g., clearinghouse 54 and/or a remotely located healthcare professional) by means other than conventional telephone lines. For example, a modem (52 in FIGS. 1 and 11) that is configured for use with a cellular telephone system can be employed to transmit the signals provided by the healthcare monitoring system to a remote location via modulated RF transmission. Moreover, the invention can be employed with various digital networks such as recently developed interactive voice, video and data systems such as television systems in which a television and user interface apparatus is interactively coupled to a remote location via coaxial or fiberoptic cable and other transmission media (indicated in FIG. 11 by cable 112, which is connected to television or video monitor 106). In such an arrangement, compact video game controller 100 and the microprocessor of video game console 102 can be programmed to provide the user interface functions required for transmission and reception of signals via the interactive system. Alternatively, the signals provided by video game console 102 (or handheld unit 12 if FIG. 1) can be supplied to the user interface of the interactive system (not shown in FIG. 11) in a format that is compatible with the interactive system and allows the system user interface to be used to control signal transmission between the healthcare system and a remote facility such as clearinghouse 54, FIGS. 1 and 2.

The invention presents a system and method for remotely monitoring individuals and for communicating information to the individuals. In a preferred embodiment of the invention, the individuals are patients and the system is used to collect data relating to the health status of the patients. However, it is to be understood that the invention is not limited to remote patient monitoring. The system and method of the invention may be used for any type of remote monitoring application. The invention may also be implemented as an automated messaging system for communicating information to individuals, as will be discussed in an alternative embodiment below.

Figure 12:
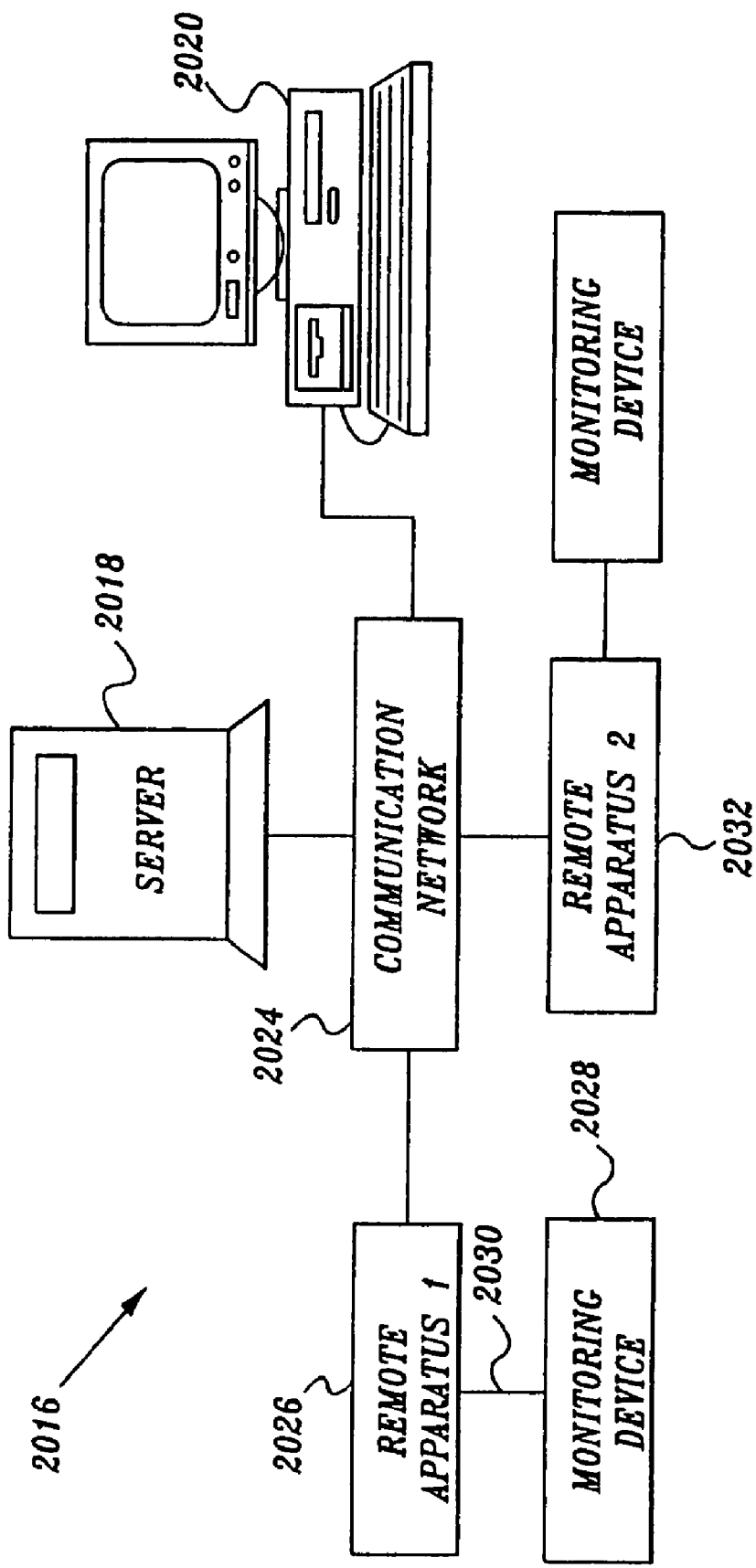
FIG. 12 is a block diagram of a networked system according to a preferred embodiment of the invention.

A preferred embodiment of the invention is illustrated in FIGS. 12-23. Referring to FIG. 12, a networked system 2016 includes a server 2018 and a workstation 2020 connected to server 2018 through a communication network 2024. Server 2018 is preferably a world wide web server and communication network 2024 is preferably the Internet. It will be apparent to one skilled in the art that server 2018 may comprise a single stand-alone computer or multiple computers distributed throughout a network. Workstation 2020 is preferably a personal computer, remote terminal, or web TV unit connected to server 2018 via the Internet. Workstation 2020 functions as a remote interface for entering in server 2018 messages and queries to be communicated to the patients.

System 2016 also includes first and second remotely programmable apparatuses 2026 and 2032 for monitoring first and second patients, respectively. Each apparatus is designed to interact with a patient in accordance with script programs received from server 2018. Each apparatus is in communication with server 2018 through communication network 2024, preferably the Internet. Alternatively, each apparatus may be placed in communication with server 2018 via wireless communication networks, cellular networks, telephone networks, or any other network which allows each apparatus to exchange data with server 2018. For clarity of illustration, only two apparatuses are shown in FIG. 12. It is to be understood that system 2016 may include any number of apparatuses for monitoring any number of patients.

In the preferred embodiment, each patient to be monitored is also provided with a monitoring device 2028. Monitoring device 2028 is designed to produce measurements of a physiological condition of the patient, record the measurements, and transmit the measurements to the patient's apparatus through a standard connection cable 2030. Examples of suitable monitoring devices include blood glucose meters, respiratory flow meters, blood pressure cuffs, electronic weight scales, and pulse rate monitors. Such monitoring devices are well known in the art. The specific type of monitoring device provided to each patient is dependent upon the patient's disease. For example, diabetes patients are provided with a blood glucose meters for measuring blood glucose concentrations, asthma patients are provided with respiratory flow meters for measuring peak flow rates, obesity patients are provided with weight scales, etc.

Figure 13:
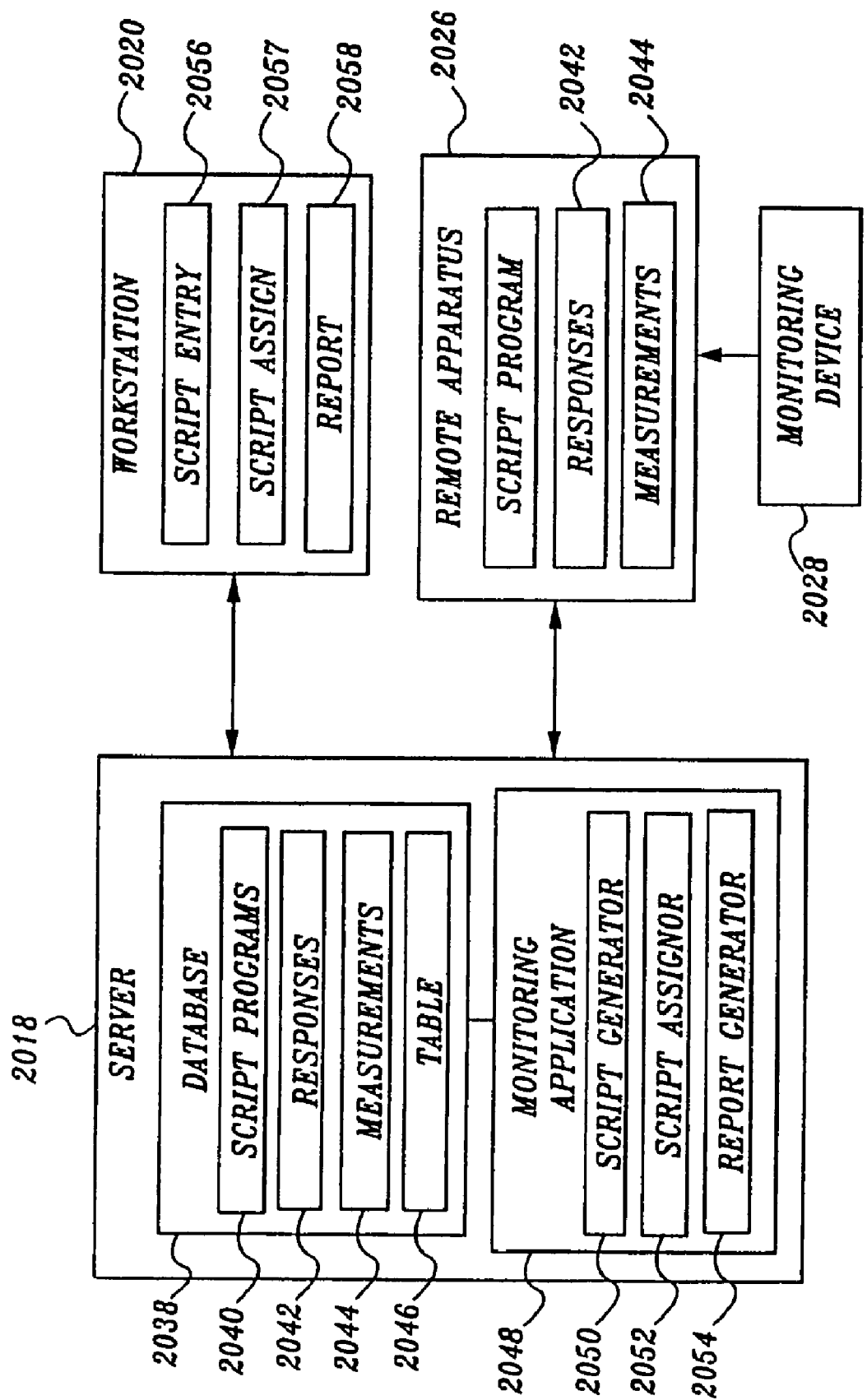
FIG. 13 is a block diagram illustrating the interaction of the components of the system of FIG. 12.

FIG. 13 shows server 2018, workstation 2020, and apparatus 2026 in greater detail. Server 2018 includes a database 2038 for storing script programs 2040. The script programs are executed by each apparatus to communicate queries and messages to a patient, receive responses 2042 to the queries, collect monitoring device measurements 2044, and transmit responses 2042 and measurements 2044 to server 2018. Database 2038 is designed to store the responses 2042 and measurements 2044. Database 2038 further includes a look-up table 2046. Table 2046 contains a list of the patients to be monitored, and for each patient, a unique patient identification code and a respective pointer to the script program assigned to the patient. Each remote apparatus is designed to execute assigned script programs which it receives from server 2018.

Figure 14:
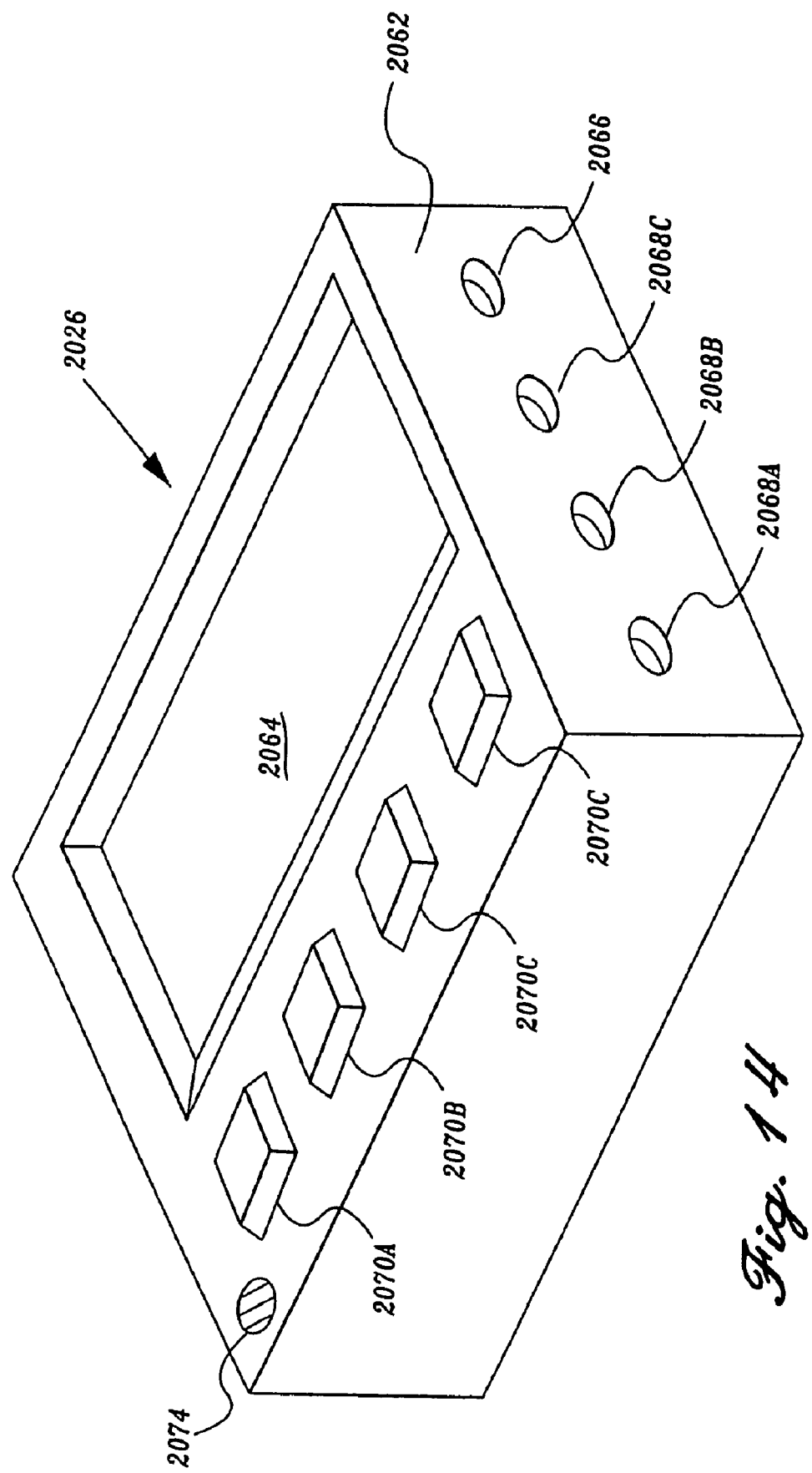
FIG. 14 is a perspective view of a remotely programmable apparatus of the system of FIG. 12.
Figure 15:
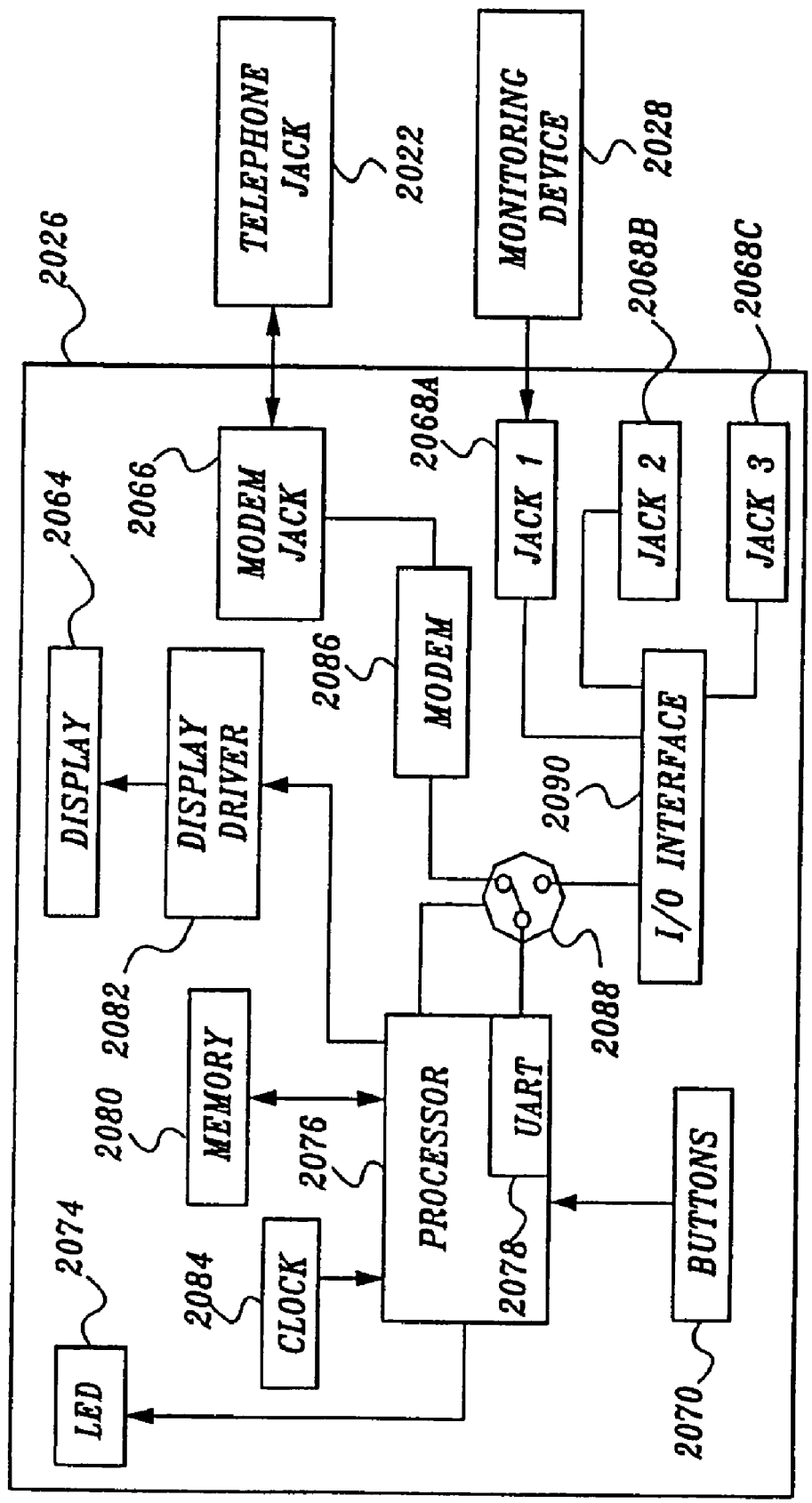
FIG. 15 is a block diagram illustrating the components of the apparatus of FIG. 14.

FIGS. 14-15 show the structure of each apparatus according to the preferred embodiment. For clarity, only apparatus 2026 is shown since each apparatus of the preferred embodiment has substantially identical structure to apparatus 2026. Referring to FIG. 14, apparatus 2026 includes a housing 2062. Housing 2062 is sufficiently compact to enable apparatus 2026 to be hand-held and carried by a patient. Apparatus 2026 also includes a display 2064 for displaying queries and prompts to the patient. In the preferred embodiment, display 2064 is a liquid crystal display (LCD).

Four user input buttons 2070A, 2070B, 2070C, and 2070D are located adjacent display 2064. The user input buttons are for entering in apparatus 2026 responses to the queries and prompts. In the preferred embodiment, the user input buttons are momentary contact push buttons. In alternative embodiments, the user input buttons may be replaced by switches, keys, a touch sensitive display screen, or any other data input device.

Three monitoring device jacks 2068A, 2068B, and 2068C are located on a surface of housing 2062. The device jacks are for connecting apparatus 2026 to a number of monitoring devices, such as blood glucose meters, respiratory flow meters, or blood pressure cuffs, through respective connection cables (not shown). Apparatus 2026 also includes a modem jack 2066 for connecting apparatus 2026 to a telephone jack through a standard connection cord (not shown). Apparatus 2026 further includes a visual indicator, such as a light emitting diode (LED) 2074. LED 2074 is for visually notifying the patient that he or she has unanswered queries stored in apparatus 2026.

FIG. 15 is a schematic block diagram illustrating the components of apparatus 2026 in greater detail. Apparatus 2026 includes a microprocessor 2076 and a memory 2080 connected to microprocessor 2076. Memory 2080 is preferably a non-volatile memory, such as a serial EEPROM. Memory 2080 stores script programs received from the server, measurements received from monitoring device 2028, responses to queries, and the patient's unique identification code.

Microprocessor 2076 also includes built-in read only memory (ROM) which stores firmware for controlling the operation of apparatus 2026. The firmware includes a script interpreter used by microprocessor 2076 to execute the script programs. The script interpreter interprets script commands which are executed by microprocessor 2076. Specific techniques for interpreting and executing script commands in this manner are well known in the art.

Microprocessor 2076 is preferably connected to memory 2080 using a standard two-wire $I^2C$ interface. Microprocessor 2076 is also connected to user input buttons 2070, LED 2074, a clock 2084, and a display driver 2082. Clock 2084 indicates the current date and time to microprocessor 2076. For clarity of illustration, clock 2084 is shown as a separate component, but is preferably built into microprocessor 2076. Display driver 2082 operates under the control of microprocessor 2076 to display information on display 2064. Microprocessor 2076 is preferably a PIC 16C65 processor which includes a universal asynchronous receiver transmitter (ART) 2078. ART 2078 is for communicating with a modem 2086 and a device interface 2090. A CMOS switch 2088 under the control of microprocessor 2076 alternately connects modem 2086 and interface 2090 to ART 2078.

Modem 2086 is connected to a telephone jack 2022 through modem jack 2066. Modem 2086 is for exchanging data with server 2018 through communication network 2024. The data includes script programs which are received from the server as well as responses to queries, device measurements, script identification codes, and the patient's unique identification code which modem 2086 transmits to the server. Modem 2086 is preferably a complete 28.8 K modem commercially available from Cermetek, although any suitable modem may be used.

Device interface 2090 is connected to device jacks 2068A, 2068B, and 2068C. Device interface 2090 is for interfacing with a number of monitoring devices, such as blood glucose meters, respiratory flow meters, blood pressure cuffs, weight scales, or pulse rate monitors, through the device jacks. Device interface 2090 operates under the control of microprocessor 2076 to collect measurements from the monitoring devices and to output the measurements to microprocessor 2076 for storage in memory 2080. In the preferred embodiment, interface 2090 is a standard RS232 interface. For simplicity of illustration, only one device interface is shown in FIG. 15. However, in alternative embodiments, apparatus 2026 may include multiple device interfaces to accommodate monitoring devices which have different connection standards.

Referring again to FIG. 13, server 2018 includes a monitoring application 2048. Monitoring application 2048 is a controlling software application executed by server 2018 to perform the various functions described below. Application 2048 includes a script generator 2050, a script assignor 2052, and a report generator 2054. Script generator 2050 is designed to generate script programs 2040 from script information entered through workstation 2020. The script information is entered through a script entry screen 2056. In the preferred embodiment, script entry screen 2056 is implemented as a web page on server 2018. Workstation 2020 includes a web browser for accessing the web page to enter the script information.

FIG. 16 illustrates script entry screen 2056 as it appears on workstation 2020. Screen 2056 includes a script name field 2092 for specifying the name of a script program to be generated. Screen 2056 also includes entry fields 2094 for entering a set of queries to be answered by a patient. Each entry field 2094 has corresponding response choice fields 2096 for entering response choices for the query. Screen 2056 further includes check boxes 2098 for selecting a desired monitoring device from which to collect measurements, such as a blood glucose meter, respiratory flow meter, or blood pressure cuff.

Screen 2056 additionally includes a connection time field 2100 for specifying a prescribed connection time at which each apparatus executing the script is to establish a subsequent communication link to the server. The connection time is preferably selected to be the time at which communication rates are the lowest, such as 3:00 AM. Screen 2056 also includes a CREATE SCRIPT button 2102 for instructing the script generator to generate a script program from the information entered in screen 2056. Screen 2056 further includes a CANCEL button 2104 for canceling the information entered in screen 2056.

In the preferred embodiment, each script program created by the script generator conforms to the standard file format used on UNIX systems. In the standard file format, each command is listed in the upper case and followed by a colon. Every line in the script program is terminated by a linefeed character {LF}, and only one command is placed on each line. The last character in the script program is a UNIX end of file character {EOF}. TABLE 1 shows an exemplary listing of script commands used in the preferred embodiment of the invention.

the template the script information entered in screen 2056. For example, FIGS. 17A-17B illustrate a sample script program created by script generator 2050 from the script information shown in FIG. 16.

The script program includes display commands to display the queries and response choices entered in fields 2094 and 2096, respectively. The script program also includes input commands to receive responses to the queries. The script program further includes a collect command to collect device measurements from the monitoring device specified in check boxes 2098. The script program also includes commands to establish a subsequent communication link to the server at the connection time specified in field 2100. The steps included in the script program are also shown in the flow chart of FIGS. 23A-23B and will be discussed in the operation section below.

Referring again to FIG. 13, script assignor 2052 is for assigning script programs 2040 to the patients. Script programs 2040 are assigned in accordance with script assignment information entered through workstation 2020. The script assignment information is entered through a script assignment screen 2057, which is preferably implemented as a web page on server 2018.

Figure 18:
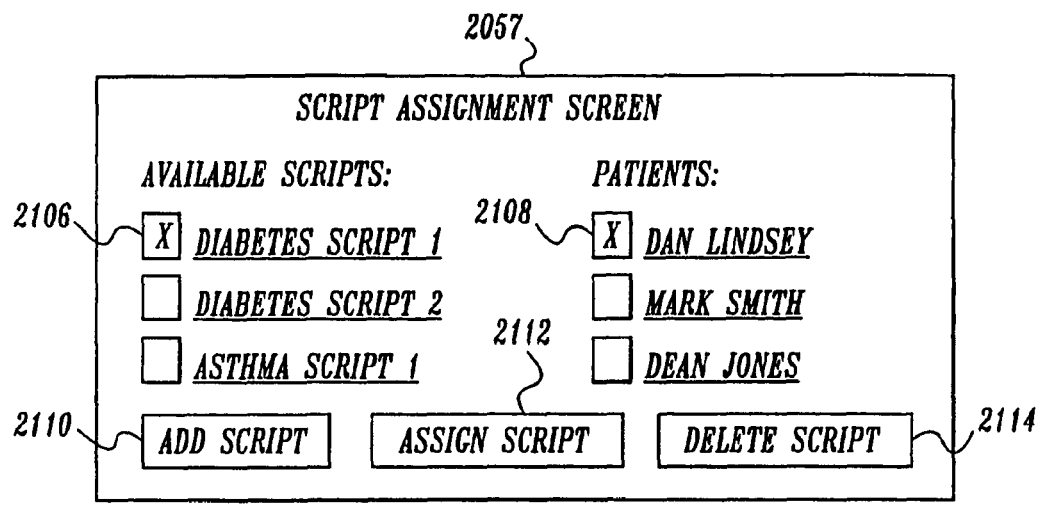
FIG. 18 is a script assignment screen according to the preferred embodiment of the invention.

FIG. 18 illustrates a sample script assignment screen 2057 as it appears on workstation 2020. Screen 2057 includes

TABLE 1

| SCRIPT COMMANDS | COMMAND DESCRIPTION |
| --- | --- |
| CLS: {LF} | Clear the display. |
| ZAP: {LF} | Erase from memory the last set of query responses recorded. |
| LED: b{LF} | Turn the LED on or off, where b is a binary digit of 0 or 1. An argument of 1 turns on the LED, and an argument of 0 turns off the LED. |
| DISPLAY: {chars} {LF} | Display the text following the DISPLAY command. |
| INPUT: mmmm{LF} | Record a button press. The m's represent a button mask pattern of each of the four input buttons. Each m contains an "X" for disallowed buttons or an "O" for allowed buttons. For example, INPUT: OXOX{LF} allows the user to press either button #1 or #3. |
| WAIT: {LF} | Wait for any one button to be pressed, then continue executing the script program. |
| COLLECT: device{LF} | Collect measurements from the monitoring device specified in the COLLECT command. The user is preferably prompted to connect the specified monitoring device to the apparatus and press a button to continue. |
| NUMBER: aaaa{LF} | Assign a script identification code to the script program. The script identification code from the most recently executed NUMBER statement is subsequently transmitted to the server along with the query responses and device measurements. The script identification code identifies to the server which script program was most recently executed by the remote apparatus. |
| DELAY: t{LF} | Wait until time t specified in the DELAY command, usually the prescribed connection time. |
| CONNECT: {LF} | Perform a connection routine to establish a communication link to the server, transmit the patient identification code, query responses, device measurements, and script identification code to the server, and receive and store a new script program. When the server instructs the apparatus to disconnect, the script interpreter is restarted, allowing the new script program to execute. |

The script commands illustrated in TABLE 1 are representative of the preferred embodiment and are not intended to limit the scope of the invention. After consideration of the ensuing description, it will be apparent to one skilled in the art many other suitable scripting languages and sets of script commands may be used to implement the invention.

Script generator 2050 preferably stores a script program template which it uses to create each script program. To generate a script program, script generator 2050 inserts into check boxes 2106 for selecting a script program to be assigned and check boxes 2108 for selecting the patients to whom the script program is to be assigned. Screen 2057 also includes an ASSIGN SCRIPT button 2112 for entering the assignments. When button 2112 is pressed, the script assignor creates and stores for each patient selected in check boxes 2108 a respective pointer to the script program selected in check boxes 2106. Each pointer is stored in the patient lookup table of the database. Screen 2057 further includes an ADD SCRIPT button 2110 for accessing the script entry screen and a DELETE SCRIPT button 2114 for deleting a script program.

Referring again to FIG. 13, report generator 2054 is designed to generate a patient report 2058 from the responses and device measurements received in server 2018. Patient report 2058 is displayed on workstation 2020. FIG. 21 shows a sample patient report 2058 produced by report generator 2054 for a selected patient. Patient report 2058 includes a graph 2116 of the device measurements received from the patient, as well as a listing of responses 2042 received from the patient. Specific techniques for writing a report generator program to display data in this manner are well known in the art.

The operation of the preferred embodiment is illustrated in FIGS. 12-23. FIG. 22A is a flow chart illustrating steps included in the monitoring application executed by server 2018. FIG. 22B is a continuation of the flow chart of FIG. 22A. In step 2202, server 2018 determines if new script information has been entered through script entry screen 2056. If new script information has not been entered, server 2018 proceeds to step 2206. If new script information has been entered, server 2018 proceeds to step 2204.

As shown in FIG. 16, the script information includes a set of queries, and for each of the queries, corresponding responses choices. The script information also includes a selected monitoring device type from which to collect device measurements. The script information further includes a prescribed connection time for each apparatus to establish a subsequent communication link to the server. The script information is generally entered in server 2018 by a healthcare provider, such as the patients' physician or case manager. Of course, any person desiring to communicate with the patients may also be granted access to server 2018 to create and assign script programs. Further, it is to be understood that the system may include any number of remote interfaces for entering script generation and script assignment information in server 2018.

In step 2204, script generator 2050 generates a script program from the information entered in screen 2056. The script program is stored in database 2038. Steps 2202 and 2204 are preferably repeated to generate multiple script programs, e.g. a script program for diabetes patients, a script program for asthma patients, etc. Each script program corresponds to a respective one of the sets of queries entered through script entry screen 2056. Following step 2204, server 2018 proceeds to step 2206.

In step 2206, server 2018 determines if new script assignment information has been entered through assignment screen 2057. If new script assignment information has not been entered, server 2018 proceeds to step 2210. If new script assignment information has been entered, server 2018 proceeds to step 2208. As shown in FIG. 18, the script programs are assigned to each patient by selecting a script program through check boxes 2106, selecting the patients to whom the selected script program is to be assigned through check boxes 2108, and pressing the ASSIGN SCRIPT button 2112. When button 2112 is pressed, script assignor 2052 creates for each patient selected in check boxes 2108 a respective pointer to the script program selected in check boxes 2106. In step 2208, each pointer is stored in look-up table 2046 of database 2038. Following step 2208, server 2018 proceeds to step 2210.

In step 2210, server 2018 determines if any of the apparatuses are remotely connected to the server. Each patient to be monitored is preferably provided with his or her own apparatus which has the patient's unique identification code stored therein. Each patient is thus uniquely associated with a respective one of the apparatuses. If none of the apparatuses is connected, server 2018 proceeds to step 2220.

If an apparatus is connected, server 2018 receives from the apparatus the patient's unique identification code in step 2212. In step 2214, server 2018 receives from the apparatus the query responses 2042, device measurements 2044, and script identification code recorded during execution of a previously assigned script program. The script identification code identifies to the server which script program was executed by the apparatus to record the query responses and device measurements. The responses, device measurements, and script identification code are stored in database 2038.

In step 2216, server 2018 uses the patient identification code to retrieve from table 2046 the pointer to the script program assigned to the patient. The server then retrieves the assigned script program from database 2038. In step 2218, server 2018 transmits the assigned script program to the patient's apparatus through communication network 2024. Following step 2218, server 2018 proceeds to step 2220.

In step 2220, server 2018 determines if a patient report request has been received from workstation 2020. If no report request has been received, server 2018 returns to step 2202. If a report request has been received for a selected patient, server 2018 retrieves from database 2038 the measurements and query responses last received from the patient, step 2222. In step 2224, server 2018 generates and displays patient report 2058 on workstation 2020. As shown in FIG. 21, report 2058 includes the device measurements and query responses last received from the patient. Following step 2224, the server returns to step 2202.

Figure 23A:
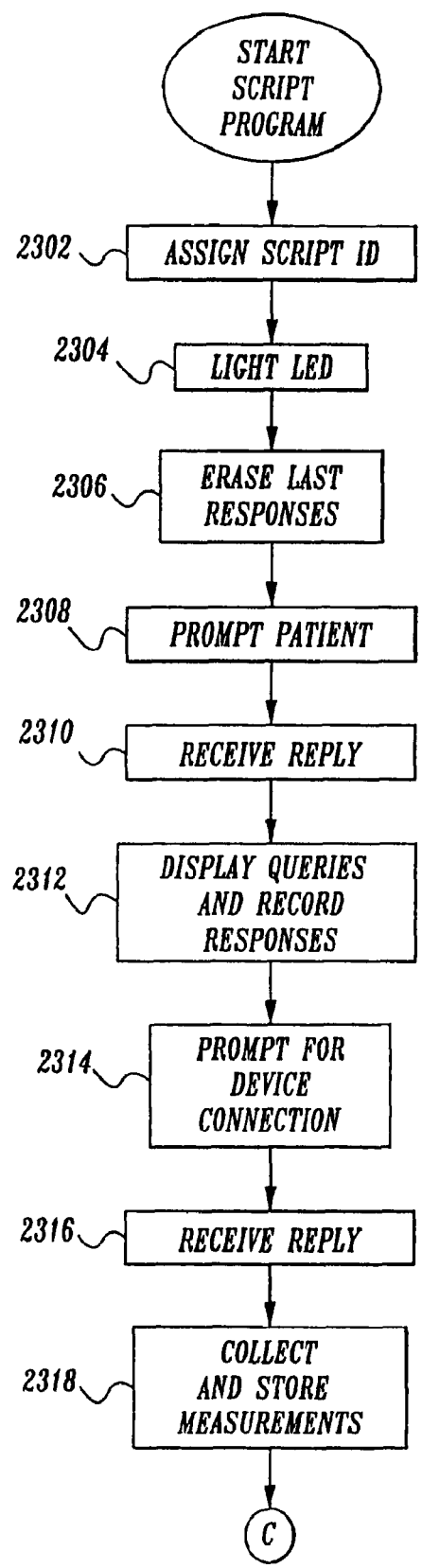
FIG. 23A is a flow chart illustrating the steps included in the script program of FIGS. 17A-17B.
Figure 23B:
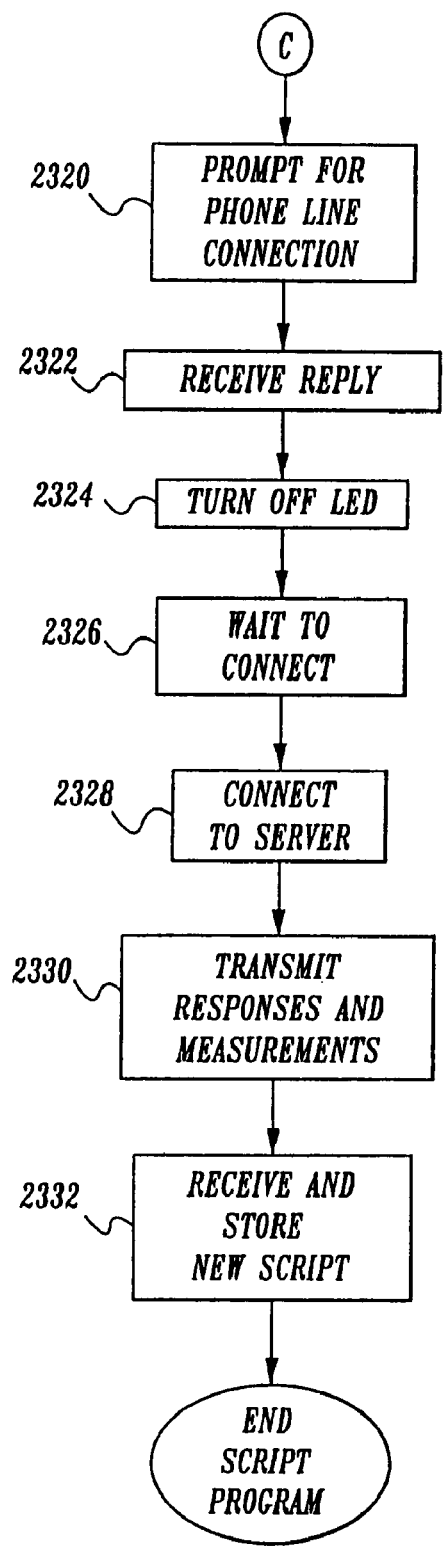
FIG. 23B is a continuation of the flow chart of FIG. 23A.

FIGS. 23A-23B illustrate the steps included in the script program executed by apparatus 2026. Before the script program is received, apparatus 2026 is initially programmed with the patient's unique identification code and the script interpreter used by microprocessor 2076 to execute the script program. The initial programming may be achieved during manufacture or during an initial connection to server 2018. Following initial programming, apparatus 2026 receives from server 2018 the script program assigned to the patient associated with apparatus 2026. The script program is received by modem 2086 through a first communication link and stored in memory 2080.

In step 2302, microprocessor 2076 assigns a script identification code to the script program and stores the script identification code in memory 2080. The script identification code is subsequently transmitted to the server along with the query responses and device measurements to identify to the server which script program was most recently executed by the apparatus. In step 2304, microprocessor 2076 lights LED 2074 to notify the patient that he or she has unanswered queries stored in apparatus 2026. LED 2074 preferably remains lit until the queries are answered by the patient. In step 2306, microprocessor 2076 erases from memory 2080 the last set of query responses recorded.

In step 2308, microprocessor 2076 prompts the patient by displaying on display 2064 "ANSWER QUERIES NOW? PRESS ANY BUTTON TO START". In step 2310, microprocessor 2076 waits until a reply to the prompt is received from the patient. When a reply is received, microprocessor 2076 proceeds to step 2312. In step 2312, microprocessor 2076 executes successive display and input commands to display the queries and response choices on display 2064 and to receive responses to the queries.

Figure 19:
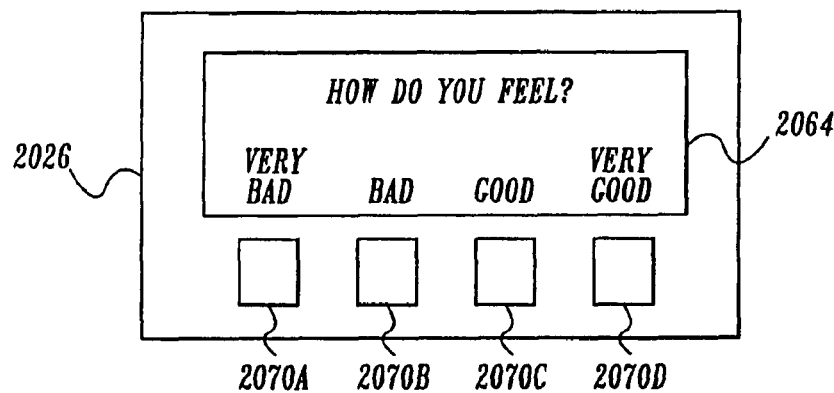
FIG. 19 is a sample query appearing on a display of the apparatus of FIG. 14.

FIG. 19 illustrates a sample query and its corresponding response choices as they appear on display 2064. The response choices are positioned on display 2064 such that each response choice is located proximate a respective one of the input buttons. In the preferred embodiment, each response choice is displayed immediately above a respective input button. The patient presses the button corresponding to his or her response. Microprocessor 2076 stores each response in memory 2080.

Figure 20:
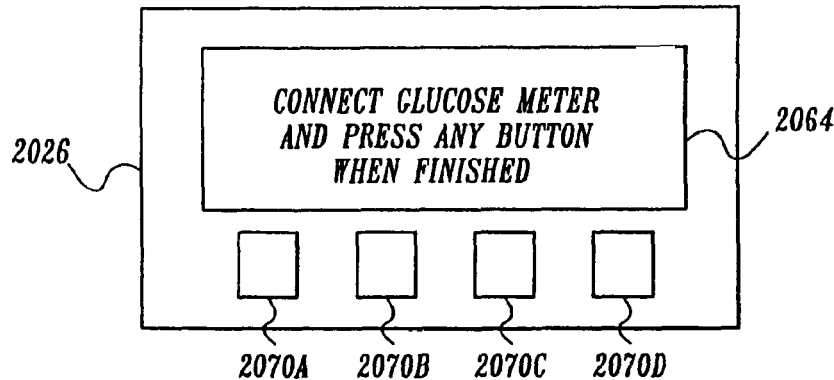
FIG. 20 is a sample prompt appearing on the display of the apparatus of FIG. 14.
Figure 22A:
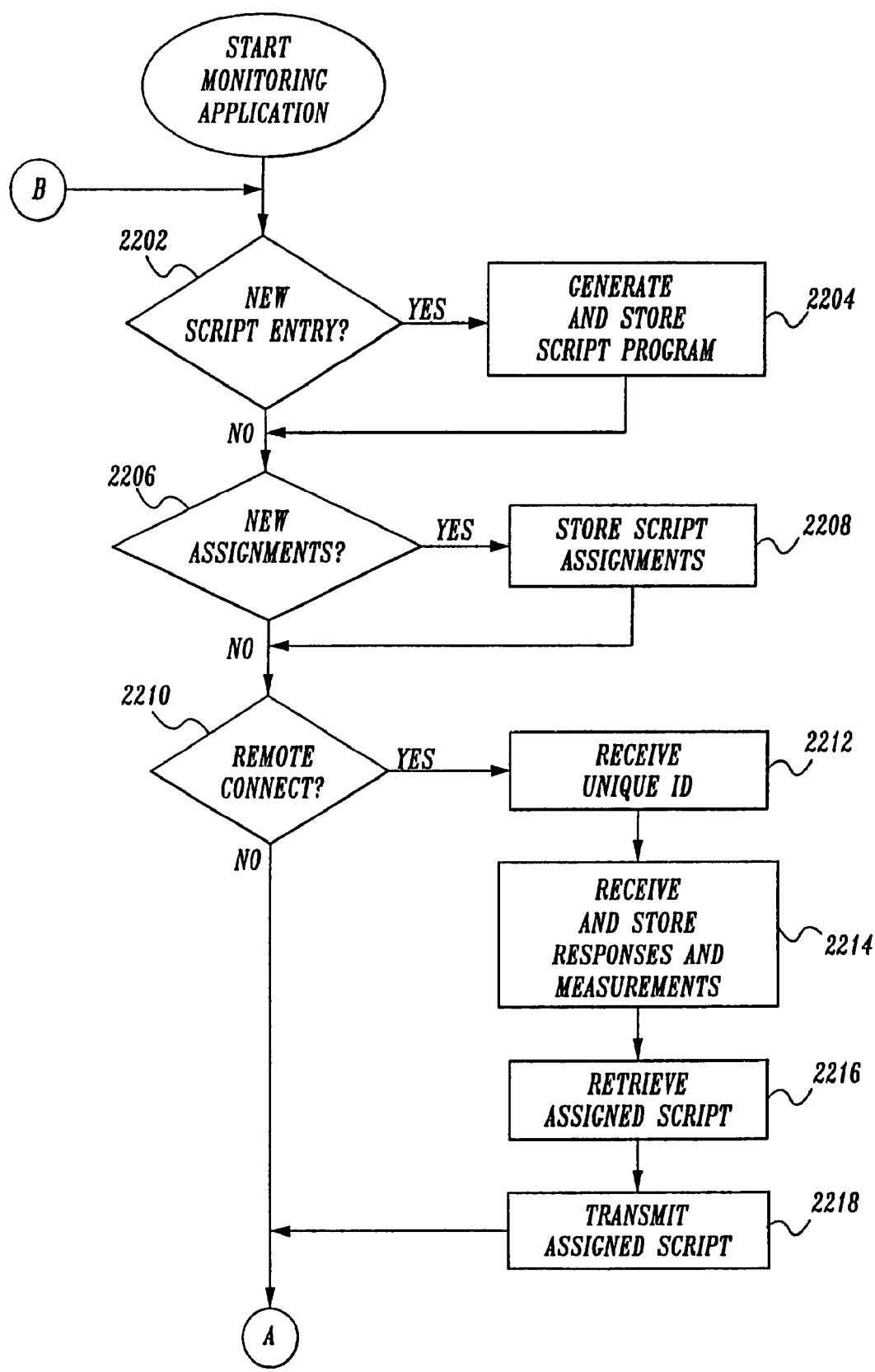
FIG. 22A is a flow chart illustrating the steps included in a monitoring application executed by the server of FIG. 12 according to the preferred embodiment of the invention.
Figure 22B:
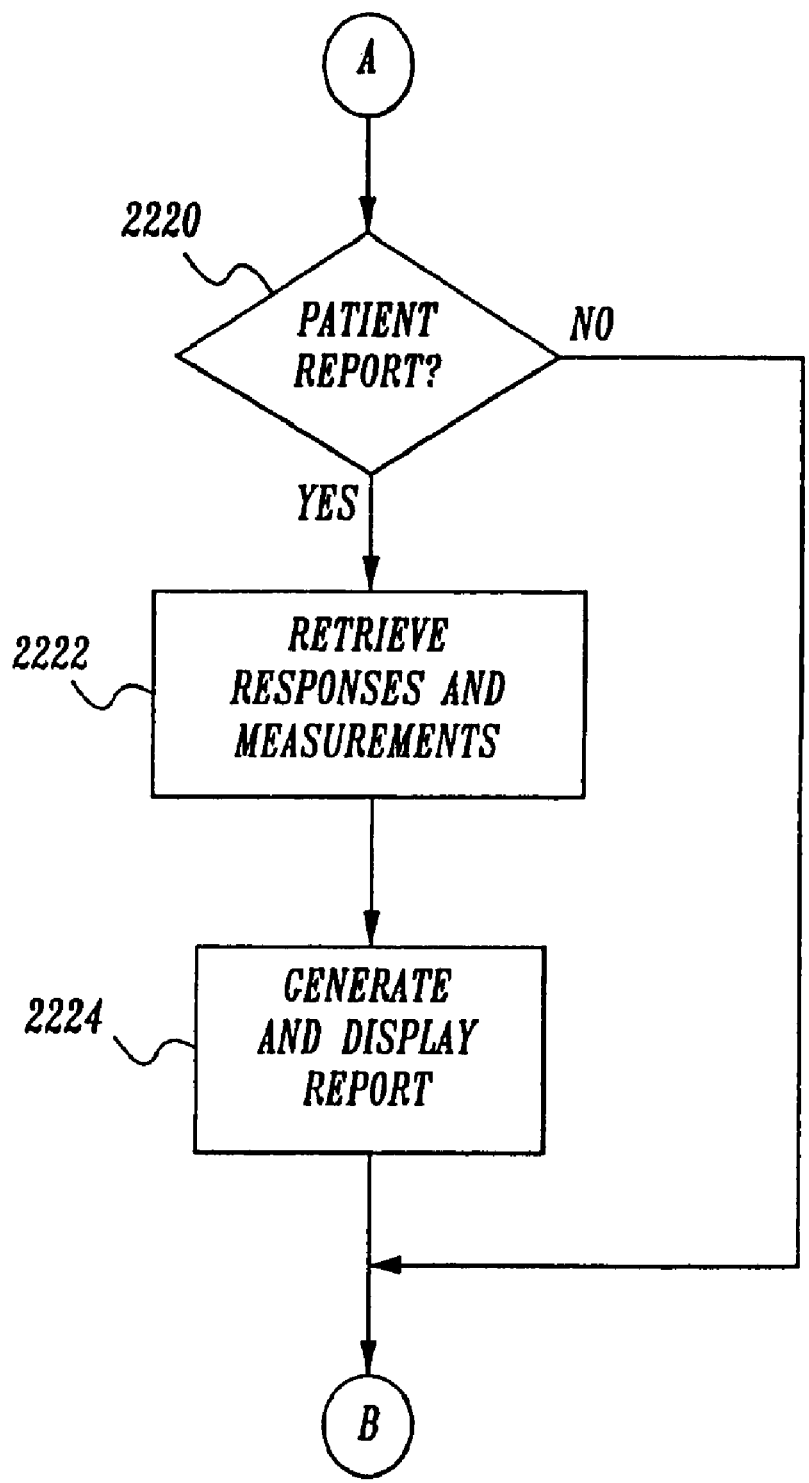
FIG. 22B is a continuation of the flow chart of FIG. 22A.

In steps 2314-2318, microprocessor 2076 executes commands to collect device measurements from a selected monitoring device. The script program specifies the selected monitoring device from which to collect the measurements. In step 2314, microprocessor 2076 prompts the patient to connect the selected monitoring device, for example a blood glucose meter, to one of the device jacks. A sample prompt is shown in FIG. 20. In step 2316, microprocessor 2076 waits until a reply to the prompt is received from the patient. When a reply is received, microprocessor 2076 proceeds to step 2318. Microprocessor 2076 also connects UART 2078 to interface 2090 through switch 2088. In step 2318, microprocessor 2076 collects the device measurements from monitoring device 2028 through interface 2090. The measurements are stored in memory 2080.

In step 2320, microprocessor 2076 prompts the patient to connect apparatus 2026 to telephone jack 2022 so that apparatus 2026 may connect to server 2018 at the prescribed connection time. In step 2322, microprocessor 2076 waits until a reply to the prompt is received from the patient. When a reply is received, microprocessor 2076 turns off LED 2074 in step 2324. In step 2326, microprocessor 2076 waits until it is time to connect to server 2018. Microprocessor 2076 compares the connection time specified in the script program to the current time output by clock 2084. When it is time to connect, microprocessor 2076 connects UART 2078 to modem 2086 through switch 2088.

In step 2328, microprocessor 2076 establishes a subsequent communication link between apparatus 2026 and server 2018 through modem 2086 and communication network 2024. If the connection fails for any reason, microprocessor 2076 repeats step 2328 to get a successful connection. In step 2330, microprocessor 2076 transmits the device measurements, query responses, script identification code, and patient identification code stored in memory 2080 to server 2018 through the subsequent communication link. In step 2332, microprocessor 2076 receives through modem 2086 a new script program from server 2018. The new script program is stored in memory 2080 for subsequent execution by microprocessor 2076. Following step 2332, the script program ends.

One advantage of the monitoring system of the present invention is that it allows each patient to select a convenient time to respond to the queries, so that the monitoring system is not intrusive to the patient's schedule. A second advantage of the monitoring system is that it incurs very low communications charges because each remote apparatus connects to the server at times when communication rates are lowest. Moreover, the cost to manufacture each remote apparatus is very low compared to personal computers or internet terminals, so that the monitoring system is highly affordable.

A third advantage of the monitoring system is that it allows each apparatus to be programmed remotely through script programs. Patient surveys, connection times, display prompts, selected monitoring devices, patient customization, and other operational details of each apparatus may be easily changed by transmitting a new script program to the apparatus. Moreover, each script program may be easily created and assigned by remotely accessing the server through the Internet. Thus, the invention provides a powerful, convenient, and inexpensive system for remotely monitoring a large number of patients.

Figure 25:
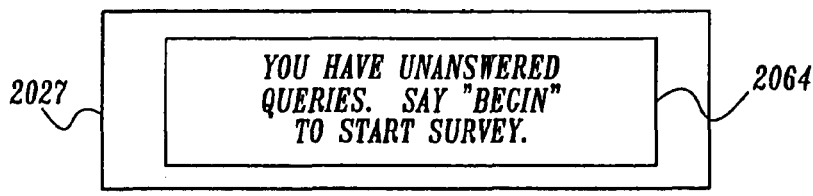
FIG. 25 is a sample prompt appearing on a display of the apparatus of FIG. 24.
Figure 26:
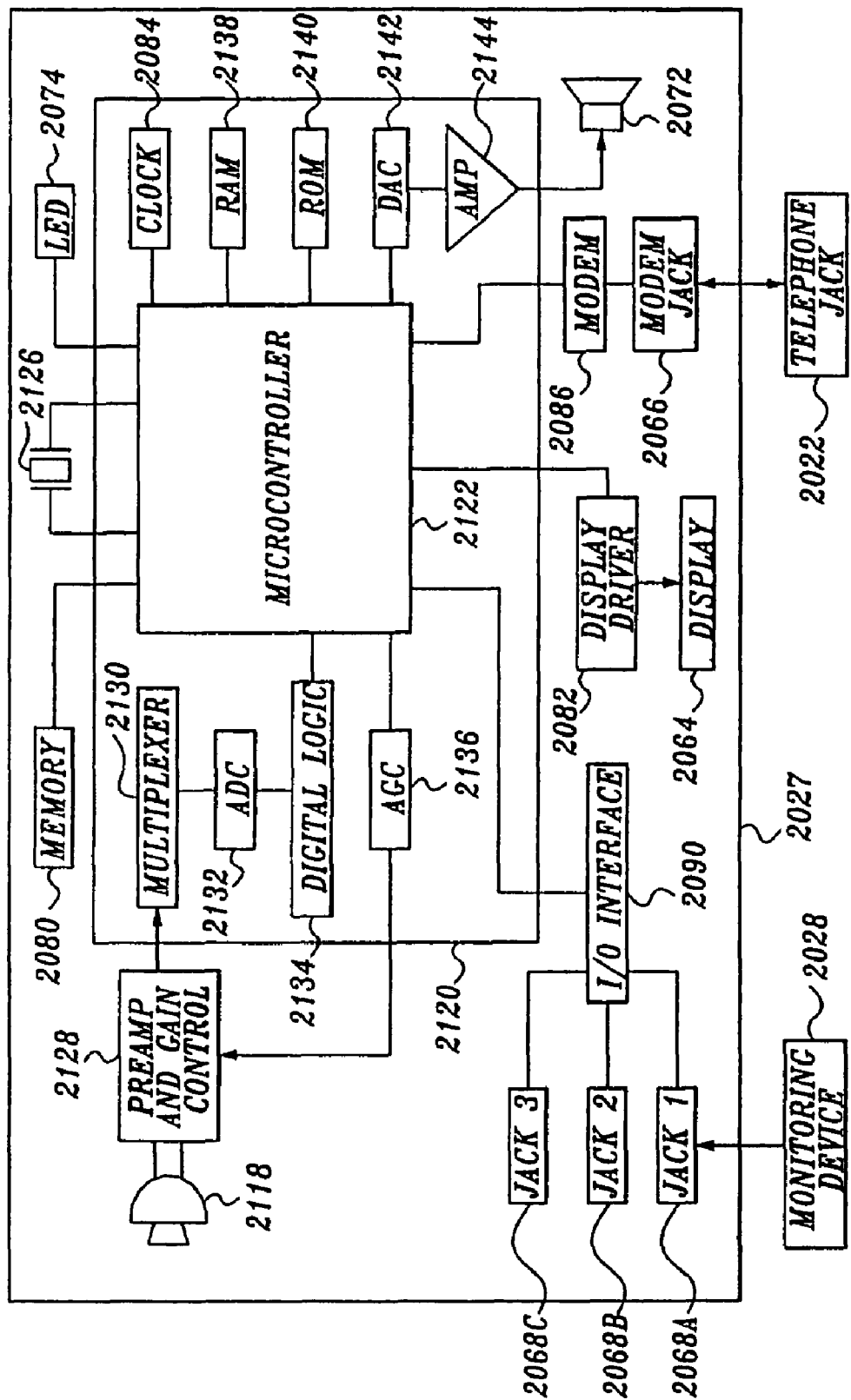
FIG. 26 is a block diagram illustrating the components of the apparatus of FIG. 24.

FIGS. 24-26 illustrate a second embodiment of the invention in which each remotely programmable apparatus has speech recognition and speech synthesis functionality. FIG. 24 shows a perspective view of an apparatus 2027 according to the second embodiment. Apparatus 2027 includes a speaker 2072 for audibly communicating queries and prompts to the patient. Apparatus 2027 also includes a microphone 2118 for receiving spoken responses to the queries and prompts. Apparatus 2027 may optionally include a display 2064 for displaying prompts to the patient, as shown in FIG. 25.

FIG. 26 is a schematic block diagram illustrating the components of apparatus 2027 in greater detail. Apparatus 2027 is similar in design to the apparatus of the preferred embodiment except that apparatus 2027 includes an audio processor chip 2120 in place of microprocessor 2076. Audio processor chip 2120 is preferably an RSC-164 chip commercially available from Sensory Circuits Inc. of 1735 N. First Street, San Jose, Calif. 95112.

Audio processor chip 2120 has a microcontroller 2122 for executing script programs received from the server. A memory 2080 is connected to microcontroller 2122. Memory 2080 stores the script programs and a script interpreter used by microcontroller 2122 to execute the script programs. Memory 2080 also stores measurements received from monitoring device 2028, responses to the queries, script identification codes, and the patient's unique identification code.

Audio processor chip 2120 also has built in speech synthesis functionality for synthesizing queries and prompts to a patient through speaker 2072. For speech synthesis, chip 2120 includes a digital to analog converter (DAC) 2142 and an amplifier 2144. DAC 2142 and amplifier 2144 drive speaker 2072 under the control of microcontroller 2122.

Audio processor chip 2120 further has built in speech recognition functionality for recognizing responses spoken into microphone 2118. Audio signals received through microphone 2118 are converted to electrical signals and sent to a preamp and gain control circuit 2128.

Preamp and gain control circuit 2128 is controlled by an automatic gain control circuit 2136, which is in turn controlled by microcontroller 2122. After being amplified by preamp 2128, the electrical signals enter chip 2120 and pass through a multiplexer 2130 and an analog to digital converter (ADC) 2132. The resulting digital signals pass through a digital logic circuit 2134 and enter microcontroller 2122 for speech recognition.

Audio processor chip 2120 also includes a RAM 2138 for short term memory storage and a ROM 2140 which stores programs executed by microcontroller 2122 to perform speech recognition and speech synthesis. Chip 2120 operates at a clock speed determined by a crystal 2126. Chip 2120 also includes a clock 2084 which provides the current date and time to microcontroller 2122. As in the preferred embodiment, apparatus 2027 includes an LED 2074, display driver 2082, modem 2086, and device interface 2090, all of which are connected to microcontroller 2122.

The operation of the second embodiment is similar to the operation of the preferred embodiment except that queries, response choices, and prompts are audibly communicated to the patient through speaker 2072 rather than being displayed to the patient on display 2064. The operation of the second embodiments also differs from the operation of the preferred embodiment in that responses to the queries and prompts are received through microphone 2118 rather than through user input buttons.

The script programs of the second embodiment are similar to the script program shown in FIGS. 17A-17B, except that each display command is replaced by a speech synthesis command and each input command is replaced by a speech recognition command. Referring to FIG. 26, the speech synthesis commands are executed by microcontroller 2122 to synthesize the queries, response choices, and prompts through speaker 2072. The speech recognition commands are executed by microcontroller 2122 to recognize responses spoken into microphone 2118.

For example, to ask the patient how he or she feels and record a response, microcontroller 2122 first executes a speech synthesis command to synthesize through speaker 2072 "How do you feel? Please answer with one of the following responses: very bad, bad, good, or very good." Next, microcontroller 2122 executes a speech recognition command to recognize the response spoken into microphone 1118. The recognized response is stored in memory 2080 and subsequently transmitted to the server. Other than the differences described, the operation and advantages of the second embodiment are the same as the operation and advantages of the preferred embodiment described above.

Although the first and second embodiments focus on querying individuals and collecting responses to the queries, the system of the invention is not limited to querying applications. The system may also be used simply to communicate messages to the individuals. FIGS. 27-30 illustrate a third embodiment in which the system is used to perform this automated messaging function. In the third embodiment, each script program contains a set of statements to be communicated to an individual rather than a set of queries to be answered by the individual. Of course, it will be apparent to one skilled in the art that the script programs may optionally include both queries and statements.

Figure 27:
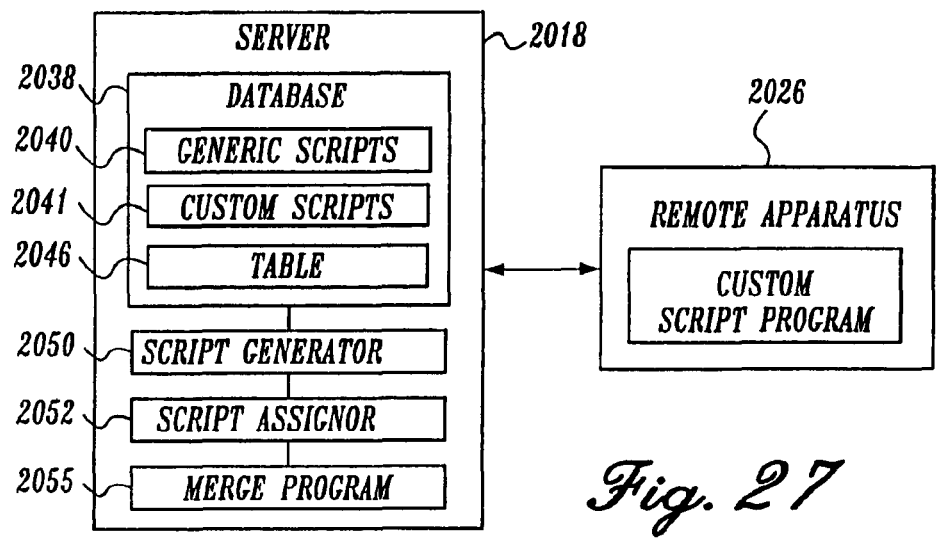
FIG. 27 is a schematic block diagram illustrating the interaction of the server of FIG. 12 with the apparatus of FIG. 14 according to a third embodiment of the invention.

The third embodiment also shows how the queries and statements may be customized to each individual by merging personal data with the script programs, much like a standard mail merge application. Referring to FIG. 27, personal data relating to each individual is preferably stored in look-up table 2046 of database 2038. By way of example, the data may include each individual's name, the name of each individual's physician, test results, appointment dates, or any other desired data. As in the preferred embodiment, database 2038 also stores generic script programs 2040 created by script generator 2050.

Figure 28:
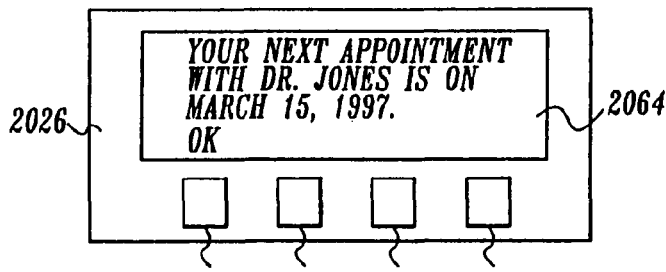
FIG. 28 is a first sample message appearing on the display of the apparatus of FIG. 14.
Figure 29:
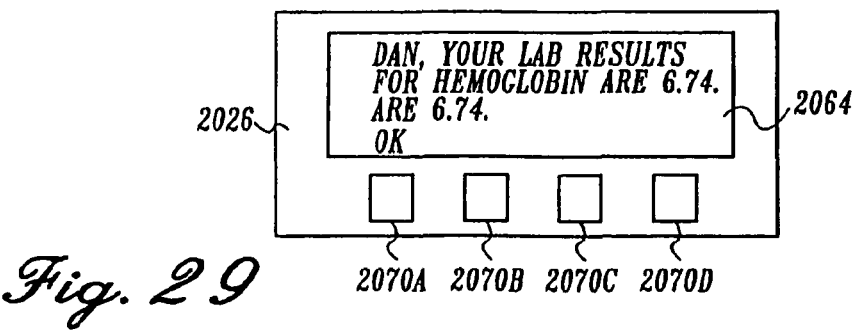
FIG. 29 is a second sample message appearing on the display of the apparatus of FIG. 14.

Server 2018 includes a data merge program 2055 for merging the data stored in table 2046 with generic script programs 2040. Data merge program 2055 is designed to retrieve selected data from table 2046 and to insert the data into statements in generic script programs 2040, thus creating custom script programs 2041. Each custom script program 2041 contains statements which are customized to an individual. For example, the statements may be customized with the individual's name, test results, etc. Examples of such customized statements are shown in FIGS. 28-29.

Figure 30:
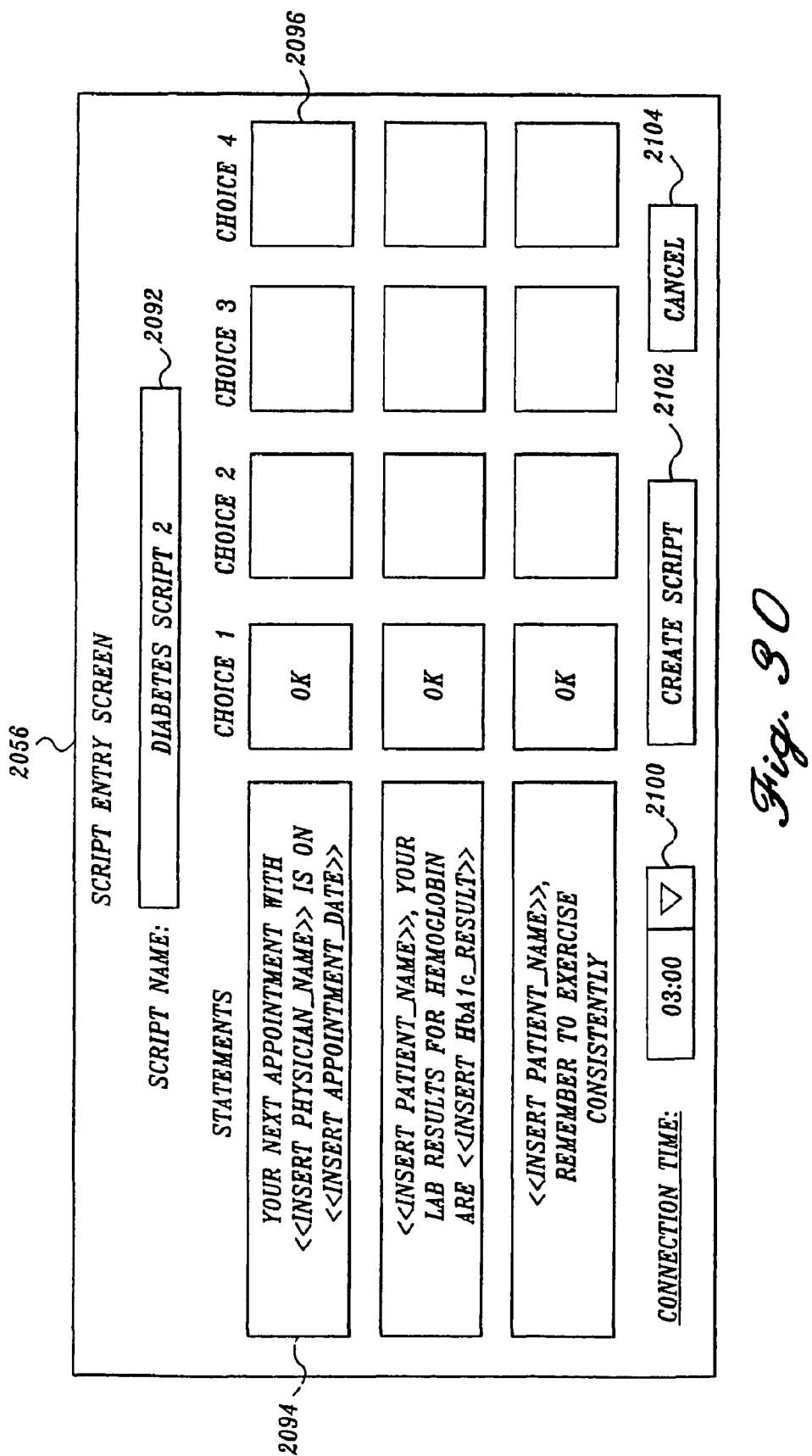
FIG. 30 is a script entry screen according to the third embodiment of the invention.

The operation of the third embodiment is similar to the operation of die preferred embodiment except that the script programs are used to communicate messages to the individuals rather than to query the individuals. Each message is preferably a set of statements. Referring to FIG. 30, the statements may be entered in the server through script entry screen 2056, just like the queries of the preferred embodiment.

Each statement preferably includes one or more insert commands specifying data from table 2046 to be inserted into the statement. The insert commands instruct data merge program 2055 to retrieve the specified data from database 2038 and to insert the data into the statement. For example, the insert commands shown in FIG. 30 instruct the data merge program to insert a physician name, an appointment date, a patient name, and a test result into the statements. As in the preferred embodiment, each statement may also include one or more response choices which are entered in fields 2096.

Following entry of the statements and response choices, CREATE SCRIPT button 2102 is pressed. When button 2102 is pressed, script generator 2050 generates a generic script program from the information entered in screen 2056. The generic script program is similar to the script program shown in FIGS. 17A-17B, except that the display commands specify statements to be displayed rather than queries. Further, the statements include insert commands specifying data to be inserted into the script program. As in the preferred embodiment, multiple script programs are preferably generated, e.g. a generic script program for diabetes patients, a generic script program for asthma patients, etc. The generic script programs are stored in database 2038.

Following generation of the generic script programs, server 2018 receives script assignment information entered through script assignment screen 2057. As shown in FIG. 18, the script programs are assigned by first selecting one of the generic script programs through check boxes 2106, selecting individuals through check boxes 2108, and pressing the ASSIGN SCRIPT button 2112. When button 2112 is pressed, data merge program 2055 creates a custom script program for each individual selected in check boxes 2108.

Each custom script program is preferably created by using the selected generic script program as a template. For each individual selected, data merge program 2055 retrieves from database 2038 the data specified in the insert commands. Next, data merge program 2055 inserts the data into the appropriate statements in the generic script program to create a custom script program for the individual. Each custom script program is stored in database 2038.

As each custom script program is generated for an individual, script assignor 2052 assigns the script program to die individual. This is preferably accomplished by creating a pointer to the custom script program and storing the pointer with the individual's unique identification code in table 2046. When the individual's remote apparatus connects to server 2018, server 2018 receives from the apparatus the individual's unique identification code. Server 2018 uses the unique identification code to retrieve from table 2046 the pointer to the custom script program assigned to the individual. Next, server 2018 retrieves the assigned script program from database 2038 and transmits the script program to the individual's apparatus through communication network 2024.

The apparatus receives and executes the script program. The execution of the script program is similar to the execution described in the preferred embodiment, except that statements are displayed to the individual rather than queries. FIGS. 28-29 illustrate two sample statements as they appear on display 2064. Each statement includes a response choice, preferably an acknowledgment such as "OK". After reading a statement, the individual presses the button corresponding to the response choice to proceed to the next statement. Alternatively, the script program may specify a period of tine that each statement is to be displayed before proceeding to the next statement. The remaining operation of the third embodiment is analogous to the operation of the preferred embodiment described above.

Although it is presently preferred to generate a custom script program for each individual as soon as script assignment information is received for the individual, it is also possible to wait until the individual's apparatus connects to the server before generating the custom script program. This is accomplished by creating and storing a pointer to the generic script program assigned to the individual, as previously described in the preferred embodiment. When the individual's apparatus connects to the server, data merge program 2055 creates a custom script program for the individual from the generic script program assigned to the individual. The custom script program is then sent to the individual's apparatus for execution.

Synopsis of the Detailed Description

Figure 31:
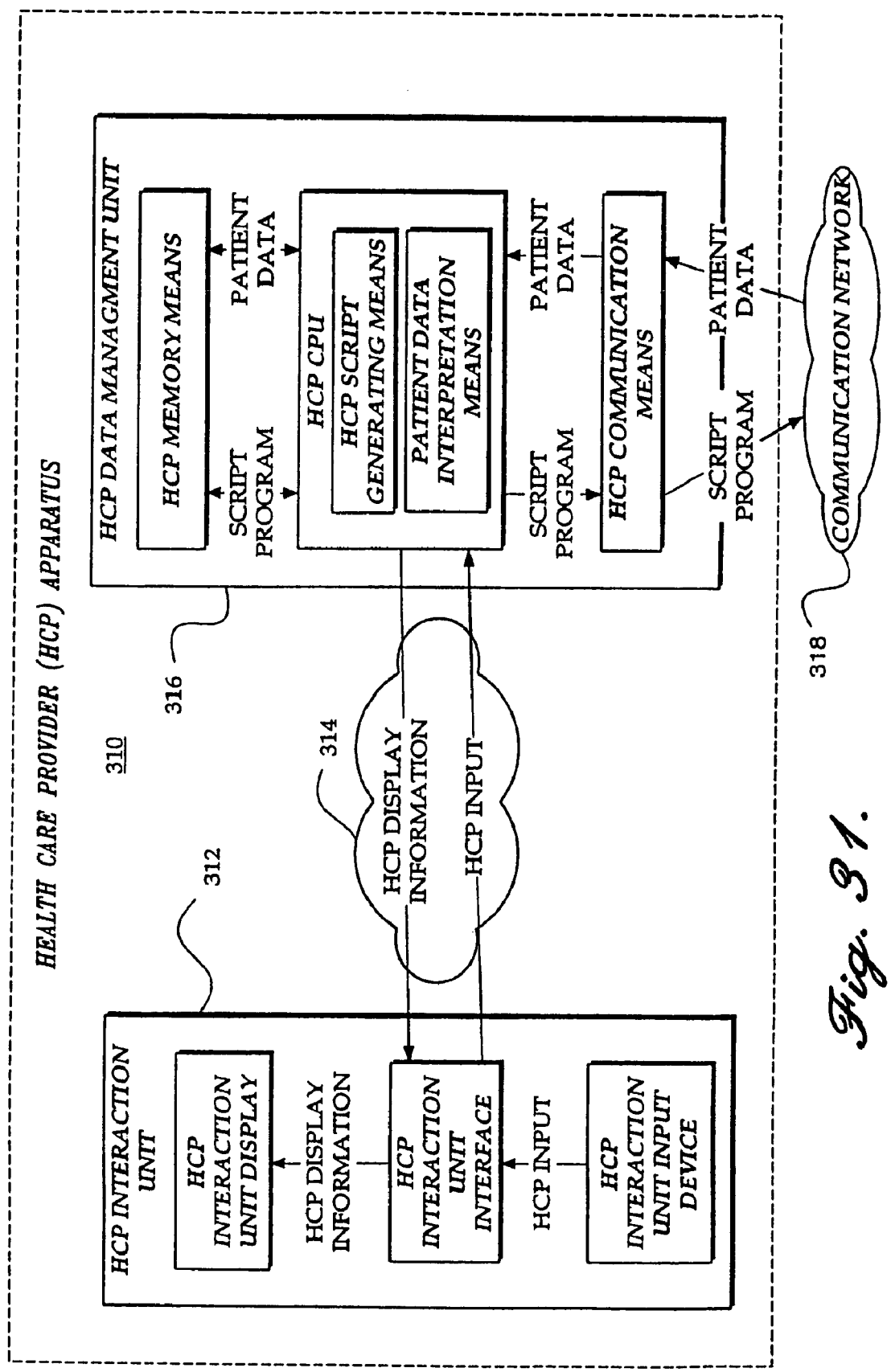
FIG. 31 is a block diagram summarizing the Health Care Provider Apparatus of the present invention.
Figure 32:
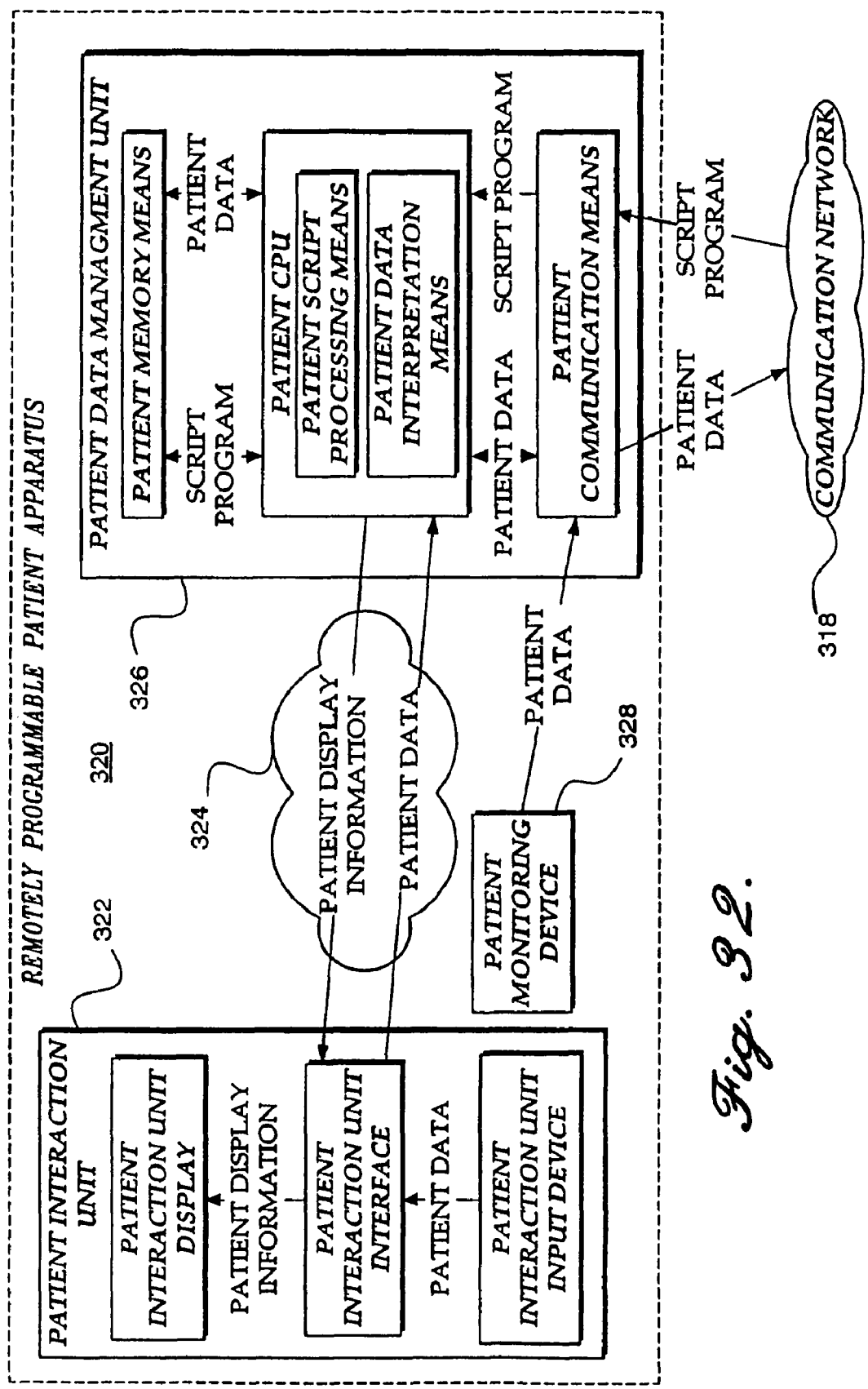
FIG. 32 is a block diagram summarizing the Remotely Programmable Patient Apparatus of the present invention.

FIGS. 31 and 32 provide a synopsis of the system and method of the invention that is described above. FIG. 31 illustrates a Health Care Provider (HCP) apparatus 310, comprising a HCP Interaction Unit 312 that is connected through a patient communication network 314 to a HCP Data Management Unit 316. In the detailed description above, the HCP Interaction Unit 312 is variously described as a doctor's fax 55 (FIG. 2), a doctor's computer 62 (FIG. 2), or a workstation 2020 (FIG. 12), which may be a personal computer, remote terminal, or web TV unit. The HCP Data Management Unit 316 is alternatively described above as a clearinghouse 54 (FIGS. 1-2) or a server 2018 (FIG. 12), which is described as a stand-alone personal computer or a network of computers. The patient communication network 312 is variously referred to above as the communication network 2024 (preferably the Internet) (FIG. 12), a telephone line 64, or a second telephone line 68. As would be apparent to one skilled in the art, the patient communication network 312 may also simply be a wire or a cable. The Health Care Provider Apparatus 310 is coupled to a communication network 318, which is described above as a telephone line 50 and modem 52 or as communication network 2024, preferably the Internet.

In FIG. 32, the Remotely Programmable Patient Apparatus 320 comprises a Patient Interaction Unit 322, which is connected through a patient communication network 324 to a Patient Data Management. Unit 326. In the detailed description above, the Remotely Programmable Patient Apparatus 320 is sometimes referred to as an individual self-care health monitoring system 58 (FIG. 2). The Patient Interaction Unit 322 is variously described as handheld microprocessor unit 12 (FIG. 1), a commercially available compact video game system (such as the system manufactured by Nintendo of America Inc. under the trademark "GAME BOY") (see e.g., FIG. 1), a game console 102 (FIG. 11), a palm-top computer, or a remote apparatus 2026, 2032 (FIGS. 12 and 14). The Patient Data Management Unit 326 is alternatively described above as being a part of the remote apparatus 2026, 2032 (FIGS. 12 and 14) or as being a separate data management unit 10 (FIG. 1). The patient communication network 324 is sometimes referred to above as a cable 14 and may also be a wire or other signal communication medium, as would be apparent to those skilled in the art. The Remotely Programmable Patient Apparatus 320 is also coupled to the communication network 318. The patient monitoring device 328 illustrated in FIG. 32 is variously referred to above as the blood glucose monitor 16, peak flow meter 20, additional monitor 22 (FIG. 1), or monitoring device 2028 (FIG. 12).

The preceding synopsis is intended only to provide a summary overview of the present invention as described above and is not intended to reiterate all the functional equivalents for the components of the Health Care Provider Apparatus 310 and the Remotely Programmable Patient Apparatus 320 which have been described above or to describe those functional equivalents that would be apparent to one skilled in the art.

SUMMARY, RAMIFICATIONS, AND SCOPE

Although the above description contains many specificities, these should not be construed as limitations on the scope of the invention but merely as illustrations of some of the presently preferred embodiments. Many other embodiments of the invention are possible. For example, the scripting language and script commands shown are representative of the preferred embodiment. It will be apparent to one skilled in the art many other scripting languages and specific script commands may be used to implement the invention.

Moreover, the invention is not limited to the specific applications described. The system and method of the invention have many other application both inside and outside the healthcare industry. For example, pharmaceutical manufacturers may apply the system in the clinical development and post marketing surveillance of new drugs, using the system as an interactive, on-line monitoring tool for collecting data on the efficacy, side effects, and quality of life impact of the drugs. Compared to the current use of labor intensive patient interviews, the system provides a fast, flexible, and cost effective alternative for monitoring the use and effects of the drugs.

The system may also be used by home healthcare companies to enhance the service levels provided to customers, e.g. panic systems, sleep surveillance, specific monitoring of disease conditions, etc. Alternatively, the system may be used to monitor and optimize the inventory of home stationed health supplies. As an example, the system may be connected to an appropriate measuring device to optimize timing of oxygen tank delivery to patients with COPD.

The system and method of the invention also have many applications outside the healthcare industry. For example, the system may be used for remote education over the Internet, facilitating educational communication with children or adult trainees who lack access to sophisticated and expensive computer equipment. The system may also be used by law enforcement officers to perform on-line surveillance of individuals on probation or parole.

Further, the invention has numerous applications for gathering data from remotely located devices. For example, the system may be used to collect data from smart appliances, such as identification check systems. Alternatively, the system may be applied to the remote monitoring of facilities, including safety and security monitoring, or to environmental monitoring, including pollution control and pipeline monitoring. Many other suitable applications of the invention will be apparent to one skilled in the art.

The invention claimed is:

1. A system for performing diabetes self-care using at least two devices in communication with one another, comprising:
  (a) a blood glucose monitoring device associated with a user, including
    (i) a receptacle for receiving an amount of blood sufficient for the blood glucose monitoring device to run a blood glucose test sequence,
    (ii) processing circuitry for controlling said blood glucose test sequence and computing a blood glucose level, and
    (iii) a power source for powering the blood glucose monitoring device; and
  (b) a portable microprocessor-based device associated with said user, separate from the blood glucose monitoring device and configured for receiving blood glucose test results directly from said blood glucose monitoring device, said portable microprocessor-based device including
    (i) a microprocessor that executes program instructions stored in a memory, said program instructions when executed performing analysis of the blood glucose test results and detecting a need for a change in insulin dosage, and (ii) said memory for (A) recording the blood glucose test results received from the blood glucose monitoring device, (B) storing said program instructions for establishing a data protocol that allows digital data signal processing, (C) storing said program instructions for performing said analysis of the blood glucose test results, (D) storing time and date tags associated with the blood glucose test results and (E) storing calibration information.

2. The system of claim 1, wherein said receptacle is for receiving a test strip upon which a drop of blood is applied.

3. The system of claim 1, wherein said portable microprocessor-based device includes a palm-top computer.

4. The system of claim 1, wherein the program instructions further include instructions for processing insulin dosage data.

5. The system of claim 2, the program instructions further include instructions for monitoring whether said test strip is properly inserted into the blood glucose monitoring device.

6. The system of claim 1, wherein the program instructions further include instructions for performing a test sequence to confirm that the system is operating properly.

7. The system of claim 1, wherein said program instructions further include instructions for running a calibration procedure that involves reading a code strip inserted into the blood glucose monitoring device.

8. A system for performing diabetes self-care using at least two devices in communication with one another, comprising:
(a) a blood glucose monitoring device associated with a system user, including
  (i) a receptacle for receiving an amount of blood sufficient for the blood glucose monitoring device to run a blood glucose test sequence,
  (ii) processing circuitry for controlling said blood glucose test sequence and computing a blood glucose level, and
  (iii) a power source for powering the blood glucose monitoring device; and
(b) a portable microprocessor-based device associated with said system user, separate from the blood glucose monitoring device and configured for receiving blood glucose test results directly from said blood glucose monitoring device, said portable microprocessor-based device including
  (i) a microprocessor that executes program instructions stored in a memory, said program instructions when executed performing analysis of the blood glucose test results and monitoring food intake,
  (ii) said memory for (A) recording the blood glucose test results received from the blood glucose monitoring device, (B) storing said program instructions for establishing a data protocol that allows digital data signal processing, (C) storing said program instructions for performing said analysis of the blood glucose test results, (D) storing insulin dosage data and (E) storing calibration information.

9. The system of claim 8, wherein said receptacle is for receiving a test strip upon which a drop of blood is applied.

10. The system of claim 9, wherein the program instructions further include instructions for monitoring whether a sufficient amount of blood has been applied to a reagent impregnated portion of the test strip.

11. The system of claim 9, wherein the program instructions further include instructions for monitoring whether said test strip is properly inserted into the blood glucose monitoring device.

12. The system of claim 8, wherein the program instructions further include instructions for performing a test sequence to confirm that the system is operating properly.

13. The system of claim 8, wherein the portable microprocessor-based device comprises a user interface, including:
(i) a display screen; and
(ii) a plurality of switches including a pair of spaced-apart push button switches and another pair of switches.

14. The system of claim 8, wherein said food intake is monitored quantitatively in terms of "Bread Exchange" units or other suitable terms.

15. The system of claim 14, wherein said food intake is monitored by providing a food intake menu item and using a submenu display, and providing for the selecting of one or more food items using switches of the portable microprocessor-based device.

16. The system of claim 8, wherein food intake data is stored along with time and date tagged blood glucose test results.

17. The system of claim 8, wherein the program instructions further include instructions for monitoring exercise.

18. A system for performing diabetes self-care using at least two devices in communication with one another, comprising:
(a) a blood glucose monitoring device associated with a system user, including
  (i) a receptacle for receiving an amount of blood sufficient for the blood glucose monitoring device to run a blood glucose test sequence;
  (ii) processing circuitry for controlling said blood glucose test sequence and computing a blood glucose level, and
  (iii) a power source for powering the blood glucose monitoring device; and
(b) a portable microprocessor-based device associated with said system user, separate from the blood glucose monitoring device and configured for receiving blood glucose test results directly from said blood glucose monitoring device, said portable microprocessor-based device including
  (i) a microprocessor that executes program instructions stored in a memory for performing analysis of the blood glucose test results and indicating trend information of said system user, and
  (ii) said memory for (A) recording the blood glucose test results, (B) storing said program instructions for establishing a data protocol that allows digital data signal processing, (C) storing said program instructions for performing said analysis of the blood glucose test results, and (D) storing calibration information.

19. The system of claim 18, wherein said receptacle is configured for receiving a test strip upon which a drop of blood is applied.

20. The system of claim 19, wherein the program instructions further include instructions for monitoring whether a sufficient amount of blood has been applied to a reagent impregnated portion of said test strip.

21. The system of claim 19, wherein the program instructions further include instructions for monitoring whether said test strip is properly inserted into the blood glucose monitoring device.

22. The system of claim 18, wherein the program instructions further include instructions for performing a test sequence to confirm that the system is operating properly.

23. The system of claim 18, wherein said trend information is displayed in graphic format.

24. The system of claim 18, wherein said trend information is displayed in alphanumeric format.

25. The system of claim 18, wherein the system is configured for displaying daily or weekly trend information, or both.

26. A blood glucose monitoring system, comprising:
- a. a blood glucose monitoring device configured for producing digitally encoded blood glucose signals representative of a blood glucose level of a system user;
- b. a programmable microprocessor-based portable unit associated with said system user, separate from said blood glucose monitoring device and comprising a signal interface connectable with said blood glucose monitoring device for retrieving said digitally encoded blood glucose signals from said blood glucose monitoring device to said programmable microprocessor-based portable unit; and
- c. a digital data storage medium, wherein the digital data storage medium
  - A. is readable by said programmable microprocessor-based portable unit; and
  - B. stores program instructions which when executed by said programmable microprocessor-based portable unit, perform (i) signal processing of signals generated based upon said digitally encoded blood glucose signals, (ii) signal processing of insulin dosage data and (iii) detection of a need for a change in insulin dosage.

27. The system of claim 26, wherein said programmable microprocessor-based portable unit comprises a palm-top computer.

28. The system of claim 26, wherein the blood glucose monitoring device is further configured for receiving a test strip including a reagent impregnated portion configured for having blood applied thereto.

29. The system of claim 28, wherein the program instructions further include instructions for monitoring whether a sufficient amount of blood has been applied to said reagent impregnated portion of the test strip.

30. The system of claim 29, wherein the program instructions further include instructions for monitoring whether said test strip is properly inserted into the blood glucose monitoring device.

31. The system of claim 28, wherein the program instructions further include instructions for monitoring whether said test strip is properly inserted into the blood glucose monitoring device.

32. The system of claim 28, wherein the program instructions further include instructions for performing a test sequence to confirm that the system is operating properly.

33. The system of claim 26, wherein said signal interface is further connectable with a second device, other than said blood glucose monitoring device, for coupling signals supplied by said second device to said programmable microprocessor-based portable unit.

34. The system of claim 26, wherein said programmable microprocessor-based portable unit comprises a user interface, including:
1) a display for displaying information;
2) a plurality of switches operable for interactively controlling said programmable microprocessor-based portable unit and for manipulating said information displayed on said display; and
3) a circuit coupled to said plurality of switches for generating signals in response to said operation of switches.

35. The system of claim 34, wherein said programmable microprocessor-based portable unit is a palm-top computer.

36. The system of claim 34, wherein the blood glucose monitoring device is further configured for receiving a test strip including a reagent impregnated portion configured for having blood applied thereto.

37. The system of claim 36, wherein the program instructions further include instructions for monitoring whether a sufficient amount of blood has been applied to said reagent impregnated portion of the test strip.

38. The system of claim 37, wherein the program instructions further include instructions for monitoring whether said test strip is properly inserted into the blood glucose monitoring device.

39. The system of claim 36, wherein the program instructions further include instructions for monitoring whether said test strip is properly inserted into the blood glucose monitoring device.

40. The system of claim 36, wherein the program instructions further include instructions for performing a test sequence to confirm that the system is operating properly.

41. The system of claim 34, wherein said signal interface is connectable with a second device, other than said blood glucose monitoring device, for coupling signals supplied by said second device to said programmable microprocessor-based portable unit.

42. A system of interconnected devices for performing diabetes self-care, comprising:
- (a) a portable blood glucose monitoring device associated with a system user, including
  - (i) a receptacle for receiving an amount of blood sufficient for the blood glucose monitoring device to run a blood glucose test sequence,
  - (ii) processing circuitry for controlling said blood glucose test sequence and computing a blood glucose level,
  - (iii) a first data port for signal coupling to another electronic device; and
- (b) a portable microprocessor-based device associated with said system user, separate from the portable blood glucose monitoring device and configured for communicating diabetes care data with the portable blood glucose monitoring device, said portable microprocessor-based device including
  - a second data port for signal coupling with the first data port and receiving blood glucose test results from said blood glucose monitoring device,
  - a microprocessor that executes program instructions stored in a memory, said program instructions for performing analysis of the blood glucose test results, signal processing of insulin dosage data, and detecting a need for a change in insulin dosage,
  - said memory for (i) recording the blood glucose test results and insulin dosage data, (ii) said storing program instructions for establishing a data protocol that allows digital data signal processing, and (iii) storing program instructions for performing said analysis of said blood glucose test results.

43. The system of interconnected devices of claim 42, wherein the program instructions further include instructions for monitoring whether a sufficient amount of blood has been applied to a reagent impregnated portion of a test strip.

44. The system of interconnected devices of claim 42, wherein the blood glucose monitoring device is configured to receive a test strip including a reagent impregnated portion configured for having blood applied thereto.

45. The system of interconnected devices of claim 44, wherein the program instructions further includes instructions for monitoring whether a sufficient amount of blood has been applied to the reagent impregnated portion of the test strip.

46. The system of interconnected devices of claim 44, wherein the program instructions further includes instructions for monitoring whether the test strip is properly inserted into the blood glucose monitoring device.

47. The system of interconnected devices of claim 42, wherein the program instructions further include instructions for performing a test sequence to confirm that the system is operating properly.

48. The system of claim 42, further comprising a second device, other than said blood glucose monitoring device, comprising a third data port, wherein said second data port of said portable microprocessor-based device is further configured for signal coupling with the third data port and receiving a signal from said second device.

49. A system of integrated electronic devices, including one or more processor-readable storage devices having program code embodied thereon for programming one or more processors associated with one or more of the devices to perform a method comprising:
   (a) powering a portable blood glucose monitoring device associated with a system user;
   (b) receiving an amount of blood, wherein the amount of blood received is sufficient for the portable blood glucose monitoring device to run a blood glucose test sequence;
   (c) controlling the blood glucose test sequence;
   (d) computing a blood glucose level;
   (e) transmitting blood glucose test results from said portable blood glucose monitoring device directly to a portable microprocessor-based device that is separate from the portable blood glucose monitoring device and associated with said system user;
   (f) performing analysis of the blood glucose test results,
   (g) signal processing of insulin dosage data;
   (h) detecting a need for a change in insulin dosage; and
   (i) recording date and time stamped blood glucose test results, calibration information, and said insulin dosage data in a memory of the system; and
   (j) establishing a data protocol that allows digital data signal processing and said analysis of the blood glucose test results.

50. The system of claim 49, wherein receiving the amount of blood comprises (i) inserting a test strip into a receptacle of the portable blood glucose monitoring device and (ii) applying a drop of blood to the test strip.

51. The system of claim 49, wherein the method further comprises displaying the blood glucose level on a display.

52. The system of claim 49, wherein controlling the blood glucose test sequence comprises monitoring whether the sufficient amount of blood has been applied to a reagent impregnated portion of a test strip.

53. The system of claim 49, wherein controlling the blood glucose test sequence comprises monitoring whether a test strip is properly inserted into the portable blood glucose monitoring device.

54. The system of claim 49, wherein controlling the blood glucose test sequence comprises performing a test sequence to confirm that the system is operating properly.

55. The system of claim 49, wherein the method further comprises running a calibration procedure by reading a code strip inserted into the portable blood glucose monitoring device.

56. A system of integrated electronic devices, including one or more processor-readable storage devices having program code embodied thereon for programming one or more processors associated with one or more of the devices to perform a method comprising:
   (a) powering a portable blood glucose monitoring device associated with a system user;
   (b) receiving an amount of blood, wherein the amount of blood is sufficient for the portable blood glucose monitoring device to run a blood glucose test sequence;
   (c) controlling the blood glucose test sequence;
   (d) computing a blood glucose level;
   (e) coupling the portable blood glucose monitoring device directly to a portable microprocessor-based device that is separate from the portable blood glucose monitoring device and associated with said system user;
   (f) transmitting blood glucose test results from said portable blood glucose monitoring device directly to said portable microprocessor-based device;
   (g) running program instructions stored in a memory of the portable microprocessor-based device, said program instructions for performing analysis of the blood glucose test results, signal processing of insulin dosage data, and detecting a need for a change in insulin dosage; and
   (h) recording the blood glucose test results and the insulin dosage data in a memory of the portable microprocessor-based device, said memory also containing program instructions for establishing a data protocol that allows digital data signal processing.

57. The system of claim 56, wherein receiving the amount of blood comprises (i) inserting a test strip into a receptacle of the portable blood glucose monitoring device and (ii) applying a drop of blood to the strip.

58. The system of claim 56, wherein the method further comprises displaying the blood glucose level on a display.

59. The system of claim 56, wherein said portable microprocessor-based device comprises a palm-top computer.

60. The system of claim 56, wherein receiving the amount of blood comprises inserting a test strip including a reagent impregnated portion for having blood applied thereto.

61. The system of claim 60, wherein controlling the blood glucose test sequence comprises monitoring whether the sufficient amount of blood has been applied to the reagent impregnated portion of the test strip.

62. The system of claim 56, wherein controlling the blood glucose test sequence comprises performing a test sequence to confirm that the system is operating properly.

63. The system of claim 56, wherein the method further comprises monitoring food intake quantitatively in terms of "Bread Exchange" units or other suitable terms.

64. The system of claim 56, wherein the method further comprises storing food intake data along with time and date tagged blood glucose test results.

65. The system of claim 56, wherein the method further comprises monitoring exercise.

66. A system of integrated electronic devices, including one or more processor-readable storage devices having program code embodied thereon for programming one or more processors associated with one or more of the devices to perform a method comprising:
   (a) powering a portable blood glucose monitoring device associated with a system user;
   (b) receiving an amount of blood sufficient for the portable blood glucose monitoring device to run a blood glucose test sequence;
   (c) controlling the blood glucose test sequence;
   (d) computing a blood glucose level;
   (e) transmitting blood glucose test results from said portable blood glucose monitoring device directly to a portable microprocessor-based device that is separate from said portable blood glucose monitoring device associated with said system user;
(f) running program instructions stored in a memory of the portable microprocessor-based device, said program instructions for performing analysis of the blood glucose test results, signal processing of insulin dosage information, and detecting a need for a change in insulin dosage;
(g) recording the blood glucose test results and the insulin dosage information in said memory of the portable microprocessor-based device, said memory also containing program instructions for establishing a data protocol that allows digital data signal processing; and
(h) indicating trend information of said system user.

67. The system of claim 66, wherein receiving the amount of blood comprises (i) inserting a test strip into a receptacle of the portable blood glucose monitoring device, and (ii) applying a drop of blood to the strip.

68. The system of claim 66, wherein the method further comprises displaying the blood glucose level on a display.

69. The system of claim 66, wherein receiving the amount of blood comprises inserting a test strip including a reagent impregnated portion for having blood applied thereto.

70. The system of claim 69, wherein controlling the blood glucose test sequence comprises monitoring whether the sufficient amount of blood has been applied to the reagent impregnated portion of the test strip.

71. The system of claim 66, wherein the method further comprises displaying said trend information in graphic format.

72. The system of claim 66, wherein the method further comprises displaying said trend information in alphanumeric format.

73. The system of claim 66, wherein the method further comprises displaying daily or weekly trend information, or both.

* * * * *